(12) United States Patent
Ohta et al.

(10) Patent No.: US 8,744,043 B2
(45) Date of Patent: Jun. 3, 2014

(54) RADIATION IMAGE CAPTURING DEVICE AND RADIATION IMAGE CAPTURING SYSTEM

(75) Inventors: Yasunori Ohta, Kanagawa (JP); Naoyuki Nishino, Kanagawa (JP); Haruyasu Nakatsugawa, Kanagawa (JP); Yutaka Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 691 days.

(21) Appl. No.: 12/975,385

(22) Filed: Dec. 22, 2010

(65) Prior Publication Data

US 2011/0164724 A1 Jul. 7, 2011

(30) Foreign Application Priority Data

| Jan. 5, 2010 | (JP) | 2010-000711 |
| Mar. 19, 2010 | (JP) | 2010-064671 |
| Mar. 19, 2010 | (JP) | 2010-064990 |
| Mar. 19, 2010 | (JP) | 2010-064991 |
| Dec. 10, 2010 | (JP) | 2010-275599 |
| Dec. 10, 2010 | (JP) | 2010-275600 |
| Dec. 10, 2010 | (JP) | 2010-275601 |
| Dec. 10, 2010 | (JP) | 2010-275602 |

(51) Int. Cl.
*H05G 1/42* (2006.01)
*A61B 6/00* (2006.01)

(52) U.S. Cl.
USPC .............................. 378/62; 378/97

(58) Field of Classification Search
USPC .............. 378/62, 108, 156–159, 147–153
See application file for complete search history.

(56) References Cited

U.S. PATENT DOCUMENTS 5,278,887 A * 1/1994 Chiu et al. ............... 378/156
7,085,355 B1 8/2006 Albagli et al.
(Continued)

FOREIGN PATENT DOCUMENTS

| JP | S63-290546 | 11/1988 |
| JP | 5-161639 A | 6/1993 |

(Continued)

OTHER PUBLICATIONS

English language translation of the following: Office action dated Jan. 28, 2014 from the JPO in a Japanese patent application No. 2010-275602 corresponding to the instant patent application. This office action translation is submitted now in order to supplement the understanding of patent document JP2006-317440, JP2006-290546 and JP2003-060181 which are cited in the office action and are being disclosed in the instant Information Disclosure Statement.

(Continued)

*Primary Examiner* — Irakli Kiknadze
(74) *Attorney, Agent, or Firm* — SOLARIS Intellectual Property Group, PLLC

(57) ABSTRACT

A radiation image capturing device includes a radiation image capturing unit, a diaphragm unit, and a control unit. The radiation image capturing unit captures a radiation image based on radiation transmitted through a subject. The diaphragm unit has an opening region that is configured to transmit a part of the radiation emitted from a radiation source and an area thereof is changeable, and the diaphragm unit is configured such that a transmission dose of the radiation decreases as a distance from a circumferential part of the opening region increases. The control unit controls the diaphragm unit such that direct rays of the radiation are irradiated onto a predetermined region of the subject.

16 Claims, 25 Drawing Sheets

(56) References Cited

U.S. PATENT DOCUMENTS

| | | | |
|---|---|---|---|
| 8,213,569 B2 * | 7/2012 | Zaiki et al. | 378/16 |
| 2004/0028182 A1 * | 2/2004 | Tamegai | 378/98.7 |
| 2009/0074143 A1 * | 3/2009 | Tsukagoshi et al. | 378/97 |

FOREIGN PATENT DOCUMENTS

| | | |
|---|---|---|
| JP | 5-329138 A | 12/1993 |
| JP | 11-142597 A | 5/1999 |
| JP | 2001-17416 A | 1/2001 |
| JP | 2003-060181 | 2/2003 |
| JP | 2005-27823 A | 2/2005 |
| JP | 2005-198762 A | 7/2005 |
| JP | 2006-317440 | 11/2006 |
| JP | 2007-97909 A | 4/2007 |
| JP | 2007-244489 | 9/2007 |
| JP | 2008-119195 A | 5/2008 |
| JP | 2008-220480 A | 9/2008 |
| JP | 2008-272381 A | 11/2008 |
| JP | 2009-160308 A | 7/2009 |
| JP | 2009-212389 A | 9/2009 |
| JP | 2009-213905 A | 9/2009 |

OTHER PUBLICATIONS

English language translation of the following: Office action dated Jan. 28, 2014 from the JPO in a Japanese patent application No. 2010-275601 corresponding to the instant patent application. This office action translation is submitted now in order to supplement the understanding of patent document JP2003-060181 and JP2007-244489 which are cited in the office action and are being disclosed in the instant Information Disclosure Statement.

* cited by examiner

| PART | EXPOSURE DOSE THRESHOLD VALUE(mGy) |
|---|---|
| HEART | . . . . |
| LUNG | . . . . |
| STOMACH | . . . . |
| ⋮ | ⋮ |

FIG.14

EXPOSURE DOSE HISTORY INFORMATION

| ID | IMAGE CAPTURING DATE AND TIME | EXPOSURE REGION | EXPOSURE DOSE(mGy) | EXPOSURE PERIOD(SEC) | FRAME RATE (fps) |
|---|---|---|---|---|---|
| 01-001 | 2010/02/16 14:20~14:30 | (123,456) | XXXX | 0.066 | 15 |
| | | (124,456) | XXXX | 0.066 | |
| | | ⋮ | ⋮ | ⋮ | |
| | 2010/02/23 13:10~13:25 | (124,457) | XXXX | 0.033 | 30 |
| | | (125,457) | XXXX | 0.033 | |
| | | ⋮ | ⋮ | ⋮ | |
| 01-002 | ⋮ | ⋮ | ⋮ | ⋮ | ⋮ |
| ⋮ | ⋮ | ⋮ | ⋮ | ⋮ | ⋮ |

FIG.15

WEIGHT VALUE MANAGEMENT INFORMATION

| PARAMETER | CONDITION | WEIGHT VALUE |
|---|---|---|
| PROGRESS PERIOD t (MIN) | t<1440 | 1 |
| | 1440≦t<10080 | 0.9 |
| | 10080≦t<40320 | 0.8 |
| | ⋮ | ⋮ |

RADIATION IMAGE CAPTURING DEVICE AND RADIATION IMAGE CAPTURING SYSTEM

CROSS-REFERENCE TO RELATED APPLICATIONS

This application claims priority under 35 USC 119 from Japanese Patent Applications No. 2010-000711 filed on Jan. 5, 2010, No. 2010-064671, No. 2010-064990 and No. 2010-064991 filed on Mar. 19, 2010, and Nos. 2010-275599, 2010-275600, 2010-275601 and 2010-275602 filed on Dec. 10, 2010 the disclosures of which are incorporated by reference herein.

BACKGROUND OF THE INVENTION

1. Field of the Invention

The invention relates to a radiation image capturing device and a radiation image capturing system and more particularly, to a radiation image capturing device and a radiation image capturing system, each including a radiation image capturing unit.

2. Description of the Related Art

In recent years, interventional radiology (IVR) has rapidly spread in medical treatment is performed by inserting a catheter having a tip end mounted with various instruments into a body of a patient, making the tip end of the catheter arrive at a lesion part of the patient's body while monitoring a state of the body of the patient in real time on the basis of a radiation image displayed on a monitor, and operating the catheter at the outside of the body.

A technician performs a medical treatment while observing a radiation image displayed on a monitor at the time of executing IVR. Accordingly, as treatment time increases, a patient is exposed to a larger dose of radiation.

Japanese Patent Application Laid-Open (JP-A) No. 2008-220480 discloses a radiographic imaging device that can capture a radiation image by automatically setting an irradiation range and therefore a radiation irradiation condition depending on the position of a treatment instrument inserted into a subject to thereby reduce an exposure dose with respect to the subject. The radiographic imaging device includes a radiation detector in which plural radiation detecting elements are arranged two-dimensionally, and irradiates radiation emitted from a radiation source onto the radiation detector through the subject to capture a radiation image. The radiographic imaging device includes an instrument detecting unit that processes the radiation image captured by the radiation detector and detects the treatment instrument inserted into the subject, a position calculating unit that calculates the position of the detected treatment instrument in the subject, and a setting unit that sets the irradiation range of the radiation including the treatment instrument according to the calculated position of the treatment instrument in the subject and sets the radiation irradiation condition with respect to the irradiation range, and captures the radiation image within the set irradiation range according to the set radiation irradiation condition.

JP-A No. 5-161639 discloses a radiographic imaging device for selecting an optimal adjusting unit according to an imaging part in control for adjustment of an irradiation dose based on detection of a transmission dose. The radiographic imaging device detects a dose of radiation transmitted through an object by scanning and operating a radiation fan beam, and captures a radiation projection image. The radiographic imaging device includes a transmitted radiation dose detecting unit that has plural detecting elements arranged in a longitudinal direction of the radiation fan beam and outputs a detection signal according to the dose of radiation transmitted through the object for each detecting element, a first radiation dose adjusting unit that arranges plural radiation shielding members, the number of which is equal to the number of detecting elements, in the longitudinal direction of the radiation fan beam and adjusts a radiation transmission opening area at plural points in the longitudinal direction of the radiation fan beam by displacement of the plural radiation shielding members, a second radiation dose adjusting unit that arranges plural wedge-type radiation attenuating members, the number of which is equal to the number of the detecting elements, in the longitudinal direction of the radiation fan beam and adjusts a radiation attenuation rate at plural points in the longitudinal direction of the radiation fan beam by displacement of the plural wedge-type radiation attenuating members, and a radiation dose control unit that controls an operation of at least one of the first radiation dose adjusting unit and the second radiation dose adjusting unit on the basis of the detection signal from the transmitted radiation dose detecting unit and changes and adjusts the dose of radiation of the radiation fan beam irradiated onto the object.

JP-A No. 11-142597 discloses a movable compensation filter device that has a compensation filter capable of being used in plural imaging parts. The movable compensation filter device includes two compensation filter pieces and a filter moving unit to support the compensation filter pieces and move the compensation filter pieces in parallel. In the movable compensation filter device, each of the compensation filer pieces has a flat shape and is made of an X-ray absorbing material in which the thickness thereof varies depending on place. A combination of a left part and a right part or a combination of the right part and the left part of each of the two compensation filter pieces constitute one compensation filter for a single imaging part.

JP-A No. 2005-27823 discloses an X-ray imaging device for reducing an exposure dose with respect to a subject and imaging a target part and a peripheral region thereof with a desired image that is required for medical treatment and diagnosis to permit observation of the target part and the peripheral region. The X-ray imaging device includes an X-ray generating unit that irradiates X-rays onto the subject, a diaphragm unit that determines an X-ray irradiation field, and an X-ray detecting unit that detects the X-rays irradiated from the X-ray generating unit. An X-ray absorbing filter that absorbs the X-rays is disposed at least one of the X-ray generating unit side or the X-ray detecting unit side of the diaphragm unit, regions where the X-ray dosage and X-ray energy vary are formed in the irradiation field by a function of the X-ray absorbing filter, and image information is obtained by the X-ray detecting unit.

JP-A No. 5-329138 discloses an X-ray scanning device for substantially equalizing a flux of an X-ray fan beam over the entire length of the fan beam. The X-ray scanning device includes an X-ray source that generates the X-ray fan beam and scans an object with the fan beam, a detector including a detector row that detects the X-ray flux transmitted through the object at plural points crossing the fan beam and that is disposed to correspond to the fan beam at an opposite side of the object to output an electric signal indicating the flux detected at the plural points, an X-ray flux modulator that uses a wedge-type shutter which modulates the flux density of the fan beam at the plural points crossing the fan beam, and a feedback circuit that controls the modulator on the basis of the output signal of the detector row to modulate the flux of the fan beam at the plural points crossing the fan beam, and causes the flux of the fan beam detected by the detector row to be substantially equalized over the entire length of the fan beam.

JP-A No. 2005-198762 discloses an X-ray diagnostic device which includes an X-ray generating unit that irradiates X-rays onto a subject, an X-ray detecting unit that detects X-rays irradiated by the X-ray generating unit and transmitted through the subject, an image data generating unit that generates X-ray image data concerning the subject on the basis of the X-rays detected by the X-ray detecting unit, a display unit that displays the generated X-ray image data, a dose detecting unit that detects a radiation dose of the X-rays irradiated from the X-ray generating unit, an irradiation dose calculating unit that calculates an irradiation dose for the subject on the basis of the radiation dose detected by the dose detecting unit, an irradiation dose comparing unit that compares the irradiation dose calculated by the irradiation dose calculating unit and a predetermined allowable irradiation dose, and a dose control unit that controls the radiation dose of the X-rays by the X-ray generating unit on the basis of the comparison result obtained by the irradiation dose comparing unit.

JP-A No. 2001-17416 discloses an imaging device which includes an imaging unit that captures an image of a subject by radiation and acquires image information on the subject, a setting unit that sets information on a kind of a generation source of the image information obtained by the imaging unit, an attribute of the subject, and an imaging part of the subject, a reducing amount determining unit that determines the reducing amount of radiation on the basis of the information set by the setting unit, and a reducing control unit that controls reducing of the radiation on the basis of the reducing amount determined by the reducing amount determining unit.

JP-A No. 2008-119195 discloses an X-ray imaging device which includes an X-ray generator that intermittently irradiates X-rays onto a subject and an X-ray detector that acquires image data according to an incidence dose of the X-rays transmitted through the subject. The X-ray imaging device includes a dose control unit that controls the irradiation dose of the X-rays to the subject and controls the X-ray irradiation so as to repeat a combined irradiation pattern of irradiation with a regular dose and irradiation with a dose smaller than the regular dose.

JP-A No. 2008-272381 discloses an X-ray imaging device which includes an estimation unit that estimates a cumulative exposure dose of X-rays irradiated onto an object, a remaining exposure tolerance dose calculating unit that calculates a remaining exposure tolerance dose using a difference between a tolerated maximum exposure dose and the cumulative exposure dose, an X-ray irradiation tolerance time calculating unit that calculates an X-ray irradiation tolerance time using a difference between a predetermined X-ray irradiation scheduled time and an actual irradiation time of X-rays irradiated onto the object, an X-ray irradiation reference dose calculating unit that calculates an X-ray irradiation reference dose per unit time that is a reference of X-ray irradiation, on the basis of the remaining exposure tolerance dose and the X-ray irradiation tolerance time, and a control unit that controls X-ray irradiation on the object by setting an X-ray irradiation dose per unit time within the X-ray irradiation tolerance time, on the basis of the X-ray irradiation reference dose.

JP-A No. 2009-160308 discloses a radiation treatment system which includes an irradiating unit that irradiates a treatment radiation beam according to an irradiation plan that determines an irradiation condition of radiation on the basis of a reference dose absorbed by a treatment part and a normal part of a subject, a detecting unit that detects scattered rays generated on the basis of the treatment radiation beam, an acquiring unit that acquires data of an absorbed dose from data of the detected scattered rays, a calculating unit that calculates a dose distribution including irradiation and non-irradiation on the basis of the absorbed dose data and the irradiation plan, an evaluating unit that evaluates whether the irradiation plan is appropriate or not using a predetermined evaluation reference on the basis of the absorbed dose data, and a providing unit that provides the dose distribution and the evaluation result.

JP-A Nos. 2007-97909 and 2009-213905 disclose a radiation exposure dose managing system in which a radiation inspecting device, an image managing server, an exposure dose managing device, and an in-hospital information database server are connected to one another via a network. The image managing server holds images of parts of a body of a subject captured by the radiation inspecting device and an image information group including a variety of information related to capturing of the images. The exposure dose managing device manages data of an exposure dose with respect to the subject when the image is captured by the radiation inspecting device. The in-hospital information database server manages personal information of the subject. In the radiation exposure dose managing system, the exposure dose managing device has a function of extracting information, which is necessary to calculate the exposure dose, from the image information group held in the image managing server, and calculating the exposure dose on the basis of the extracted information. In addition, the data of the exposure dose that is calculated by the exposure dose managing device is transmitted to the in-hospital information database through the network and is recorded and stored in a personal information database for the subjects in the in-hospital information database.

SUMMARY OF THE INVENTION

The present invention has been made in view of the above circumstances and provides a radiation image capturing device and a radiation image capturing system.

According to an aspect of the invention, there is provided a radiation image capturing device including: a radiation image capturing unit that captures a radiation image based on radiation which is emitted from a radiation source and which is transmitted through a subject; a diaphragm unit that is provided between the radiation source and the subject, wherein the diaphragm unit has an opening region which is configured to transmit a part of the radiation emitted from the radiation source and whose area is changeable, and wherein the diaphragm unit is configured such that a transmission dose of the radiation decreases as a distance from a circumferential part of the opening region increases; and a control unit that controls the diaphragm unit such that direct rays of the radiation are irradiated onto a predetermined region of the subject.

BRIEF DESCRIPTION OF THE DRAWINGS

Preferred exemplary embodiments of the present invention will be described in detail based on the following figures, wherein:

FIG. 10 is a schematic view illustrating an example of data configuration of exposure dose threshold value information according to a second exemplary embodiment;

FIG. 14 is a schematic view illustrating an example of data configuration of exposure dose history information according to a fourth exemplary embodiment;

FIG. 15 is a schematic view illustrating an example of data configuration of weight value management information according to the fourth exemplary embodiment;

DETAILED DESCRIPTION OF THE INVENTION

Figure 1:
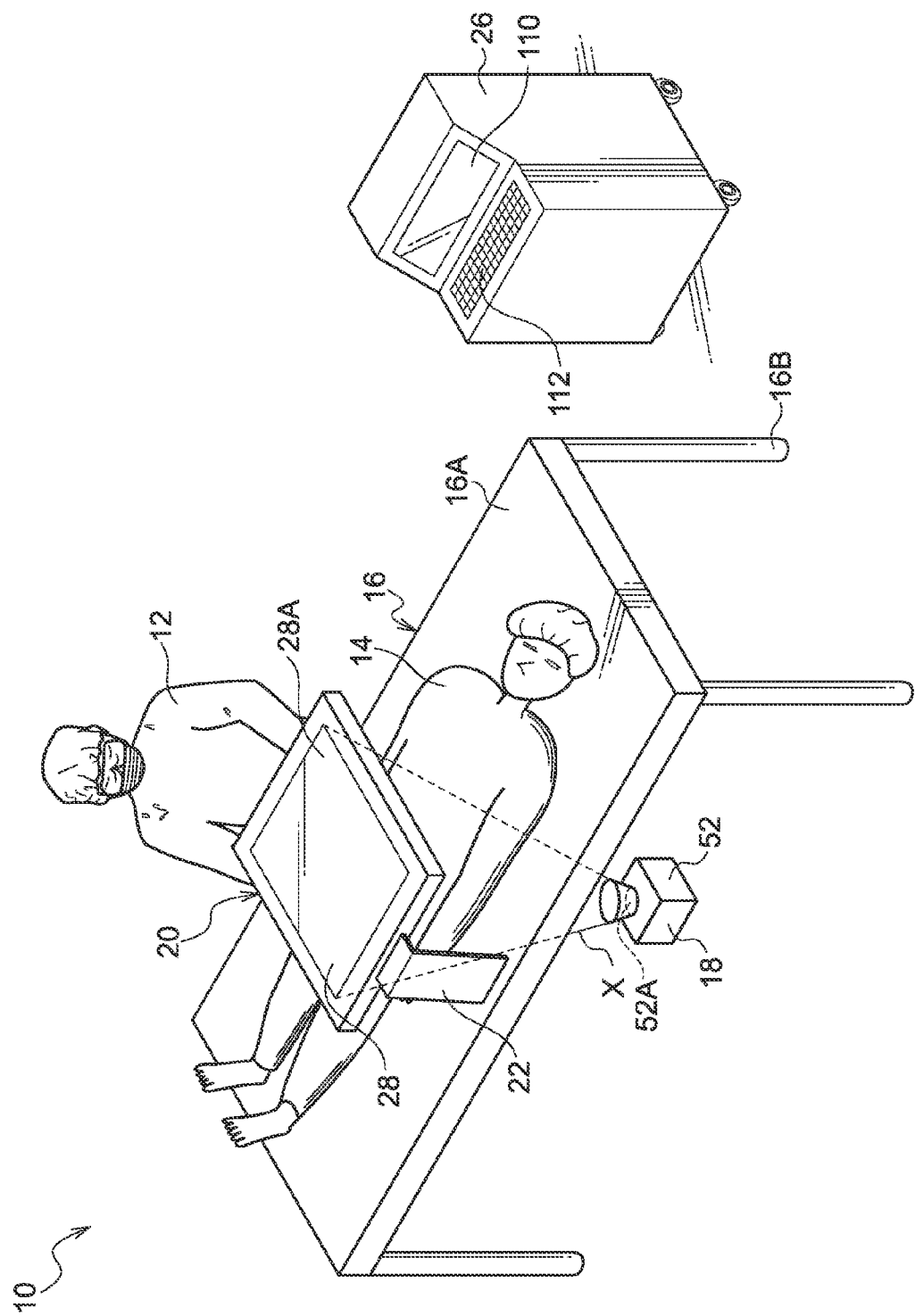
FIG. 1 is a perspective view illustrating an operating room in which a radiation image capturing system according to a first exemplary embodiment is disposed.

The invention will be described.

According to the above technology that is disclosed in JP-A No. 2008-220480, the opening of the radiation source is controlled such that the irradiation region of the radiation is reduced when the radiation image of a position distant from the treatment part is captured and the irradiation region of the radiation is widened when the radiation image of the peripheral part of the treatment part or a complicated part is captured. Therefore, an effect of reducing the exposure dose is limited when the radiation image of the peripheral part of the treatment part or the complicated part is captured.

During execution of IVR, an imaging object region changes with time. Thus, a radiation image of the peripheral part of the region is preferably observed. However, according to the above technology that is disclosed in JP-A No. 2008-220480, since only the radiation image of the region determined by the width of the opening which is previously set is obtained, the radiation image of the peripheral part of the region may not be observed.

According to the above technology that is disclosed in JP-A No. 5-161639, the quality of the radiation image is improved by changing the thickness of a collimator according to the imaging part to change the quality (transmission energy) of radiation. However, since reduction of the exposure is not taken into account, an effect of reducing the exposure dose may not be expected and the radiation image of the peripheral part of the imaging object region may not be observed.

Likewise, even in the above technologies that are disclosed in JP-A Nos. 11-142597 and 5-329138, since reduction of the exposure dose is not taken into account, an effect of reducing the exposure dose may not be expected.

Meanwhile, in the above technology that is disclosed in JP-A No. 2005-27823, the exposure dose may be reduced. However, the radiation image of the peripheral part of the imaging object region may not be observed.

The invention provides a radiation image capturing device and a radiation image capturing system that may allow a radiation image of a peripheral part of an imaging object region to be observed, while an exposure dose with respect to a subject may be suppressed.

According to the above technologies that are disclosed in JP-A Nos. 2005-198762, 2001-17416, 2008-119195, and 2008-272381, the exposure dose with respect to a patient may be reduced. However, since an exposure dose with respect to a region of interest is also reduced, a quality of a radiation image of the region of interest is degraded.

The invention provides a radiation control device and a radiation image capturing system that may suppress an exposure dose with respect to a subject, while preventing degradation of a quality of a radiation image in a region of interest.

In the above technologies that are disclosed in Japanese Patent Application Laid-Open (JP-A) Nos. 2009-160308, 2007-97909, and 2009-213905, since the exposure dose is managed according to the parts of a human body such as the heart, the large intestine, the chest, and the cervical spine, the exposure dose with respect to the subject cannot necessarily be effectively reduced.

That is, a radiation image needs to be captured with respect to at least a region of interest by a technician. Meanwhile, when the IVR is executed, the irradiation field where the radiation is exposed continuously changes every moment, since the region of interest changes according to the insertion state of the catheter into the body. Therefore, as in the conventional technologies described above, even if the exposure dose is managed according to the parts of the human body, it is difficult to grasp the past exposure dose with respect to the irradiation field that changes every moment with high precision.

The invention provides a radiographic imaging management device and a radiation image capturing system that may effectively prevent excessive exposure of the radiation with respect to the subject.

Hereinafter, exemplary embodiments of the invention will be described in detail with reference to the drawings.

First Exemplary Embodiment

First, the configuration of a radiation image capturing system (hereinafter, simply referred to as "imaging system") 10 according to this exemplary embodiment will be described with reference to FIG. 1.

As shown in FIG. 1, the imaging system 10 according to this exemplary embodiment captures a radiation image by an operation of a medical doctor 12 or a radiation technician. The imaging system 10 includes a bed 16 where a patient 14 lies, a radiation irradiating device 18 that irradiates radiation X of a radiation dose according to predetermined imaging conditions onto the patient 14, a portable imaging device 20 (hereinafter, referred to as "electronic cassette") that detects the radiation X transmitted through the patient 14, generates radiation image information (hereinafter, simply referred to as "image information") indicating a radiation image according to the dose of detected radiation, and stores the image information in a predetermined storage area, thereby completing capturing of an image, a support member 22 that is provided in the bed 16 and cantilever-supports the electronic cassette 20 at a side of the bed 16 where the patient 14 lies, and a console 26 that controls the radiation irradiating device 18 and the electronic cassette 20.

The bed 16 is made of a material that transmits the radiation X, and includes an object table 16A on which the patient 14 lies. The object table 16A has substantially a rectangular flat shape. Four corners of the object table 16A are provided with legs 16B, respectively so that the object table 16A is supported.

In this case, the radiation irradiating device 18 is disposed on the back side of the object table 16A, such that the radiation X is irradiated onto the patient 14 on the object table 16A from the back side (that is, the side opposite to the side where the patient 14 lies with his or her head back) of the object table 16A.

Meanwhile, the electronic cassette 20 according to this exemplary embodiment includes a display 28, on which the captured radiation image is displayed, on the back surface thereof, and the electronic cassette 20 is disposed on the surface side (the side where the patient 14 lies) of the object table 16A, such that the radiation X irradiated from the radiation irradiating device 18 transmits the object table 16A and the patient 14 and is detected by a radiation detector 36 to be described below, in a state where a display surface 28A of the display 28 is an upward surface.

On a surface of the side of the object table 16A where the patient 14 lies, the support member 22 is provided. The support member 22 is bent in substantially an L shape. A base end of the support member 22 is fixed to the object table 16A and a distal end thereof is removably mounted with the electronic cassette 20.

Figure 2:
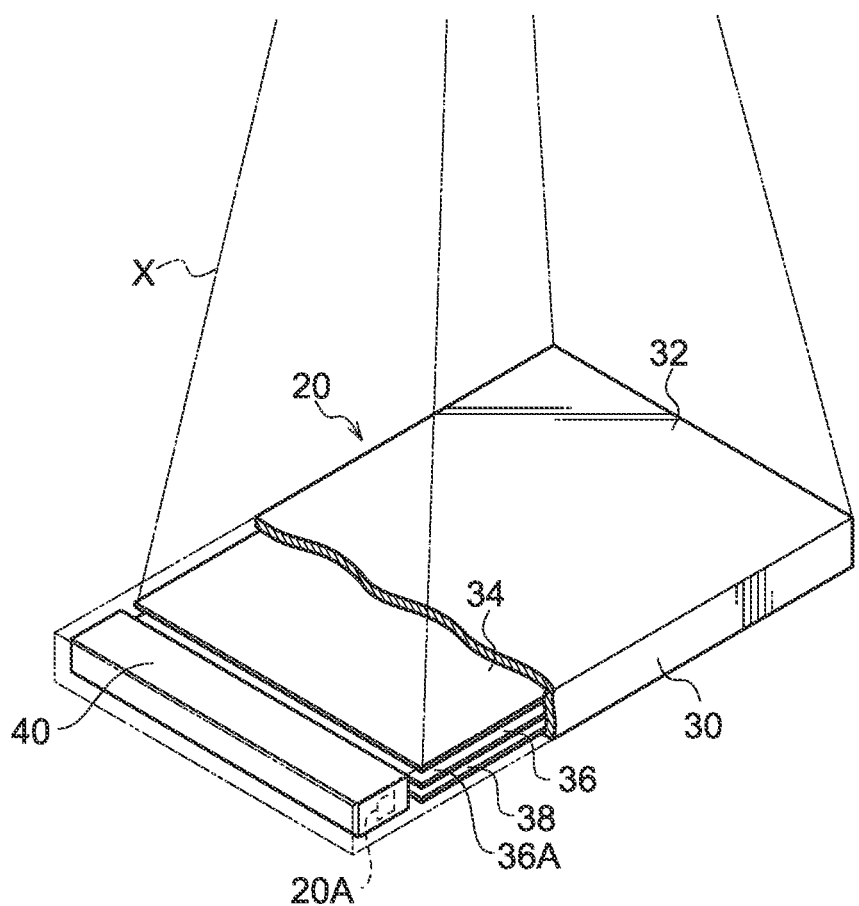
FIG. 2 is a partially fractured perspective view illustrating the internal configuration of an electronic cassette according to the first exemplary embodiment.

FIG. 2 shows the internal configuration of the electronic cassette 20 according to this exemplary embodiment.

As shown in FIG. 2, the electronic cassette 20 includes a casing 30 that is formed of a material transmitting the radiation X and has an approximately rectangular flat shape. To the electronic cassette 20, blood or various germs may be attached, in a case in which the electronic cassette 20 is used in an operating room. The casing 30 is configured to have a waterproof property and a sealing property, thereby, one electronic cassette 20 may be repetitively used by performing antiseptic wash, according to necessity.

On the side of the casing 30 of the electronic cassette 20, a connecting terminal 20A that connects a communication cable is provided. In the casing 30, a grid 34, a radiation detector 36, and a lead plate 38 are sequentially disposed. The grid 34 removes scattered rays of the radiation X from the side of the irradiation surface 32 of the casing 30 where the radiation X is irradiated. The radiation detector 36 is disposed on the opposite side of the display surface 28A to be oriented in an opposite direction of the display surface 28A of the display 28, includes an irradiation surface 36A with an approximately rectangular shape on which the radiation X is irradiated, detects a radiation dose of the radiation X that is transmitted through the patient 14 and that is irradiated from the irradiation surface 36A, and outputs image information that indicates a radiation image according to the radiation dose. The lead plate 38 is interposed between the display 28 and the radiation detector 36 and absorbs back scattered rays of the radiation X.

On the side of one end of an inner part of the casing 30, a case 40 that accommodates an electronic circuit including a microcomputer and a chargeable secondary battery is disposed. The radiation detector 36 and the electronic circuit are operated by power supplied from the secondary battery accommodated in the case 40. In this case, a shielding member, such as the lead plate, which shields the radiation, is preferably disposed on the side of the irradiation surface 32 of the case 40 to prevent the various circuits accommodated in the case 40 from being damaged by irradiation of the radiation X.

Figure 3:
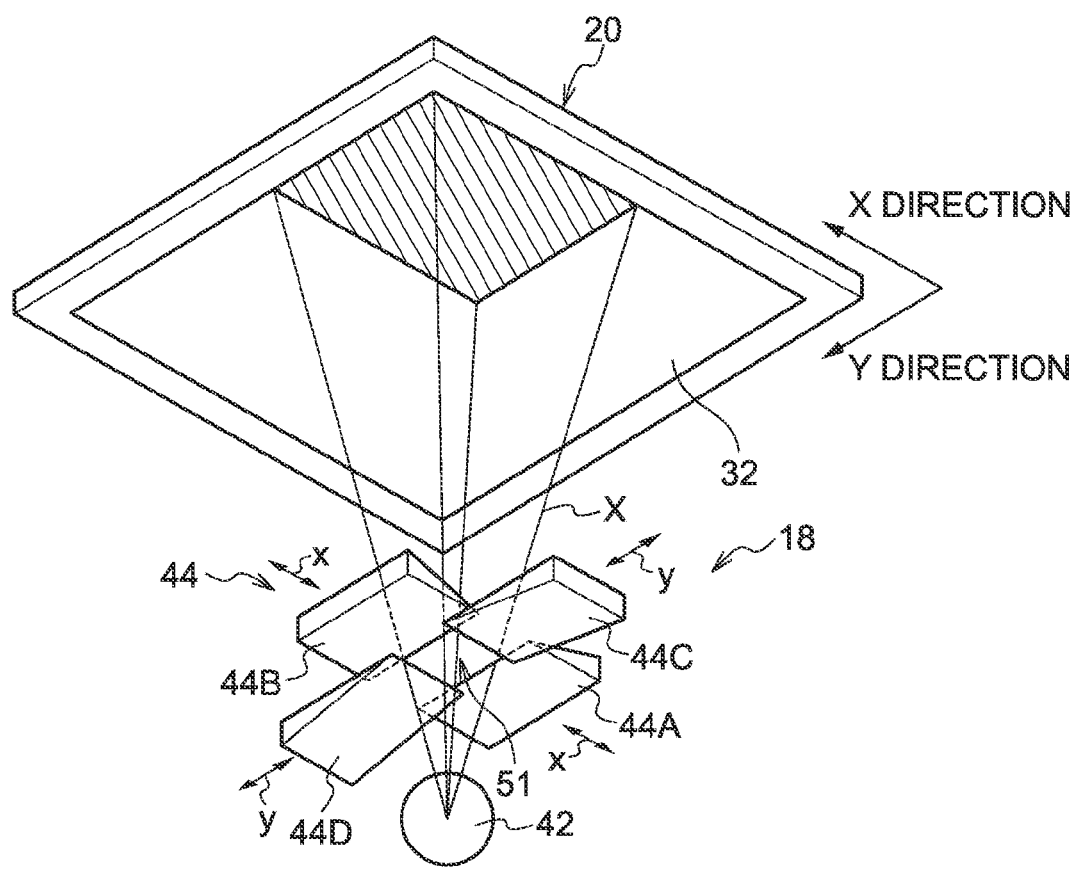
FIG. 3 is a perspective view illustrating the configuration of a main part of a radiation irradiating device according to the first exemplary embodiment.

FIG. 3 is a perspective view illustrating the configuration of a main part of the radiation irradiating device 18 according to this exemplary embodiment.

As shown in FIG. 3, the radiation irradiating device 18 includes a radiation source 42 that emits the radiation X and a diaphragm unit 44 that is provided between the radiation source 42 and the electronic cassette 20 and that includes four slit plates 44A, 44B, 44C, and 44D.

Each of the slit plates 44A to 44D is composed of a flat member that is made of a material that shields the radiation X such as lead or tungsten, that is rectangular in plan view and that has a thickness that gradually increases in a height direction from a tip end to a rear end. In the diaphragm unit 44, the slit plates 44A to 44D are disposed such that the tip ends of the slit plates 44A and 44B face each other, the tip ends of the slit plates 44C and 44D face each other, and an opening region 51 having a rectangular shape in plan view is formed by the tip ends of the slit plates 44A to 44D.

In this case, the slit plates 44A and 44B are configured to be movable in an x direction in FIG. 3. Meanwhile, the slit plates 44C and 44D are configured to be movable in a y direction orthogonal to the x direction in FIG. 3. In the diaphragm unit 44 according to this exemplary embodiment, a movable range of each of the slit plates 44A to 44D is a range from a state where the tip ends of the slit plates disposed to face each other contact each other, that is, a range from a state where the opening region 51 is fully closed to a state where the opening region 51 holds a rectangular shape in plan view and has the maximum area (hereinafter, referred to as "fully open state").

In the radiation irradiating device 18 according to this exemplary embodiment, the slit plate 44A is moved by driving power of a motor 146 (see FIG. 5) that is transmitted through a transmitting unit (not shown in the drawings), the slit plate 44B is moved by driving power of a motor 148 (see FIG. 5) that is transmitted through a transmitting unit (not shown in the drawings), the slit plate 44C is moved by driving power of a motor 150 (see FIG. 5) that is transmitted through a transmitting unit (not shown in the drawings), and the slit plate 44D is moved by driving power of a motor 152 (see FIG. 5) that is transmitted through a transmitting unit (not shown in the drawings).

Meanwhile, as shown in FIG. 1, the radiation irradiating device 18 according to this exemplary embodiment is made of a material that shields the radiation X such as lead or tungsten, and includes an accommodating box 52 that accommodates the radiation source 42 and the diaphragm unit 44 therein. As shown in FIG. 1, the accommodating box 52 has an opening 52A that is used to irradiate the radiation X emitted from the radiation source 42 and transmitted through the diaphragm unit 44 onto the irradiation surface 32 of the electronic cassette 20.

In this case, the opening 52A has a size that is sufficient to satisfy the condition that direct rays of the radiation X transmitted through the opening region 51 when the slit plates 44A to 44D in the diaphragm unit 44 are fully opened and the radiation X (hereinafter, referred to as "transmission rays") transmitted with a transmission dose according to the thickness of the slit plates 44A to 44D can be calculated.

In the imaging system 10 according to this exemplary embodiment, the electronic cassette 20 and the radiation irradiating device 18 are previously positioned such that the radiation X is irradiated onto the entire surface of the irradiation surface 32 in the electronic cassette 20, in a case in which the slit plates 44A to 44D of the diaphragm unit 44 are fully opened.

Figure 4:
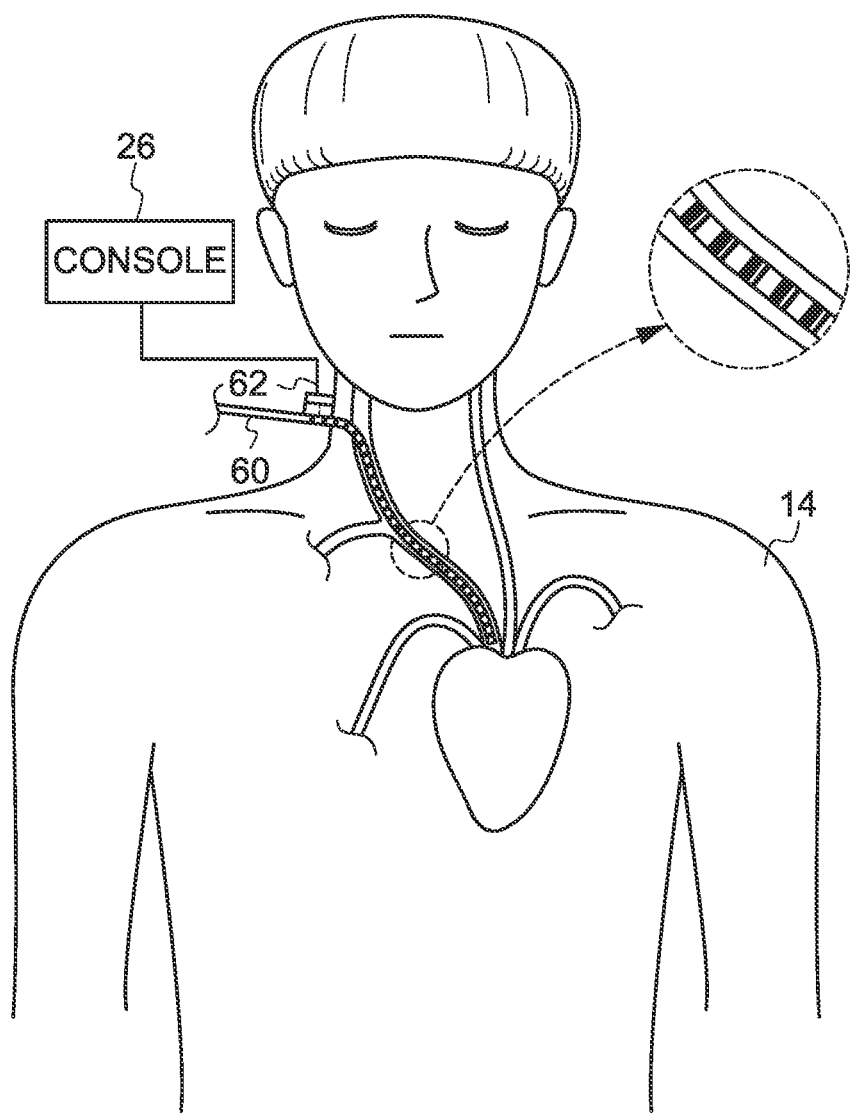
FIG. 4 is a schematic view illustrating an aspect of the case where IVR according to the first exemplary embodiment is executed.

Meanwhile, FIG. 4 is a schematic view illustrating an example of an aspect of the case where IVR is executed with respect to the patient 14.

As shown in FIG. 4, a catheter 60 is used for the IVR. On the surface of the catheter 60 according to this exemplary embodiment, a black-and-white striped pattern is provided along a longitudinal direction. In this case, in the black-and-white striped pattern, plural groups, each of which includes a wide black region, a narrow white region, a narrow black region, and a wide white region, are continuously provided in the longitudinal direction.

Meanwhile, on the skin of the patient 14 that is near an insertion opening of the catheter 60, a reflective photo sensor 62 that irradiates rays onto the surface of the catheter 60 inserted into the insertion opening and receives reflected light of the rays is provided. The reflective photo sensor 62 receives the reflected light from the surface of the catheter 60, converts the received light into an electric signal, and transmits the electric signal to the console 26.

Next, the configuration of a main part of an electric system of the imaging system 10 according to this exemplary embodiment will be described with reference to FIG. 5.

Figure 5:
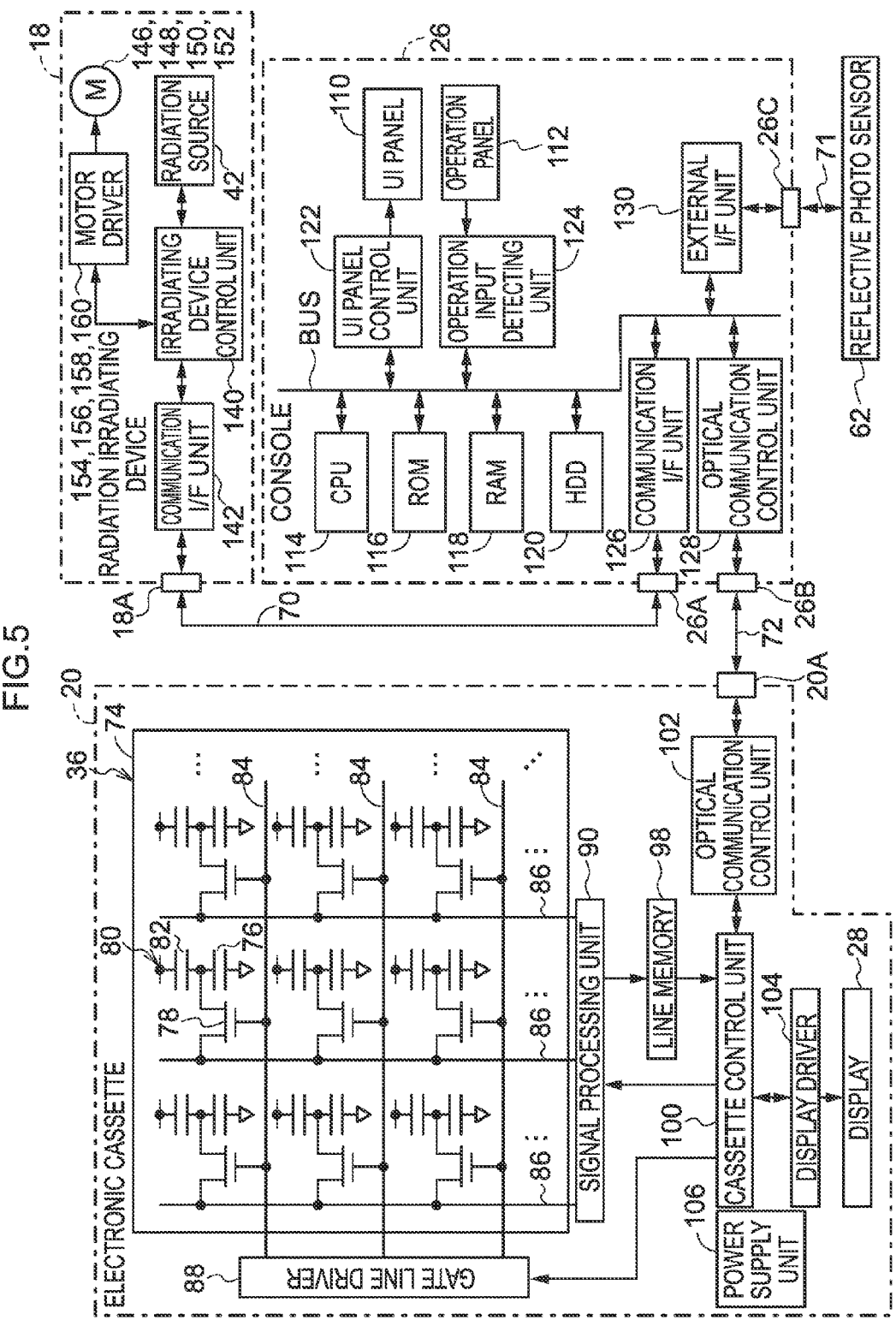
FIG. 5 is a block diagram illustrating the configuration of the radiation image capturing system according to the first exemplary embodiment.

As shown in FIG. 5, in the radiation irradiating device 18 according to this exemplary embodiment, a connecting terminal 18A that is used to communicate with the console 26 is provided. In the console 26 according to this exemplary embodiment, a connecting terminal 26A that is used to communicate with the radiation irradiating device 18, a connecting terminal 26B that is used to communicate with the electronic cassette 20, and a connecting terminal 26C that is used to receive an electric signal from the reflective photo sensor 62 are provided.

The radiation irradiating device 18 is connected to the console 26 through a communication cable 70. The reflective photo sensor 62 is connected to the console 26 through the communication cable 71. When the radiation image is captured, the communication cable 72 is connected to the connecting terminal 20A of the electronic cassette 20, and the electronic cassette 20 is connected to the console 26 through the communication cable 72. In this exemplary embodiment, an optical communication cable that employs an optical fiber in the communication cable 72 is used to enable high-speed data transmission between the electronic cassette 20 and the console 26, and data is transmitted between the electronic cassette 20 and the console 26 by optical communication.

The radiation detector 36 that is incorporated in the electronic cassette 20 may be an indirect conversion type that coverts radiation into light using a scintillator and then converts the light into charge using a photoelectric conversion element such as a photodiode, or a direct conversion type that converts radiation into charge using a semiconductor layer such as an amorphous selenium layer. The radiation detector 36 of the direct conversion type is configured such that a photoelectric conversion layer, which absorbs the X-rays and converts the X-rays into an electric charge, is laminated on a Thin Film Transistor (TFT) active matrix substrate 74. The photoelectric conversion layer is made of amorphous selenium (a-Se) using selenium as a principal component (for example, the content of 50% or more). If the radiation X is irradiated, the photoelectric conversion layer internally generates charge carriers (electronic-hole pairs) in an amount that depends on the irradiated radiation dose and converts the irradiated radiation X into the electric charge. The radiation detector 36 of the indirect conversion type may indirectly convert the irradiated radiation X into electric charge using a phosphor material and a photoelectric conversion element (photodiode), instead of a radiation-charge conversion material, such as the amorphous selenium, which directly converts the radiation X into electric charge. As the phosphor materials, gadolinium oxysulfide (GOS) and cesium iodide (CsI) are well-known. In this case, the radiation is converted into light by the phosphor material and the light is converted into electric charge by the photodiode of the photoelectric conversion element. The electronic cassette of the present embodiment is provided with the radiation detector 36 of the indirect conversion type.

On the TFT active matrix substrate 74, plural pixel portions 80 (in FIG. 5, the photoelectric conversion layer or the photoelectric conversion element corresponding to each pixel portion 80 is schematically illustrated as a photoelectric conversion unit 82), each of which includes a storage capacitor 76 that accumulates the electric charge generated in the photoelectric conversion layer and a TFT 78 that reads the electric charge accumulated in the storage capacitor 76, are arranged in a matrix. The electric charge that is generated in the photoelectric conversion layer by irradiation of the radiation X onto the electronic cassette 20 is accumulated in the storage capacitor 76 of each pixel portion 80. Thereby, image information that is carried in the radiation X irradiated onto the electric catheter 20 is converted into charge information and is held in the radiation detector 36.

On the TFT active matrix substrate 74, plural gate lines 84 that extend in a constant direction (row direction) and that are used to turn on/off the TFT of each pixel portion 80 and plural data lines 86 that extend in a direction (column direction) orthogonal to the gate lines 84 and that are used to read the accumulated electric charge from the storage capacitor 76 through the turned-on TFT 78 are provided. Each gate line 84 is connected to a gate line driver 88 and each data line 86 is connected to a signal processing unit 90. If the electric charge is accumulated in the storage capacitor 76 of each pixel portion 80, the TFT 78 of each pixel portion 80 is sequentially turned on row by row by a signal supplied from the gate line driver 88 through the gate line 84. The electric charge that is accumulated in the storage capacitor 76 of the pixel portion 80 where the TFT 78 is turned on is transmitted as a charge signal through the data line 86 and the signal is input to a signal processing unit 90. Accordingly, the electric charge that is accumulated in the storage capacitor 76 of each pixel portion 80 is sequentially read row by row.

Figure 6:
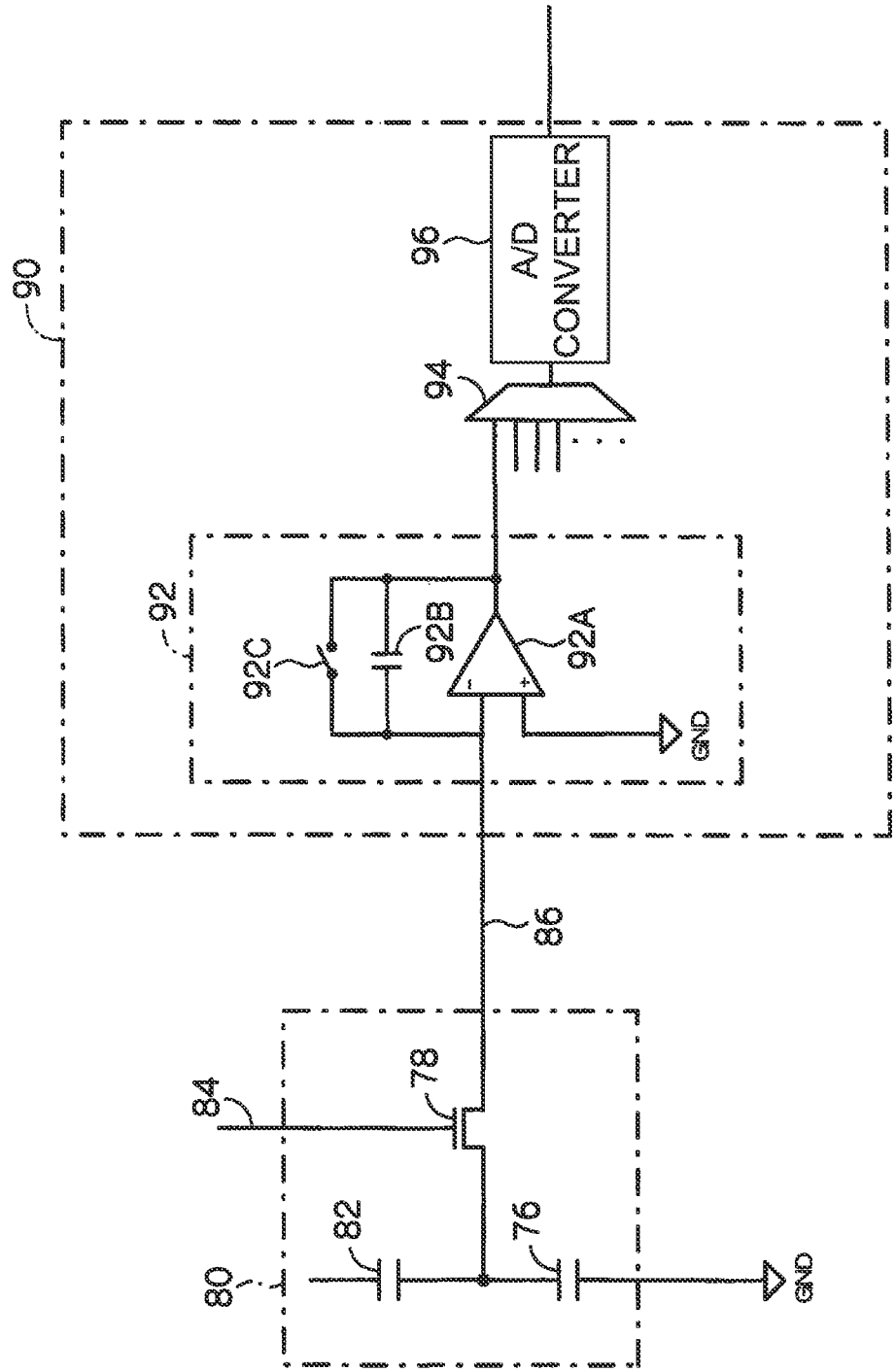
FIG. 6 is an equivalent circuit diagram illustrating one pixel portion of a radiation detector according to the first exemplary embodiment.

FIG. 6 is an equivalent circuit diagram illustrating one pixel of the radiation detector 36 according to this exemplary embodiment.

As shown in FIG. 6, a source of the TFT 78 is connected to the data line 86 and the data line 86 is connected to the signal processing unit 90. A drain of the TFT 78 is connected to the storage capacitor 76 and the photoelectric conversion unit 82 and a gate of the TFT 78 is connected to the gate line 84.

The signal processing unit 90 includes a sample hold circuit 92 that is provided for each data line 86. The charge signal that is transmitted through each data line 86 is held in the sample hold circuit 92. The sample hold circuit 92 is configured to include an operational amplifier 92A and a capacitor 92, and converts the charge signal into an analog voltage. In the sample hold circuit 92, a switch 92C functioning as a reset circuit that short-circuits electrodes of the capacitor 92B and discharges the electric charge accumulated in the capacitor 92B is provided.

A multiplexer 94 and an analog/digital (A/D) converter 96 are sequentially connected to the output side of the sample hold circuit 92, and the charge signal that is held in each sample hold circuit is converted into an analog voltage, the analog voltage is sequentially (serially) input to the multiplexer 94 and is converted into digital image information by the A/D converter 96.

As shown in FIG. 5, a line memory 98 is connected to the signal processing unit 90 and the image information that is output from the A/D converter 96 of the signal processing unit 90 is sequentially stored in the line memory 98. The line memory 98 has a storage capacity that may store image information indicating the radiation image by the amount corresponding to a given number of lines, and read image information corresponding to one line is sequentially stored in the line memory 98, whenever the electric charge is read for each line.

The line memory 98 is connected to a cassette control unit 100 to control the overall operation of the electronic cassette 20. The cassette control unit 100 is realized by a microcomputer, and an optical communication control unit 102 is connected to the cassette control unit 100. The optical communication control unit 102 is connected to the connecting terminal 102A and controls transmission of a variety of information between an external apparatus connected through the connecting terminal 20A and the optical communication control unit. Accordingly, the cassette control unit 100 may exchange a variety of information with the external apparatus through the optical communication control unit 102.

The electronic cassette 20 includes a display driver 104 that controls a display operation by the display 28, and the cassette control unit 100 is connected to the display driver 104. The cassette control unit 100 reads image information that is stored in the line memory 98 and displays a radiation image indicated by the image information on a display surface 28A of the display 28. On the display 28 according to this exemplary embodiment, the radiation image that is indicated by the image information obtained by the radiation detector 36 is displayed with a substantially actual size.

The electronic cassette 20 includes a power supply unit 106. The various circuits or elements (the gate line driver 88, the signal processing unit 90, the line memory 98, the optical communication control unit 102 or the microcomputer functioning as the cassette control unit 100) are operated by the power supplied from the power supply unit 106. The power supply unit 106 incorporates a battery (rechargeable secondary battery) to ensure portability of the electronic cassette 20, and supplies power from the charged battery to the various circuits or elements.

Meanwhile, the console 26 is configured as a server computer and includes a User Interface (UI) panel 10 and an operation panel 112 (see also FIG. 1). The UI panel 110 is configured with using a touch panel display and etc. where a transmissive touch panel overlaps a display, in the UI panel 10, operation menus or various kinds of information such as the captured radiation images are displayed on a display surface of the display and desired information or instruction is input in a case in which a user contacts the touch panel with a touch pen. The operation panel 112 includes plural keys and receives various information or operation instructions.

The console 26 includes a Central Processing Unit (CPU) 114 that performs the overall operation of the device, a Read Only Memory (ROM) 116 that previously stores various programs including a control program, a Random Access Memory (RAM) 118 that temporarily stores various kinds of data, and a Hard Disk Drive (HDD) 120 that stores and holds various kinds of data.

The console 26 includes a UI panel control unit 122, an operation input detecting unit 124, a communication interface (I/F) unit 126, an optical communication control unit 128, an external I/F unit 130. The UI panel control unit 122 controls the display of the UI panel 110 and detects an operation state with respect to the touch panel. The operation input detecting unit 124 detects an operation state with respect to the operation panel 112. The communication interface (I/F) unit 126 is connected to the connecting terminal 26A and exchanges a variety of information such as exposure conditions and state information of the radiation irradiating device 18 with the radiation irradiating device 18 through the connecting terminal 26A and the communication cable 70. The optical communication control unit 128 is connected to the connecting terminal 26B and exchanges a variety of information such as image information with the electronic cassette 20 through the connecting terminal 26B and the communication cable 72. The external I/F unit 130 is connected to the connecting terminal 26C and receives an electric signal from the reflective photo sensor 62 through the connecting terminal 26C and the communication cable 71.

The CPU 114, ROM 116, RAM 118, HDD 120, UI panel 122, operation input detecting unit 124, communication I/F unit 126, optical communication control unit 128, and external I/F unit 130 are connected to each other through a system bus BUS. Therefore, the CPU 114 may have access to the ROM 116, RAM 118, and HDD 120, and thus it may control display of a variety of information on the display of the UI panel 110 through the UI panel control unit 122, grasp an operation state of the user with respect to the touch panel of the UI panel 10 through the UI panel control unit 122, grasp an operation state of the user with respect to the operation panel 112 through the operation input detecting unit 124, control an exchange of a variety of information with the radiation irradiating device 18 through the communication I/F unit 126, control an exchange of a variety of information with the electronic cassette 20 through the optical communication control unit 128, and acquire the detection result of the reflective photo sensor 62 through the external I/F unit 130.

The touch panel of the UI panel 110 according to this exemplary embodiment is configured such that plural switches using a transparent electrode are arranged in a matrix. In a state where a radiation image of a patient 14 is displayed on the screen of the display of the UI panel 110, if the user contacts the screen of the display of the UI panel 110 with the touch pen (not shown in the drawings), any one of the plural switches of the touch panel is turned on. If any one of the plural switches of the touch panel is turned on, the UI panel control unit 122 outputs coordinate information, which represents the position of the turned-on switch with a two-dimensional orthogonal coordinate system in the matrix, to the CPU 114. If the CPU 114 receives the coordinate information from the UI panel control unit 122, the CPU 114 stores the coordinate information in the HDD 120.

Meanwhile, the radiation irradiating device 18 includes an irradiating device control unit 140 that controls the entire operation of the radiation irradiating device 18. The irradiating device control unit 140 is realized by the microcomputer, and the communication I/F unit 142 is connected to the irradiating device control unit 140. The communication I/F unit 142 is connected to the connecting terminal 18A and controls transmission of a variety of information with the console 26 connected through the connecting terminal 18A. Therefore, the irradiating device control unit 140 may exchange a variety of information with the console 26 through the communication I/F unit 142. The radiation source 42 is connected to the irradiating device control unit 140 and the irradiating device control unit 140 controls the radiation source 42 on the basis of the exposure conditions received through the communication I/F unit 142.

The radiation irradiating device 18 includes a motor 146 that generates driving force to move the slit plate 44A, a motor 148 that generates driving force to move the slit plate 44B, a motor 150 that generates driving force to move the slit plate 44C, and a motor 152 that generates driving force to move the slit plate 44D.

The radiation irradiating device 18 includes a motor driver 154 that controls driving of the motor 146, a motor driver 156 that controls driving of the motor 148, a motor driver 158 that controls driving of the motor 150, and a motor driver 160 that controls driving of the motor 152.

The motor 146 is connected to the irradiating device control unit 140 through the motor driver 154, the motor 148 is connected to the irradiating device control unit 140 through the motor driver 156, the motor 150 is connected to the irradiating device control unit 140 through the motor driver 158, and the motor 152 is connected to the irradiating device control unit 140 through the motor driver 160. Therefore, the driving of the motors 146, 148, 150, and 152 is controlled by the irradiating device control unit 40 according to an instruction from the console 26.

Next, the structure of the indirect-conversion-type radiation detector 36 that indirectly converts radiation into charge using a phosphor material and a photoelectric conversion element will be described.

Figure 23:
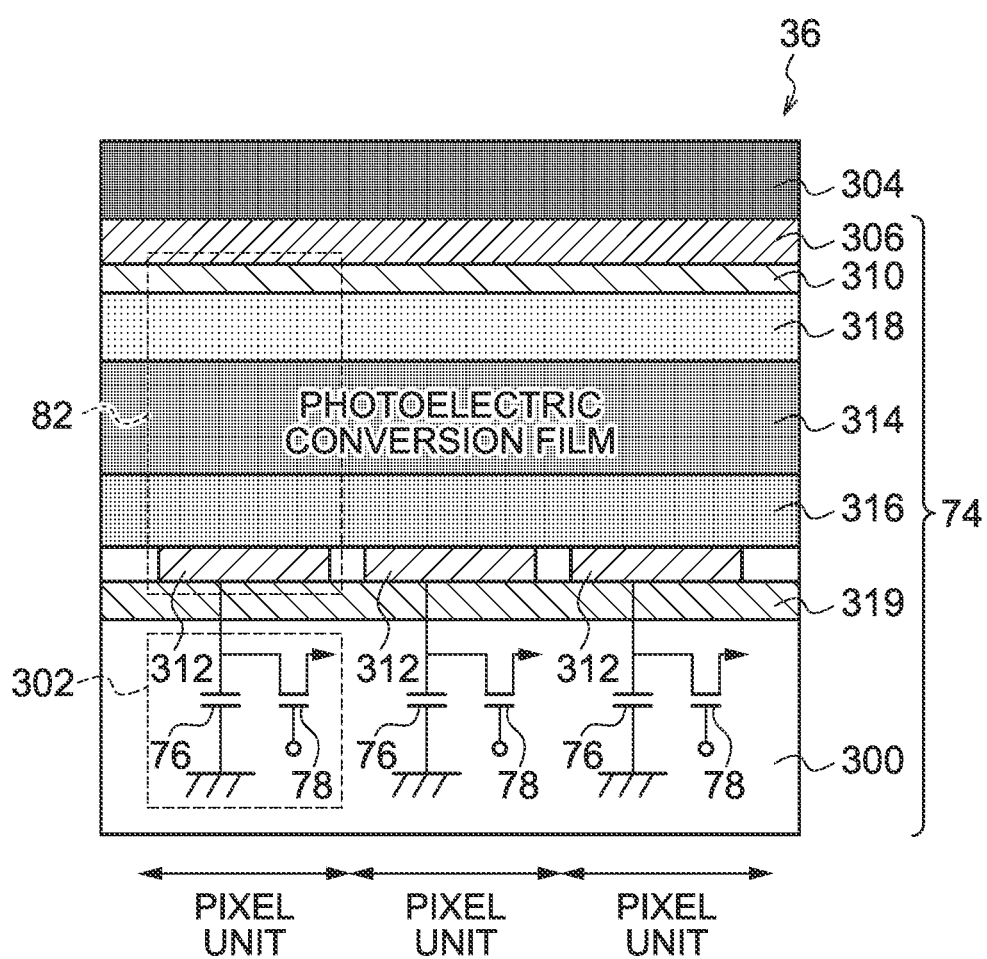
FIG. 23 is a cross-sectional view schematically illustrating a structure of an indirect conversion type radiation detector of according to the embodiment.

FIG. 23 is a cross-sectional view schematically illustrating the structure of three pixel units of the indirect-conversion-type radiation detector 36 according to an embodiment of the invention.

The radiation detector 36 includes a signal output unit 302, a photoelectric conversion unit 82, and a scintillator 304 that are sequentially laminated on an insulating substrate 300. The signal output unit 302 and the photoelectric conversion unit 82 form a pixel unit. Plural pixel units are arranged on the substrate 300. In each pixel unit, the signal output unit 302 and the photoelectric conversion unit 82 are arranged so as to overlap each other.

The scintillator 304 is formed on the photoelectric conversion unit 82 with a transparent insulating film 306 interposed therebetween, and has a phosphor film that converts radiation incident from the upper side (the side opposite to the substrate 300) into light and emits the light. The provision of the scintillator 304 makes it possible to absorb radiation passing through the object and emit light.

It is preferable that the wavelength range of light emitted by the scintillator 304 be a visible light range (wavelength of 360 nm to 830 nm). It is more preferable that the wavelength range of light include a green wavelength range in order to capture a monochromatic image using the radiation detector 36.

Specifically, in a case in which imaging is performed using X-rays as radiation, it is preferable that the phosphor used for the scintillator 304 include cesium iodide (CsI). It is more preferable to use CsI(Tl) having an emission spectrum of 420 nm to 600 nm during the emission of X-rays. The emission peak wavelength of CsI(Tl) in the visible light range is 565 nm.

In a case in which the scintillator 304 is made of a columnar crystal, such as CsI(Tl), it may be formed on a vapor deposition substrate by vapor deposition. As such, in a case in which the scintillator 304 is formed by vapor deposition, an Al plate is generally used as the vapor deposition substrate in terms of the transmittance of X-rays and manufacturing costs, but the vapor deposition substrate is not limited to the Al plate. In a case in which GOS is used as the scintillator 304, GOS may be applied onto the surface of a TFT active matrix substrate 74 to form the scintillator 304, without using the vapor deposition substrate.

The photoelectric conversion unit 82 includes an upper electrode 310, a lower electrode 312, and a photoelectric conversion film 314 provided between the upper and lower electrodes.

The upper electrode 310 needs to make light generated by the scintillator 304 incident on the photoelectric conversion film 314. Therefore, it is preferable that the upper electrode 310 be made of a conductive material that is at least transparent with respect to the emission wavelength of the scintillator 304. Specifically, it is preferable that the upper electrode 310 be made of a transparent conducting oxide (TCO) having high transmittance with respect to visible light and a small resistance value. A metal thin film, such as an Au thin film, may be used as the upper electrode 310. However, when the transmittance increases to 90% or more, the resistance value is likely to increase. Therefore, it is preferable that the upper electrode 310 be made of TCO. For example, it is preferable that the upper electrode 310 be made of ITO, IZO, AZO, FTO, $SnO_2$, $TiO_2$, or $ZnO_2$. It is most preferable that the upper electrode 310 be made of ITO in terms of a simple process, low resistance, and transparency. One upper electrode 310 may be common to all pixel units, or the upper electrode 310 may be divided for each pixel unit.

The photoelectric conversion film 314 absorbs light emitted from the scintillator 304 and generates a charge corresponding to the absorbed light. The photoelectric conversion film 314 may be made of a material that receives light and generates charge. For example, the photoelectric conversion film 314 may be made of amorphous silicon or an organic photoelectric conversion material. When the photoelectric conversion film 314 includes amorphous silicon, it has a wide absorption spectrum and can absorb light emitted from the scintillator 304. When the photoelectric conversion film 314 includes an organic photoelectric conversion material, it has a narrow absorption spectrum in the visible light range and absorbs little electromagnetic waves other than the light emitted from the scintillator 304. Therefore, it is possible to effectively reduce noise generated due to the absorption of radiation, such as X-rays, by the photoelectric conversion film 314.

It is preferable that the absorption peak wavelength of the organic photoelectric conversion material forming the photoelectric conversion film 314 be close to the emission peak wavelength of the scintillator 304 in order to most effectively absorb light emitted from the scintillator 304. It is ideal that the absorption peak wavelength of the organic photoelectric conversion material is equal to the emission peak wavelength of the scintillator 304. However, when the difference between the absorption peak wavelength and the emission peak wavelength is small, it is possible to sufficiently absorb light emitted from the scintillator 304. Specifically, the difference between the absorption peak wavelength of the organic photoelectric conversion material and the emission peak wavelength of the scintillator 304 with respect to radiation is preferably equal to or less than 10 nm and more preferably, equal to or less than 5 nm.

Examples of the organic photoelectric conversion material capable of satisfying the above-mentioned conditions include a quinacridone-based organic compound and a phthalocyanine-based organic compound. For example, the absorption peak wavelength of quinacridone in the visible light range is 560 nm. Therefore, when quinacridone is used as the organic photoelectric conversion material and CsI(Tl) is used as the material forming the scintillator 304, it is possible to reduce the difference between the peak wavelengths to 5 nm or less and substantially maximize the amount of charge generated by the photoelectric conversion film 314.

Next, the photoelectric conversion film 314 that can be applied to the radiation detector 36 according to this embodiment will be described in detail.

An electromagnetic wave absorption/photoelectric conversion portion of the radiation detector 36 according to the invention may be formed by an organic layer including a pair of the lower electrode 312 and the upper electrode 310 and the organic photoelectric conversion film 314 interposed between the lower electrode 312 and the upper electrode 310. Specifically, the organic layer may be formed by laminating or mixing, for example, an electromagnetic wave absorption portion, a photoelectric conversion portion, an electron transport portion, a hole transport portion, an electron blocking portion, a hole blocking portion, a crystallization prevention portion, an electrode, and an interlayer contact improvement portion.

It is preferable that the organic layer include an organic p-type compound or an organic n-type compound.

The organic p-type semiconductor (compound) is a donor-type organic semiconductor (compound) whose representative example is a hole-transport-type organic compound and means an organic compound which readily donates electrons. Specifically, in a case in which two organic materials are in contact with each other during use, one organic compound with low ionization potential is the organic p-type semiconductor. Therefore, any organic compound may be used as the donor-type organic compound as long as it has an electron donating property.

The organic n-type semiconductor (compound) is an acceptor-type organic semiconductor (compound) whose representative example is an electron-transport-type organic compound and means an organic compound which readily accepts electrons. Specifically, in a case in which two organic compounds are in contact with each other during use, one organic compound with high electron affinity is the organic n-type semiconductor. Therefore, any organic compound may be used as the acceptor-type organic compound as long as it has an electron accepting property.

Materials applicable to the organic p-type semiconductor and the organic n-type semiconductor and the structure of the photoelectric conversion film 314 have been described in detail in JP-A No. 2009-32854 and thus a detailed description thereof will be omitted. The photoelectric conversion film 314 may include fullerene or carbon nanotubes.

It is preferable that the thickness of the photoelectric conversion film 314 be as large as possible in terms of the absorption of light from the scintillator 304. However, when the thickness of the photoelectric conversion film 314 is greater than a predetermined value, the intensity of the electric field of the photoelectric conversion film 314 generated by the bias voltage applied from both ends of the photoelectric conversion film 314 is reduced, which makes it difficult to collect charge. Therefore, the thickness of the photoelectric conversion film 314 is preferably from 30 nm to 300 nm, more preferably from 50 nm to 250 nm, and most preferably from 80 nm to 200 nm.

In the radiation detector 36 shown in FIG. 23, one photoelectric conversion film 314 is common to all pixel units. However, the photoelectric conversion film 314 may be divided for each pixel unit.

The lower electrode 312 is a thin film that is divided for each pixel unit. The lower electrode 312 may be appropriately made of a transparent or opaque conductive material, such as aluminum or silver.

The thickness of the lower electrode 312 may be, for example, from 30 nm to 300 nm.

In the photoelectric conversion unit 82, a predetermined bias voltage can be applied between the upper electrode 310 and the lower electrode 312 to move one of the charges (a hole and an electron) generated from the photoelectric conversion film 314 to the upper electrode 310 and move the other charge to the lower electrode 312. In the radiation detector 36 according to this embodiment, a wiring line is connected to the upper electrode 310 and the bias voltage is applied to the upper electrode 310 through the wiring line. It is assumed that the polarity of the bias voltage is determined such that the electron generated in the photoelectric conversion film 314 is moved to the upper electrode 310 and the hole is moved to the lower electrode 312. However, the polarity may be reversed.

The photoelectric conversion unit 82 forming each pixel unit may include at least the lower electrode 312, the photoelectric conversion film 314, and the upper electrode 310. In order to prevent an increase in dark current, it is preferable that at least one of the electron blocking film 316 and the hole blocking film 318 be provided, and it is more preferable that both the electron blocking film 316 and the hole blocking film 318 be provided.

The electron blocking film 316 may be provided between the lower electrode 312 and the photoelectric conversion film 314. In a case in which the bias voltage is applied between the lower electrode 312 and the upper electrode 310, it is possible to prevent an increase in the dark current due to the injection of electrons from the lower electrode 312 into the photoelectric conversion film 314.

The electron blocking film 316 may be made of an electron donating organic material.

In practice, the material used for the electron blocking film 316 may be selected according to a material forming an adjacent electrode and a material forming an adjacent photoelectric conversion film 314. It is preferable that the material used for the electron blocking film 316 have an electron affinity (Ea) that is at least 1.3 eV higher than the work function (Wf) of the material forming the adjacent electrode and have an ionization potential (Ip) equal to or less than that of the material forming the adjacent photoelectric conversion film 314. Materials applicable as the electron donating organic material have been described in detail in JP-A No. 2009-32854 and thus a detailed description thereof will be omitted.

The thickness of the electron blocking film 316 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the photoelectric conversion unit 82.

The hole blocking film 316 may be provided between the photoelectric conversion film 314 and the upper electrode 310. In a case in which the bias voltage is applied between the lower electrode 312 and the upper electrode 310, it is possible to prevent an increase in the dark current due to the injection of holes from the upper electrode 310 into the photoelectric conversion film 314.

The hole blocking film 318 may be made of an electron accepting organic material.

The thickness of the hole blocking film 318 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the photoelectric conversion unit 82.

In practice, the material used for the hole blocking film 318 may be selected according to a material forming an adjacent electrode and a material forming an adjacent photoelectric conversion film 314. It is preferable that the material used for the hole blocking film 318 have an ionization potential (Ip) that is at least 1.3 eV higher than the work function (Wf) of the material forming the adjacent electrode and have an electron affinity (Ea) equal to or more than that of the material forming the adjacent photoelectric conversion film 314. Materials applicable as the electron accepting organic material have been described in detail in JP-A No. 2009-32854 and thus a detailed description thereof will be omitted.

In a case in which the bias voltage is set such that, among the charges generated in the photoelectric conversion film 314, holes are moved to the upper electrode 310 and electrons are moved to the lower electrode 312, the positions of the electron blocking film 316 and the hole blocking film 318 may be reversed. In addition, neither the electron blocking film 316 nor the hole blocking film 318 may be provided. When either the electron blocking film 316 or the hole blocking film 318 is provided, it is possible to a certain extent to obtain the effect of preventing the dark current.

The signal output unit 302 is provided on the surface of the substrate 300 below the lower electrode 312 of each pixel unit.

Figure 24:
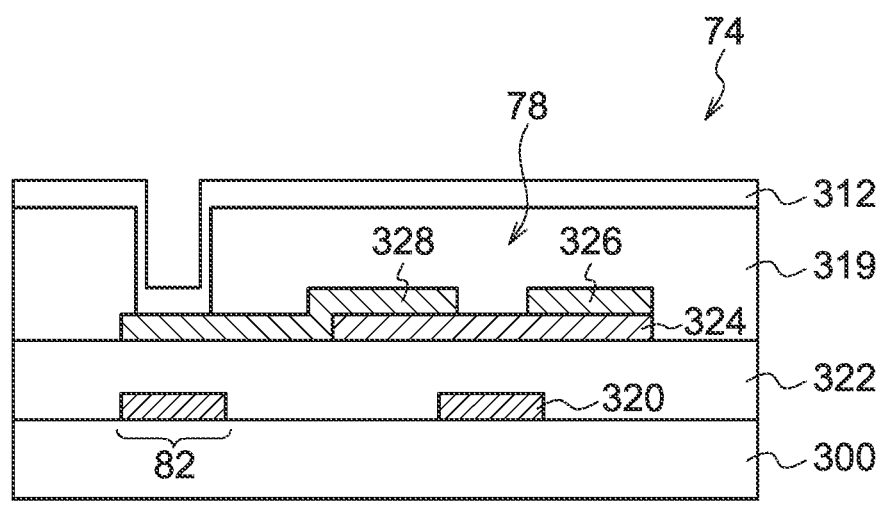
FIG. 24 is a cross-sectional view schematically illustrating a structure of a TFT substrate.

FIG. 24 is a diagram schematically illustrating the structure of the signal output unit 302.

A storage capacitor 76 that stores the charge moved to the lower electrode 312 and a TFT 78 that converts the charge stored in the storage capacitor 76 into an electric signal and outputs the electric signal are formed so as to correspond to the lower electrode 312. A region in which the storage capacitor 76 and the TFT 78 are formed has a portion that overlaps the lower electrode 312 in a plan view. In this way, the signal output unit 302 and the photoelectric conversion unit 82 in each pixel unit overlap each other in the thickness direction. In order to minimize the plane area of the radiation detector 36 (pixel unit), it is preferable that the region in which the storage capacitor 76 and the TFT 78 are formed be completely covered with the lower electrode 312.

The storage capacitor 76 is electrically connected to the lower electrode 312 through a conductive line that is formed so as to pass through the insulating film 319 provided between the substrate 300 and the lower electrode 312. In this way, it is possible to move the charge captured by the lower electrode 312 to the storage capacitor 76.

The TFT 78 is formed by laminating a gate electrode 320, a gate insulating film 322, and an active layer (channel layer) 324 and providing a source electrode 326 and a drain electrode 328 on the active layer 324 with a predetermined gap therebetween. The active layer 324 may be made of, for example, amorphous silicon, an amorphous oxide, an organic semiconductor material, or carbon nanotubes. The material forming the active layer 324 is not limited thereto.

An oxide (for example, an In—O-based oxide) including at least one of In, Ga, and Zn is preferable as the amorphous oxide that can form the active layer 324. An oxide (for example, an In—Zn—O-based oxide, an In—Ga—O-based oxide, or a Ga—Zn—O-based oxide) including at least two of In, Ga, and Zn is more preferable as the amorphous oxide. An oxide including In, Ga, and Zn is most preferable as the amorphous oxide. As an In—Ga—Zn—O-based amorphous oxide, an amorphous oxide having a composition represented by $InGaO_3(ZnO)_m$ (m is a natural number smaller than 6) in a crystalline state is preferable, and $InGaZnO_4$ is more preferable. The amorphous oxide that can form the active layer 324 is not limited thereto.

A phthalocyanine compound, pentacene, or vanadyl phthalocyanine may be given as an example of the organic semiconductor material that can form the active layer 324, but the organic semiconductor material is not limited thereto. The structure of the phthalocyanine compound has been described in detail in JP-A No. 2009-212389 and thus a detailed description thereof will be omitted.

When the active layer 324 of the TFT 78 is made of an amorphous oxide, an organic semiconductor material, or carbon nanotubes, radiation, such as X-rays, is not absorbed. Even though the radiation is absorbed, a very small amount of radiation remains. Therefore, it is possible to effectively prevent the generation of noise in the signal output unit 302.

In a case in which the active layer 324 is made of carbon nanotubes, it is possible to improve the switching speed of the TFT 78 and form the TFT 78 with low light absorptance in the visible light range. In addition, in a case in which the active layer 324 is made of carbon nanotubes, even though a very small amount of metallic impurities is mixed with the active layer 324, the performance of the TFT 78 is significantly reduced. Therefore, it is necessary to separate and extract carbon nanotubes with very high purity using, for example, centrifugal separation and form the active layer with the carbon nanotube.

All of the amorphous oxide, the organic semiconductor material, the carbon nanotubes, and the organic photoelectric conversion material can be used to form a film at a low temperature. The substrate 300 is not limited to a substrate with high heat resistance, such as a semiconductor substrate, a quartz substrate, or a glass substrate, but a flexible substrate, such as a plastic substrate, an aramid substrate, or a bio-nanofiber substrate may be used as the substrate 300. Specifically, for example, a flexible substrate made of the following materials may be used: polyester, such as polyethylene terephthalate, polybutylene phthalate, or polyethylene naphthalate, polystyrene, polycarbonate, polyether sulfone, polyarylate, polyimide, polycycloolefin, norbornene resin, and poly(chlorotrifluoroethylene). When the flexible substrate made of plastic is used, it is possible to reduce the weight of the substrate. For example, this structure has an advantage in portability.

In addition, for example, an insulating layer for ensuring an insulating property, a gas barrier layer for preventing the penetration of water or oxygen, and an undercoating layer for improving flatness or the adhesion of, for example, the electrode may be provided on the substrate 300.

Since aramid can be applied to a high-temperature process of 200 degrees or more, a transparent electrode material can be cured at a high temperature to have low resistance, and the aramid can respond to the automatic mounting of a driver IC including a solder reflow process. In addition, the thermal expansion coefficient of aramid is close to that of ITO (indium tin oxide) or a glass substrate. Therefore, after an aramid substrate is manufactured, the warping of the aramid substrate is small and the aramid substrate is less likely to be cracked. In addition, aramid is capable of forming a substrate thinner than, for example, a glass substrate. Aramid may be laminated on a super-thin glass substrate to form the substrate 300.

The bio-nanofiber is a composite of a cellulose microfibril bundle generated by bacteria (Acetobacter Xylinum) (bacterial cellulose) and a transparent resin. The cellulose microfibril bundle has a width of 50 nm, a size of one-tenth of the visible light wavelength, high strength, high elasticity, and a low thermal expansion coefficient. A transparent resin, such as an acrylic resin or an epoxy resin, is impregnated into the bacterial cellulose and is then cured to obtain bio-nanofiber that has a light transmittance of about 90% at a wavelength of 500 nm while including 60 to 70% of fiber. The bio-nanofiber has a low thermal expansion coefficient (3 to 7 ppm) equal to that of a silicon crystal, strength (460 MPa) similar to that of iron, high elasticity (30 GPa), and flexibility. Therefore, the bio-nanofiber is capable of forming a substrate 300 thinner than, for example, a glass substrate.

In this embodiment, the signal output unit 302, the photoelectric conversion unit 82, and the transparent insulating film 306 are sequentially formed on the substrate 300 and the scintillator 304 is bonded to the substrate 300 by an adhesive resin with low light absorptance, thereby forming the radiation detector 36. Hereinafter, the substrate 300 including up to the transparent insulating film 306 formed thereon is referred to as the TFT active matrix substrate (hereinafter, referred to as a "TFT substrate") 74.

In the electronic cassette 20 according to this embodiment, the radiation detector 36 is provided in the electronic cassette 20 such that the radiation X is emitted from the TFT substrate 74.

Figure 25:
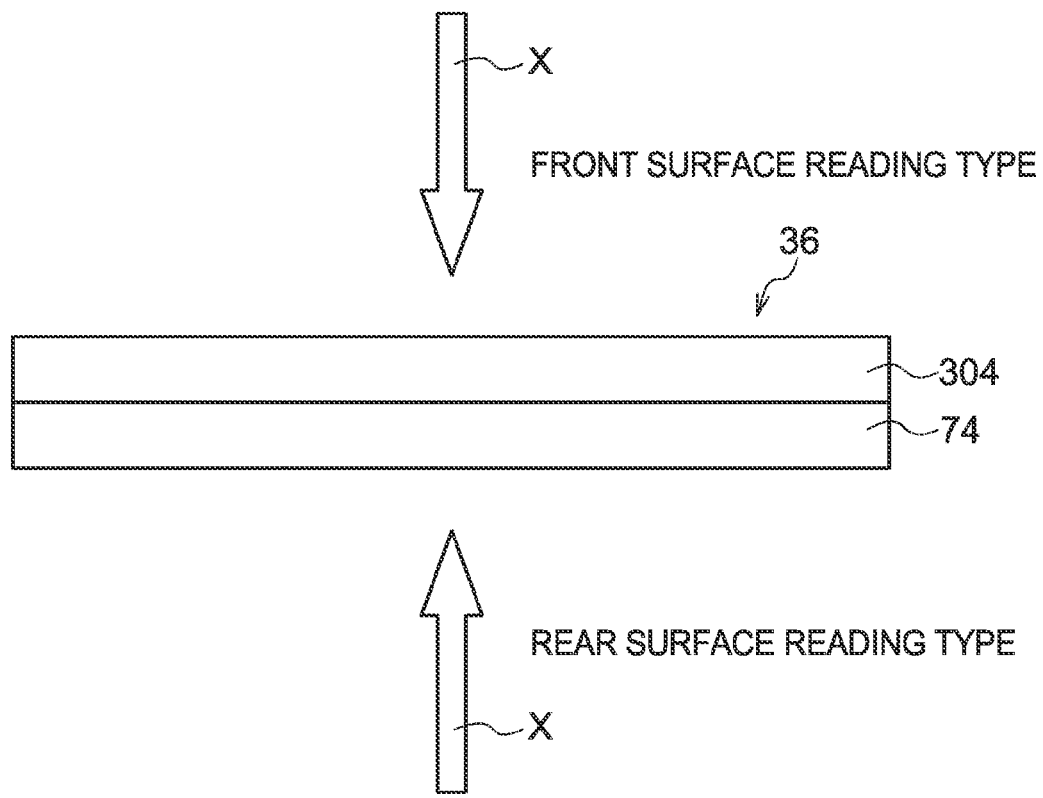
FIG. 25 is a cross-sectional view illustrating a front surface reading type and a rear surface reading type.

As shown in FIG. 25, in a case in which the radiation detector 30 is a so-called rear surface reading type (so-called PSS (Penetration Side Sampling) type) in which radiation is emitted from the side where the scintillator 304 is formed and the TFT substrate 74 that is provided on the side opposite to the incident surface of the radiation reads a radiological image, high-intensity light is emitted from the upper surface (the surface opposite to the TFT substrate 74) of the scintillator 304. When the radiation detector 30 is a so-called front surface reading type (so-called ISS (Irradiation Side Sampling) type) in which radiation is emitted from the side of the TFT substrate 74 and the TFT substrate 74 that is provided on the incident surface of the radiation reads a radiological image, the radiation passing through the TFT substrate 74 is incident on the scintillator 304 and high-intensity light is emitted from the surface of the scintillator 304 close to the TFT substrate 74. Each of the photoelectric conversion units 82 provided on the TFT substrate 74 generates charge using light emitted from the scintillator 304. Therefore, in the radiation detector 36 of the front surface reading type, the emission position of the scintillator 304 with respect to the TFT substrate 74 is closer to that in the radiation detector 30 of the rear surface reading type. As a result, the resolution of the radiological image captured in the front surface reading type is higher than that of the radiological image captured in the rear surface reading type.

In the radiation detector 36, the photoelectric conversion film 314 is made of an organic photoelectric conversion material and radiation is hardly absorbed by the photoelectric conversion film 314. Therefore, in the radiation detector 36 according to this embodiment, in the front surface reading type, even when radiation passes through the TFT substrate 74, the amount of radiation absorbed by the photoelectric conversion film 314 is small. Therefore, it is possible to prevent a reduction in sensitivity for the radiation X. In the front surface reading type, radiation passes through the TFT substrate 74 and reaches the scintillator 304. However, as such, in a case in which the photoelectric conversion film 314 of the TFT substrate 74 is made of an organic photoelectric conversion material, the radiation is hardly absorbed by the photoelectric conversion film 314 and it is possible to reduce the attenuation of the radiation. The radiation detector 36 is suitable for the front surface reading type.

Both the amorphous oxide forming the active layer 324 of the TFT 78 and the organic photoelectric conversion material forming the photoelectric conversion film 314 can be used to form a film at a low temperature. Therefore, the substrate 300 can be made of a plastic resin, aramid, or bio-nanofiber that absorbs a small amount of radiation. Since the substrate 300 formed in this way absorbs a small amount of radiation, it is possible to prevent a reduction in sensitivity for the radiation X even when radiation passes through the TFT substrate 74 in the front surface reading type.

For example, in a case in which the radiation detector 36 is adhered to the irradiation surface 32 of the casing 30 such that the TFT substrate 74 faces the irradiation surface 32 and the substrate 300 is made of a plastic resin with high rigidity, aramid, or bio-nanofiber, it is possible to reduce the thickness of the irradiation surface 32 of the casing 30 since the radiation detector 36 has high rigidity. In addition, in a case in which the substrate 300 is made of a plastic resin with high rigidity, aramid, or bio-nanofiber, the radiation detector 36 has flexibility. Therefore, even when an impact is applied to the irradiation surface 32, the radiation detector 36 is less likely to be damaged.

Next, a function of the imaging system 10 according to this exemplary embodiment will be described.

In a case in which the IVR is executed on the patient 14 using the imaging system 10 according to this exemplary embodiment, first, the technician that executes the IVR inputs the coordinate information indicating an entry scheduled path of the catheter 60 as follows, as a preparing step of the IVR.

That is, first, the technician makes the patient 14 lie on the object table 16A in a state where an insertion opening of the catheter 60 and a lesion part may be image captured by the electronic cassette 20. Next, the technician causes the radiation irradiating device 18 to change states of the slit plates 44A to 44D of the diaphragm unit 44 to fully open states through the console 26, and controls the radiation source 42 to emit the radiation X with a predetermined exposure dose. Meanwhile, the technician controls the electronic cassette 20 to capture a radiation image. Thereby, in the electronic cassette 20, the radiation image is captured in a manner that will be described below in connection with a radiation image capturing process (see FIG. 7), and image information that is obtained by capturing the image is transmitted to the console 26. Meanwhile, if the image information is received, the console 26 displays the radiation image, which is indicated by the image information, on the display of the UI panel 110.

Therefore, the technician traces the entry scheduled path of the catheter 60 in the body of the patient 14 on the radiation image displayed on the display of the UI panel 110 with the touch pen, and thereby inputs the coordinate information of the entry scheduled path. The coordinate information is stored in the HDD 120 by the CPU 114 of the console 26.

If the above preparation step ends, the technician performs an exposure condition-designating operation to designate exposure conditions such as a tube voltage and a tube current when the radiation X is irradiated through the operation panel 112 of the console 26 according to the imaging part or the imaging condition of the patient 14, and gives an instruction to start execution of the IVR.

If the instruction is given, the console 26 executes the radiation image capturing processing.

Figure 7:
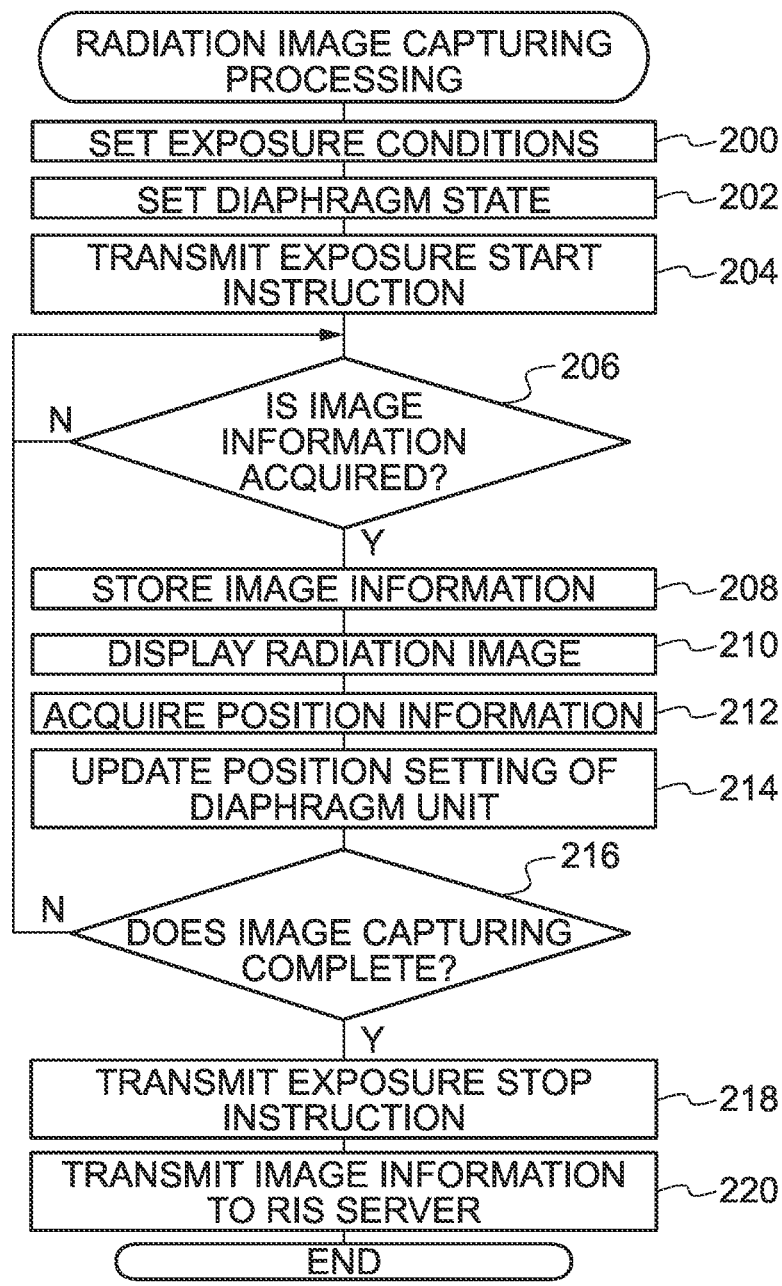
FIG. 7 is a flowchart illustrating a processing flow of a radiation image capturing processing program according to the first exemplary embodiment.

Next, a function of the console 26 that is performed when the radiation image capturing processing is executed will be described with reference to FIG. 7. FIG. 7 is a flowchart illustrating a processing flow of a radiation image capturing processing program that is executed by the CPU 114 of the console 26 at this point in time. The program is stored in advance in a predetermined area of the ROM 116.

In step 200 of FIG. 7, the designated exposure conditions are transmitted to the radiation irradiating device 18 and the electronic cassette 20 and the exposure conditions are set. According to this, the irradiating device control unit 140 performs an exposure preparation under the received exposure conditions.

Next, in step 202, the information that indicates the position of the insertion opening of the catheter 60 indicated by the coordinate information stored in the step for preparing the IVR and the setting instruction information that instructs setting of the opening state of the diaphragm unit 44 are transmitted to the radiation irradiating device 18.

If the setting instruction information is received, in the radiation irradiating device 18, the irradiating device control unit 140 controls the positions of the slit plates 44A to 44D, such that the position corresponding to the position of the insertion opening of the catheter 60 indicated by the information received together with the setting instruction information indicates the center of the opening region 51, a shape of the opening region 51 is a predetermined shape, and an area of the opening region 51 is a predetermined area which is previously set as an area which is narrower than an area of the fully open state. In the imaging system 10 according to this exemplary embodiment, as the predetermined shape and the predetermined area, a shape and an area are applied which are previously set by the technician as a shape and an area in which a region of the patient 14 where the direct rays of the radiation X are irradiated is a region of interest.

Since the predetermined area determines the area onto which the direct rays of the radiation X are to be irradiated, the predetermined area is preferably appropriately set according to the size of the treatment object part or the cumulative exposure dose of the radiation X with respect to the same patient. For example, an area which is fixedly set in advance may be applied such as an area onto which the direct rays of the radiation X is irradiated to an area corresponding to a predetermined proportion (for example, 10%) with respect to the area of the irradiation surface 36A of the radiation detector 36.

Next, in step 204, the instruction information that instructs to start an exposure is transmitted to the radiation irradiating device 18 and the electronic cassette 20. According to this, the radiation source 42 generates the radiation with the tube voltage and the tube current according to the exposure conditions received by the radiation irradiating device 18 from the console 26 and emits the radiation.

The radiation X that is irradiated from the radiation source 42 transmits the patient 14 via the diaphragm unit 44 and reaches the electronic cassette 20. Thus, the electric charge is accumulated in the storage capacitor 76 of each pixel portion 80 of the radiation detector 36 that is incorporated in the electronic cassette 20.

The cassette control unit 100 of the electronic cassette 20 controls the gate line driver 88, after a lapse of a previously determined period that is the period from reception of the instruction information instructing to start the exposure to completion of the accumulation of the electric charge in the storage capacitor 76 of each pixel portion 80 of the radiation detector 36, to output an ON signal from the gate line driver 88 to each gate line 84 line by line, and sequentially turns on the TFTs 78 connected to each gate line 84 line by line.

When the TFTs 78 connected to each gate line 84 are sequentially turned on line by line, the electric charge accumulated in each storage capacitor 76 as the electric signal sequentially flows to each data line 86 line by line. The electric signal that flows to each data line 86 is converted into digital image information by the signal processing unit 90 and is stored in the line memory 98.

After image information stored in the line memory 98 is subjected to image correcting processing set previously, the cassette control unit 100 transmits the processed image information to the console 26 through the optical communication control unit 102.

The cassette control unit 100 executes the above operation at the speed (30 frame/second in this exemplary embodiment) previously set as the movie capturing speed, and controls the display driver 104 such that a radiation image indicated by image information subjected to image correcting processing is displayed by the display 28.

In step 206, a waiting state is maintained until image information corresponding to one frame is received from the electronic cassette 20. In step 208, the received image information is stored in the HDD 120. In step 210, the cassette control unit 100 controls the UI panel control unit 122 such that a radiation image that is indicated by the received image information is displayed by the display of the UI panel 110 to permit confirmation of the radiation image.

Next, in step 212, position information that indicates the position of a tip end of the catheter 60 is obtained.

In the console 26 according to this exemplary embodiment, a position specification processing program that time-divisionally specifies the position of the tip end of the catheter 60 is executed in parallel with execution of the radiation image capturing processing program.

In the position specification processing program, in a case in which the electric signals that are time-serially received in real time from the reflective photo sensor 62 indicate that regions progress in order of a wide white region, a narrow black region, and a narrow white region in striped pattern provided in the catheter 60, it is determined that the catheter 60 moves in a direction where the catheter is inserted into the body of the patient 14, and the movement amount at this point in time is specified by multiplying number of appearance of the wide white region by the width of one group of the striped pattern. Likewise, in a case in which the electric signals indicate that regions progress in order of a wide black region, a narrow white region, and a narrow black region in the stripped pattern, it is determined that the catheter 60 moves in a direction where the catheter is pulled out from the body of the patient 14, and the movement amount at this point in time is specified by multiplying number of appearance of the wide black region by the width of one group of the striped pattern.

In the position specification processing program, the movement amount when the catheter 60 moves in the direction where the catheter is inserted into the body of the patient 14, which is obtained by the above processing, is integrated, the movement amount when the catheter 60 moves in the direction where the catheter is pulled out from the body of the patient 14 is subtracted, and the insertion amount of the catheter 60 with respect to the body of the patient 14 is specified.

In the position specification processing program, the position of the tip end of the catheter 60 is specified on the basis of the specified insertion amount and the coordinate information indicating the entry scheduled path of the catheter 60 stored in the preparation step of the IVR, and the coordinate information indicating the position is stored in a predetermined area of the RAM 118 in real time.

Therefore, in step 212, the position information that indicates the position of the tip end of the catheter 60 is acquired by reading the stored coordinate information from the RAM 118 by the position specification processing program.

In step 214, the information that indicates the position of the tip end of the catheter 60 indicated by the acquired position information and the change instruction information that instructs to change the opening state of the diaphragm unit 44 are transmitted to the radiation irradiating device 18.

If the change instruction information is received, in the radiation irradiating device 18, the irradiating device control unit 140 controls the positions of the slit plates 44A to 44D, such that the position corresponding to the position of the tip end of the catheter 60 indicated by the information received together with the change instruction information is the center of the opening region 51 and the shape and the area of the opening region 51 is the predetermined shape and the predetermined area.

In step 216, it is determined whether the timing at which capturing of the radiation image ends has come. If determination result is NO, the process returns to step 206. At a point in time when the determination result is YES, the process proceeds to step 218. In the radiation image capturing processing program according to this exemplary embodiment, whether a timing at which capturing of the radiation image ends has come is determined by determining whether the technician inputs instruction information instructing to terminate capturing of the radiation image through the input unit such as the operation panel 112. However, the invention is not limited thereto and another form may be used. For example, it may be determined by determining whether a power supply switch (not shown in the drawings) of the electronic cassette 20 or the radiation irradiating device 18 is turned off.

In step 218, instruction information that instructs to stop the exposure started by the process of step 204 is transmitted to the radiation irradiating device 18 and the electronic cassette 20. In step 220, after the image information stored by the process of step 208 is transmitted to a Radiology Information System (RIS) server (not shown in the drawings) through an in-hospital network (not shown in the drawings), the radiation image capturing processing program ends. In the RIS server, a doctor may interpret or diagnose the radiation image that is captured using the image information received from the console 26.

Figure 8:
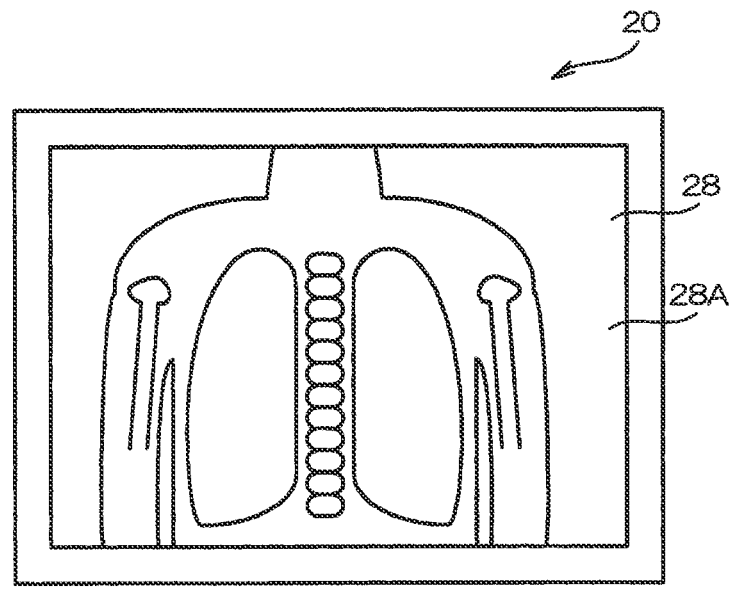
FIG. 8 is a diagram illustrating an example of a radiation image that is displayed on a display surface of a display by irradiating radiation onto the entire surface of an irradiation surface of the radiation detector according to the first exemplary embodiment.
Figure 9:
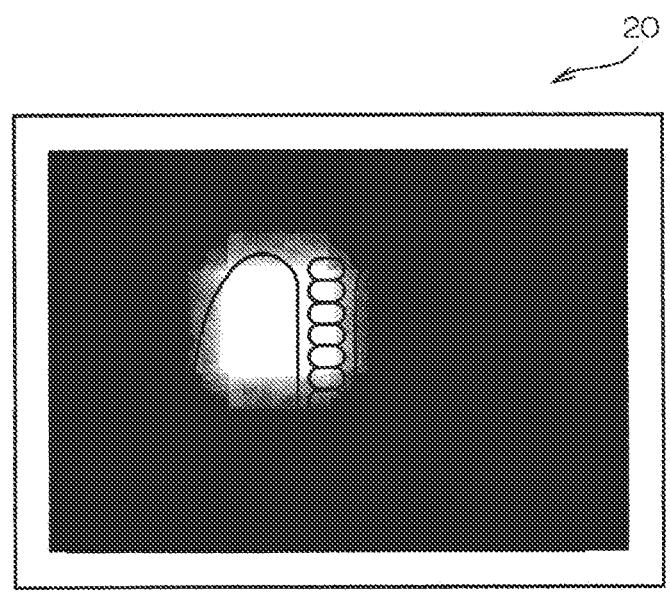
FIG. 9 is a diagram illustrating an example of a radiation image that is displayed on the display surface of the display by irradiating radiation onto a partial region of the irradiation surface of the radiation detector according to the first exemplary embodiment.

FIG. 8 shows an example of a radiation image that is displayed on the display surface 28A of the display 28 by irradiating the radiation X onto an entire surface of an irradiation surface 36A of the radiation detector 36 according to this exemplary embodiment. FIG. 9 shows an example of a radiation image in a case in which the patient 14 lies in the same state as the state shown in FIG. 8, which is displayed on the display surface 28A of the display 28 by executing the radiation image capturing processing program according to this exemplary embodiment and irradiating radiation onto a partial region of the irradiation surface 36A of the radiation detector 36.

As shown in FIG. 9, in the imaging system 10 according to this exemplary embodiment, since the irradiation region of the direct rays of the radiation X may be restricted to the predetermined region (a region of interest in this exemplary embodiment), the exposure dose with respect to the patient 14 may be suppressed. In addition, the image according to the transmission dose of the position of the corresponding slit plate is displayed as an example in the state shown in FIG. 9 with respect to the region of the peripheral part of the predetermined region (gradation region in the display image of FIG. 9), therefore, a radiation image of the peripheral part may be observed.

As described in detail above, according to this exemplary embodiment, the area of the opening region 51 of the diaphragm unit 44 that reduces the radiation X irradiated onto the patient 14 can be changed, and the diaphragm unit 44 is controlled such that the direct rays of the radiation X are irradiated onto the predetermined region of the patient 14. The diaphragm unit 44 is configured such that the transmission dose of the radiation X decreases as the distance from the circumferential part of the opening region 51 increases. Therefore, the radiation image of the peripheral part of the imaging object region may be observed, with suppressed exposure dose with respect to the patient 14.

In this exemplary embodiment, since the diaphragm unit 44 is configured to change the position and the shape of the opening region 51, the irradiation shape of the radiation X may be changed and the irradiation position of the radiation X may be changed.

In this exemplary embodiment, the diaphragm unit 44 is configured such that the thickness in the transmission direction of the radiation X increases as the distance from the circumferential part of the opening region 51 increases, and thereby the transmission dose of the radiation X decreases as the distance from the circumferential part of the opening region 51 increases. Therefore, the diaphragm unit 44 may be easily configured as compared with the case where the transmission dose of the radiation X in the diaphragm unit 44 is reduced by a quality of a material constituting the diaphragm unit 44.

In particular, in this exemplary embodiment, the diaphragm unit 44 is configured such that the thickness linearly changes in sectional view, that is, linearly increases as the distance from the circumferential part of the opening region 51 increases. Therefore, a discomfort sense on the radiation image of the peripheral part of the imaging object region may be reduced as compared with the case of the configuration where the thickness increases stepwise (non-linearly) in sectional view.

In this exemplary embodiment, the diaphragm unit 44 is controlled such that the direct rays of the radiation X are irradiated tracking the region of interest that changes with time. Therefore, convenience may be improved.

In a case in which a columnar crystal of CsI is used as the scintillator 304 and the radiation detector 36 is provided in the electronic cassette 20 such that the radiation detector 36 is the front surface reading type, a high quality image can be obtained. Further, if an organic photoelectric material is used for the photoelectric conversion film 314, radiation is hardly absorbed by the photoelectric conversion film 314, a large amount of radiation reaches the scintillator 304, and thus sensitivity can be improved. In a case in which the opening region 51 is narrowed by the diaphragm unit 44 such that radiation transmitting through the diaphragm unit 44 is irradiated at a circumferential part of a region of interest, a little blur occurs in the radiation image at the circumferential part of the region of interest; however, the image is high quality, and therefore, it is not a problem. Further, a doctor or a technician can confirm whether radiation is also irradiated to an unnecessary region for diagnosis by observing the blur at the circumferential part of the region of interest.

Figure 26:
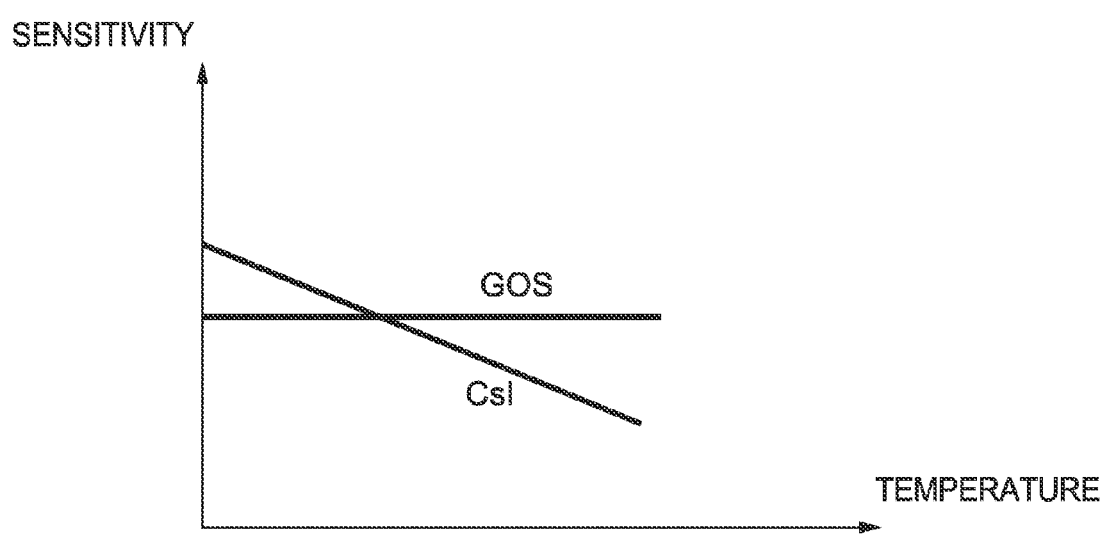
FIG. 26 is a graph illustrating relationships between temperatures and sensitivity of CsI and GOS.

The sensitivity of CsI which is used as the scintillator 304 changes as a temperature changes as shown in FIG. 26. For example, the sensitivity lowers about 0.3% if a temperature rises one degree. The sensitivity of GOS hardly changes as a temperature changes.

Circuits and elements such as the power supply unit 106, the gate line driver 88 and the signal processing unit 90 in the electronic cassette 20 generate heat by capturing images. Further, if a movie is captured by the IVR, a capturing time is long. Thus, in the electronic cassette 20 which uses CsI as the scintillator 304, there are cases in which the sensitivity of the scintillator 304 is lowered by heat from the circuits and elements when capturing a movie. The technician who performs IVR increases a radiation dose to be irradiated if the technician wishes to maintain an image quality necessary for diagnosis. However, if the radiation dose increases, an exposure dose to a patient will increase. In the present embodiment, the area of the opening region 51 of the diaphragm unit 44 that reduces the radiation X irradiated onto the patient 14 can be changed, and the diaphragm unit 44 is configured such that the transmission dose of the radiation X decreases as the distance from the circumferential part of the opening region 51 increases, whereby an increase in exposure dose with respect to the patient 14 can be suppressed.

Figure 27:
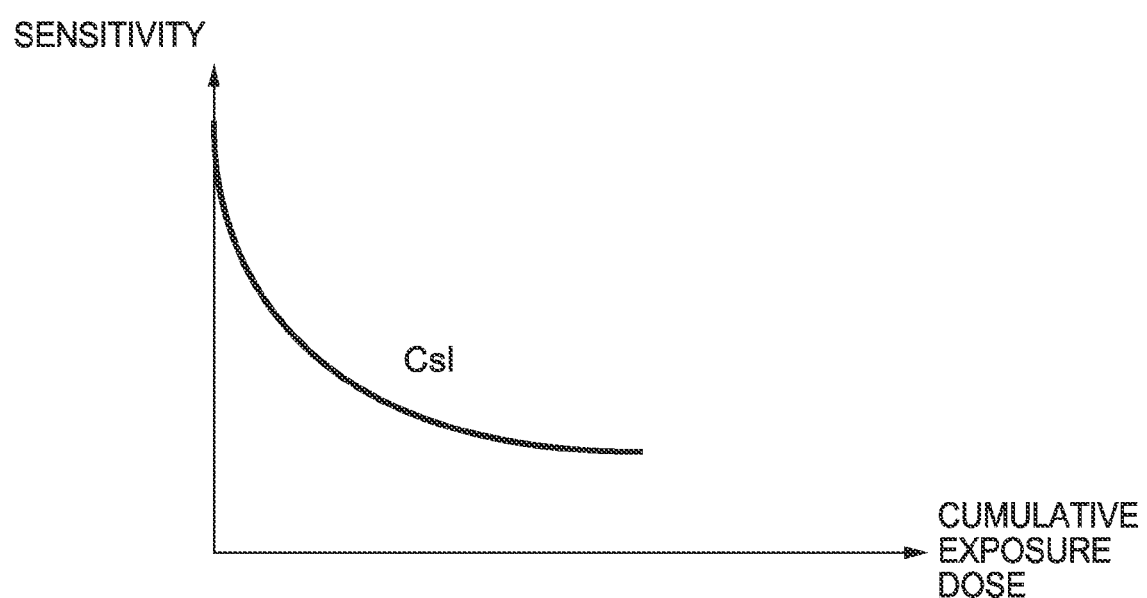
FIG. 27 is a graph illustrating relationships between a cumulative exposure dose and a sensitivity of CsI.

The sensitivity of CsI lowers as the cumulative exposure dose increases when capturing images continuously, and when a condition in which radiation is not irradiated is maintained, the sensitivity which has lowered recovers, as shown in FIG. 27. In a case in which a movie is captured by IVR or the like, an imaging time is long. In a case in which static images are captured frequently when capturing a movie, an irradiation amount of radiation for capturing a static image is about 10-100 times that per one frame capturing a movie, and thus, the sensitivity of the scintillator 304 lowers as the cumulative exposure dose increases. In this case, if a technician wishes to maintain an image quality necessary for diagnosis, the technician increases the radiation dose to be irradiated. However, if the radiation dose increases, an exposure dose to a patient will increase. In the present embodiment, the area of the opening region 51 of the diaphragm unit 44 that reduces the radiation X irradiated onto the patient 14 can be changed, and the diaphragm unit 44 is configured such that the transmission dose of the radiation X decreases as the distance from the circumferential part of the opening region 51 increases, whereby an increase in exposure dose with respect to the patient 14 can be suppressed.

In the present embodiment, the diaphragm unit 44 is configured such that the transmission dose of the radiation X decreases as the distance from the circumferential part of the opening region 51 increases, and thus, an increase in exposure dose with respect to the patient can be suppressed even if the radiation dose of the radiation X to be irradiated is increased accompanying a decrease in the sensitivity of the scintillator 304.

Second Exemplary Embodiment

Since the configuration of an imaging system 10 according to the second exemplary embodiment is the same as that of the first exemplary embodiment, the description will not be repeated.

The imaging system 10 according to this exemplary embodiment is provided with an exposure dose restriction function is mounted, which restricts an exposure dose with respect to an irradiation field other than the region of interest of the radiation X if a cumulative exposure dose per unit area (1 cm$^2$ in this exemplary embodiment) for a period starting from a point in time when medical treatment on the patient 14 starts, reaches a predetermined exposure dose threshold value. For this reason, in the imaging system 10 according to this exemplary embodiment, information (hereinafter, referred to as "exposure dose threshold value information") that indicates the exposure dose threshold value is stored in the HDD 120 of the console 42 in advance.

FIG. 10 schematically shows an example of the exposure dose threshold value information according to a second exemplary embodiment. As shown in FIG. 10, in the exposure dose threshold value information according to this exemplary embodiment, the exposure dose threshold value is stored for each kind of internal organs such as heart, lungs, and a stomach. The exposure dose threshold value information may be set on the basis of Guideline for Medical Exposure suggested by Japan Association of Radiological Technicians.

Next, a function of the imaging system 10 according to this exemplary embodiment will be described.

In a case in which the IVR is executed on the patient 14 using the imaging system 10 according to this exemplary embodiment, the technician that executes the IVR first inputs the coordinate information indicating an entry scheduled path of the catheter 60 as follows, as a preparing step of the IVR.

That is, first, the technician makes the patient 14 lie on the object table 16A in a state where an insertion opening of the catheter 60 and a lesion part may be image captured by the electronic cassette 20. Next, the technician causes the radiation irradiating device 18 to change states of the slit plates 44A to 44D of the diaphragm unit 44 to fully open states through the console 26, and controls the radiation source 42 to emit the radiation X with a predetermined exposure dose. Meanwhile, the technician controls the electronic cassette 20 to capture a radiation image. Thereby, in the electronic cassette 20, the radiation image is captured in a manner that will be described below in connection with a radiation image capturing process (see FIG. 11), and image information that is obtained by capturing the image is transmitted to the console 26. Meanwhile, when the image information is received, the console 26 displays the radiation image, which is indicated by the image information, on the display of the UI panel 110.

Therefore, the technician traces the entry scheduled path of the catheter 60 in the body of the patient 14 on the radiation image displayed on the display of the UI panel 110 with the touch pen, and inputs coordinate information (hereinafter, referred to as "path coordinate information") of the entry scheduled path. At this time, the technologies traces the contour of an internal organ (hereinafter, referred to as "determination object internal organ) that exists on the entry scheduled path and a region to be an irradiation field of the radiation X in the vicinity of the entry scheduled path and thereby inputs coordinate information (hereinafter, referred to as "internal organ coordinate information") indicating the region where the determination object internal organ exists, and inputs information indicating each name of the determination object internal organ existing in the region indicated by the internal organ coordinate information through the operation panel 112. The path coordinate information, the internal organ coordinate information, and the internal organ name information that are input by the technician in the above-described way are stored in the HDD 120 in a state where the internal organ coordinate information and the internal organ name information corresponding to each other are associated by the console 26.

After the above preparation step ends, the technician performs an exposure condition designating operation to designate exposure conditions such as a tube voltage and a tube current when the radiation X is irradiated through the operation panel 112 of the console 26, according to the imaging part or the imaging condition of the patient 14, and performs an instruction operation to instruct to start execution of the IVR.

When the instruction operation is performed, the console 26 executes the radiation image capturing processing.

Figure 11:
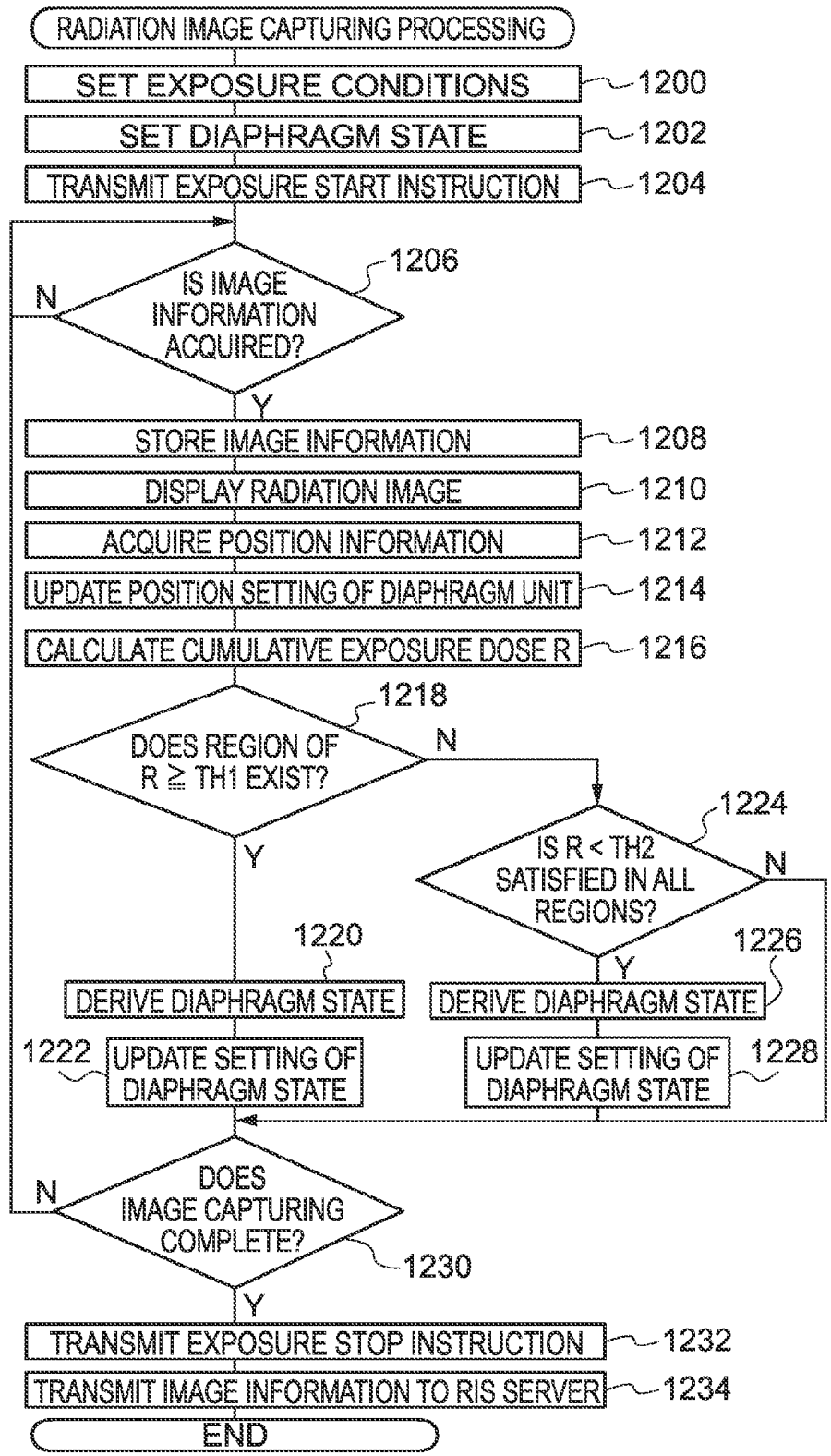
FIG. 11 is a flowchart illustrating a processing flow of a radiation image capturing processing program according to the second exemplary embodiment.

Next, a function of the console 26 when the radiation image capturing processing is executed will be described with reference to FIG. 11. FIG. 11 is a flowchart illustrating a processing flow of a radiation image capturing processing program that is executed by the CPU 114 of the console 26 at this point in time. The program is previously stored in a predetermined area of the ROM 116.

In step 1200 of FIG. 11, the designated exposure conditions are transmitted to the radiation irradiating device 18 and the electronic cassette 20 and the exposure conditions are set. According to this, the irradiating device control unit 140 performs an exposure preparation under the received exposure conditions.

In step 1202, the information that indicates the position of the insertion opening of the catheter 60 indicated by the path coordinate information stored in the preparation step of the IVR and the setting instruction information that instructs setting of the opening state of the diaphragm unit 44 are transmitted to the radiation irradiating device 18.

When the setting instruction information is received, in the radiation irradiating device 18, the irradiating device control unit 140 controls the positions of the slit plates 44A to 44D, such that the position corresponding to the position of the insertion opening of the catheter 60 indicated by the information received together with the setting instruction information is the center of the opening region 51, a shape of the opening region 51 is a predetermined shape, and an area of the opening region 51 is a predetermined area previously set as an area which is narrower than an area of the fully open state. In the imaging system 10 according to this exemplary embodiment, as the predetermined shape and the predetermined area, a shape and an area are applied, which are previously set by the technician as a shape and an area in which a region (hereinafter, referred to as "direct ray irradiation field") of the patient 14 where the direct rays of the radiation X are irradiated includes at least a region of interest.

Since the predetermined area is the area where the direct rays of the radiation X are irradiated, the predetermined area is preferably appropriately set according to the size of the treatment object part. For example, an area determined fixedly in advance may be used such as an area onto which the direct rays of the radiation X is irradiated in a predetermined proportion (for example, 10%) with respect to the area of the irradiation surface 36A of the radiation detector 36.

In step S1204, the instruction information that instructs to start exposure is transmitted to the radiation irradiating device 18 and the electronic cassette 20. According to this, the radiation source 42 generates the radiation with the tube voltage and the tube current and etc. according to the exposure conditions received by the radiation irradiating device 18 from the console 26 and emits the radiation.

The radiation X that is irradiated from the radiation source 42 transmits the patient 14 through the diaphragm unit 44 and reaches the electronic cassette 20. Thereby, the electric charge is accumulated in the storage capacitor 76 of each pixel portion 80 of the radiation detector 36 that is incorporated in the electronic cassette 20.

The cassette control unit 100 of the electronic cassette 20 controls the gate line driver 88 after a lapse of a previously determined period that is from reception of the instruction information instructing to start the exposure to completion of the accumulation of the electric charge in the storage capacitor 76 of each pixel portion 80 of the radiation detector 36, outputs an ON signal from the gate line driver 88 to each gate line 84 line by line, and sequentially turns on the TFTs 78 connected to each gate line 84 line by line.

When the TFTs 78 connected to each gate line 84 are sequentially turned on line by line, the electric charge accumulated in each storage capacitor 76 as the electric signal sequentially flows to each data line 86 line by line. The electric signal that flows to each data line 86 is converted into digital image information by the signal processing unit 90 and is stored in the line memory 98.

The cassette control unit 100 executes the predetermined image correcting processing on the image information that is stored in the line memory 98 and transmits the image information to the console 26 through the optical communication control unit 102.

The cassette control unit 100 executes the above operation at the speed (30 frame/sec. in this exemplary embodiment) previously set as the movie capturing speed, and controls the display driver 104 such that a radiation image indicated by image information subjected to image correcting processing is displayed by the display 28.

In step 1206, a waiting state is maintained until image information corresponding to one frame is received from the electronic cassette 20. In step 1208, the received image information is stored in the HDD 120. In step 1210, the UI panel control unit 122 is controlled such that a radiation image that is indicated by the received image information is displayed by the display of the UI panel 110 to permit confirmation of the radiation image.

In step 1212, position information that indicates the position of a tip end of the catheter 60 is obtained.

In the console 26 according to this exemplary embodiment, a position specification processing program that time-divisionally specifies the position of the tip end of the catheter 60 is executed by the CPU 114 in parallel with execution of the radiation image capturing processing program.

In the position specification processing program, in a case in which the electric signals that are time-serially received in real time from the reflective photo sensor 62 indicate that regions progress in order of a wide white region, a narrow black region, and a narrow white region in the striped pattern provided in the catheter 60, it is determined that the catheter 60 moves in a direction where the catheter is inserted into the body of the patient 14, and the movement amount at this point in time is specified by multiplying number of appearance of the wide white region by the width of one group of the striped pattern. Likewise, in a case in which the electric signals indicate that regions progress in order of a wide black region, a narrow white region, and a narrow black region in the striped pattern, it is determined that the catheter 60 moves in a direction where the catheter is pulled out from the body of the patient 14, and the movement amount at this point in time is specified by multiplying number of appearance of the wide black region by the width of one group of the striped pattern.

In the position specification processing program, the movement amount when the catheter 60 moves in the direction where the catheter is inserted into the body of the patient 14, which is obtained by the above processing, is integrated, the movement amount when the catheter 60 moves in the direction where the catheter 60 is pulled out from the body of the patient 14 is subtracted, and the insertion amount of the catheter 60 with respect to the body of the patient 14 is specified.

In the position specification processing program, the position of the tip end of the catheter 60 is specified on the basis of the specified insertion amount and the coordinate information indicating the entry scheduled path of the catheter 60 stored in the preparation step of the IVR, and coordinate information (hereinafter, referred to as "tip end coordinate information") indicating the position is stored in a predetermined area of the RAM 118 in real time.

Therefore, in step 1212, the position information that indicates the position of the tip end of the catheter 60 is acquired by reading the stored coordinate information from the RAM 118 by the position specification processing program.

In step 1214, the information that indicates the position of the tip end of the catheter 60 indicated by the acquired position information and the change instruction information that instructs to change the opening state of the diaphragm unit 44 are transmitted to the radiation irradiating device 18.

When the change instruction information is received, in the radiation irradiating device 18, the irradiating device control unit 140 controls the positions of the slit plates 44A to 44D, such that the position corresponding to the position of the tip end of the catheter 60 indicated by the information received together with the change instruction information is the center of the opening region 51. At this time, regarding the shape and the area of the opening region 51, the irradiating device control unit 140 controls the slit plates 44A to 44D to maintain the shape and the area that has been maintained by that time.

In the imaging system 10 according to this exemplary embodiment, the position of the tip end of the catheter 60 is the central position of the region of interest, and the radiation image that includes at least the region of interest is displayed on the display 28 of the electronic cassette 20.

In step 1216, a cumulative exposure dose R in the irradiation field at this point in time is calculated as follows.

First, the cumulative exposure dose R per unit area that is accumulated from a point in time when the medical treatment starts in the irradiation field (hereinafter, referred to as "full irradiation field") of the radiation X in a case in which it is assumed that the opening state of the diaphragm unit 44 is the fully open state to this point in time, is calculated on the basis of factors such as the tube voltage and Focus Skin Distance (FSD) on which the irradiation dose of the radiation X per unit time depends.

Figure 12:
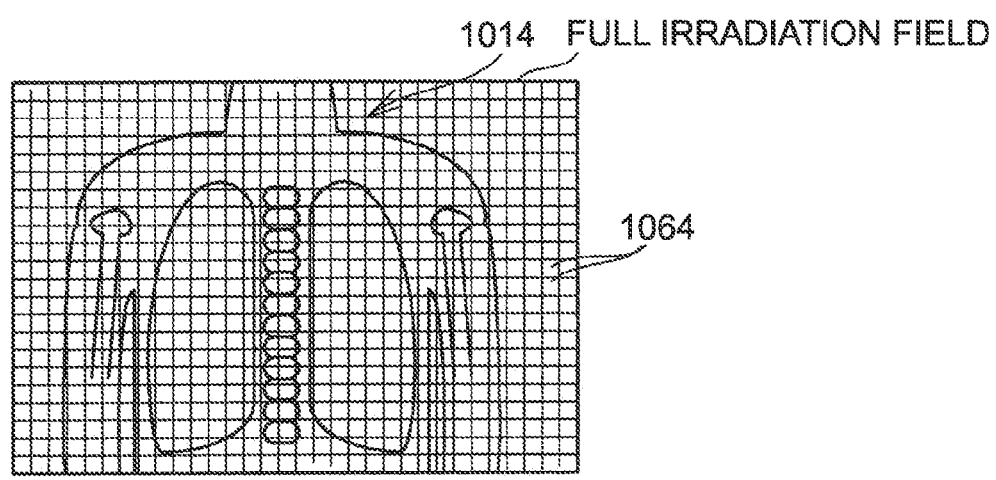
FIG. 12 is a schematic view illustrating calculation of a cumulative exposure dose in the radiation image capturing processing program according to the second exemplary embodiment.

At this time, in the imaging system 10 according to this exemplary embodiment, as schematically shown in FIG. 12, the cumulative exposure dose R is calculated for each rectangular region 1064 by dividing the full irradiation field into plural rectangular regions 1064 each of which is a unit area (1 $cm^2$ in this exemplary embodiment) in a matrix. For example, the cumulative exposure dose R may be calculated using a Non Desimeter Dosimetry (NDD) method.

Among the cumulative exposure doses R calculated for each rectangular region 1064, the cumulative exposure doses R of the rectangular regions 64 that exist in regions where the radiation X is shielded by the slit plates 44A to 44D of the diaphragm unit 44 are converted into the exposure doses attenuated with an attenuate rate according to the thickness of the corresponding slit plates 44A to 44D in a thickness direction.

In step 1218, it is determined whether the cumulative exposure dose R which reaches the exposure dose threshold value of the internal organ positioned at the corresponding position exists in the cumulative exposure doses R for each of the rectangular regions 1064 included in a region (hereinafter, referred to as "region of non-interest of irradiation field") other than the region of interest of the full irradiation field calculated by the processing of step 1216. If the determination result is YES, the processing proceeds to step 1220.

At this time, in step 1218, the names of the internal organs that are included in the coordinate range corresponding to the region of non-interest of irradiation field are specified on the basis of the internal organ coordinate information and the internal organ name information stored in the preparation step of the IVR, and the expose dose threshold value (see FIG. 10) that corresponds to the specified internal organ is read from the HDD 120.

In step 1218, it is determined whether the cumulative exposure dose R reaching the exposure dose threshold value of the internal organ positioned at the corresponding position exists in the cumulative exposure doses R of the rectangular regions 1064 included in the region of non-interest of irradiation field. At this time, in a case in which the internal organ positioned at the corresponding position does not exist, a threshold value that is previously set by the technician as the exposure dose threshold value in the region other than the internal organs is applied. In this case, the exposure dose threshold value in the region other than the internal organs may be previously set for each region having a wider range than the internal organs such as a chest, an abdomen, arms, and legs, and a common threshold value may be set to the entire region of the region other than the internal organs.

In step S1220, the shape and the area of the opening region 51 of the diaphragm unit 44 are derived to be a shape and an area where the direct rays are irradiated onto at least the region of interest and an added value of the exposure doses with respect to the rectangular regions 1064 whose cumulative exposure doses R reach the exposure dose threshold value, among the rectangular regions 1064 included in the region of non-interest of irradiation field, is minimized in regards to the region of non-interest.

In step 1222, information that indicates the shape and the area of the opening region 51 derived by the processing of step 1220 and the change instruction information that instructs to change the opening state of the diaphragm unit 44 are transmitted to the radiation irradiating device 18. Then, the processing proceeds to step 1230.

When the change instruction information is received, in the radiation irradiating device 18, the irradiating device control unit 140 controls the positions of the slit plates 44A to 44D to be the shape and the area indicated by the information received together with the change instruction information.

Meanwhile, if the determination result is NO in step 1218, the processing proceeds to step 1224, and it is determined whether the cumulative exposure doses R of all of the rectangular regions 1064 included in the region of non-interest of irradiation field are less than the exposure dose obtained by subtracting the predetermined margin exposure dose from the exposure dose threshold value of the internal organ positioned at the corresponding position. If the determination result is NO, the processing proceeds to step 1230 to be described below. Meanwhile, if the determination result is YES, the processing proceeds to step 1226.

At this time, in step 1224, the names of the internal organs that are included in the coordinate range corresponding to the region of non-interest of irradiation field are specified on the basis of the internal organ coordinate information and the internal organ name information stored in the preparation step of the IVR, and the expose dose threshold value (see FIG. 10) that corresponds to the specified internal organ is read from the HDD 120.

In step 1224, it is determined whether the cumulative exposure doses R of all of the rectangular regions 1064 included in the region of non-interest of irradiation field are less than the exposure dose obtained by subtracting the predetermined margin exposure dose from the exposure dose threshold value of the internal organ positioned at the corresponding position. Even at this time, if the internal organ positioned at the corresponding position does not exist, similar to the processing of step 1218 described above, a threshold value that is previously set by the technician as the exposure dose threshold value in the region other than the internal organs is applied.

In step 1226, the shape and the area of the opening region 51 of the diaphragm unit 44 are derived to be a shape and an area where the direct rays are irradiated onto at least the region of interest and an added value of the exposure doses with respect to the rectangular regions 1064 in a range in which the cumulative exposure doses R do not reach the corresponding exposure dose threshold value with respect to all of the rectangular regions 1064 included in the region of non-interest of irradiation field is maximized in regards to the region of non-interest.

In step 1228, information that indicates the shape and the area of the opening region 51 derived by the processing of step 1226 and the change instruction information that instructs to change the opening state of the diaphragm unit 44 are transmitted to the radiation irradiating device 18. Then, the processing proceeds to step 1230.

When the change instruction information is received, in the radiation irradiating device 18, the irradiating device control unit 140 controls the positions of the slit plates 44A to 44D to be the shape and the area indicated by the information received together with the change instruction information.

In step 1230, it is determined whether a timing at which capturing of the radiation image ends has come. If the determination result is NO, the processing returns to step 1206. At a point in time when the determination result is YES, the processing proceeds to step 1232. In the radiation image capturing processing program according to this exemplary embodiment, whether the timing at which capturing of the radiation image ends has come in step 1230 is determined by determining whether the technician inputs instruction information instructing to end capturing of the radiation image through the input unit such as the operation panel 112. However, the invention is not limited thereto and another form may be used. For example, it may be determined by determining whether a power supply switch (not shown in the drawings) of the electronic cassette 20 or the radiation irradiating device 18 is turned off.

In step 1232, instruction information that instructs to stop the exposure started by the processing of step 1204 is transmitted to the radiation irradiating device 18 and the electronic cassette 20. In step 1234, after the image information stored by the processing of step 1208 is transmitted to a Radiology Information System (RIS) server (not shown in the drawings) through an in-hospital network (not shown in the drawings), the radiation image capturing processing program ends. In the RIS server, a doctor may be interpret or diagnose the radiation image that is captured using the image information received from the console 26.

FIG. 8 shows an example of a radiation image that is displayed on the display surface 28A of the display 28 by irradiating the radiation X onto an entire surface of an irradiation surface 36A of the radiation detector 36 according to this exemplary embodiment. FIG. 9 shows an example of a radiation image in a case in which the patient 14 lies in substantially the same state as the state shown in FIG. 8, which is displayed on the display surface 28A of the display 28 by executing the radiation image capturing processing program according to this exemplary embodiment and irradiating radiation onto a partial region of the irradiation surface 36A of the radiation detector 36.

As shown in FIG. 9, in the imaging system 10 according to this exemplary embodiment, since the irradiation region of the direct rays of the radiation X may be restricted to the predetermined region (a region including a region of interest in this exemplary embodiment), the exposure dose with respect to the patient 14 may be suppressed. In addition, the image according to the transmission dose of the position of the corresponding slit plate is displayed as an example in the state shown in FIG. 9 with respect to the region (gradation region in the display image of FIG. 9) of the peripheral part of the predetermined region. Therefore, a radiation image of the peripheral part may be observed.

As described in detail above, according to this exemplary embodiment, in a case in which the accumulative exposure dose (cumulative exposure dose R in this exemplary embodiment) from a point in time when the medical treatment using the radiation irradiated from the radiation source to the subject (patient 14 in this exemplary embodiment) to capture the movie of the radiation image reaches the predetermined exposure dose, the exposure dose with respect to the irradiation field of the radiation from the radiation source other than the region of interest is controlled to be restricted. Therefore, the exposure dose with respect to the subject may be suppressed while a quality of the radiation image in the region of interest may be prevented.

In this exemplary embodiment, the imaging system includes the diaphragm unit (diaphragm unit 44 in this exemplary embodiment) that is provided between the radiation source and the subject and that has the opening region configured to transmit a part of the radiation emitted from the radiation source and have an area to be changed, and the diaphragm unit is controlled to restrict the exposure dose by changing the area of the opening region of the diaphragm unit. Therefore, the region of the irradiation field other than the region of interest may be changed and convenience may be improved.

In particular, in this exemplary embodiment, the diaphragm unit is configured such that the transmission dose of the radiation decreases as the distance from the circumferential part of the opening region increases. Therefore, the radiation image in the irradiation field excluding the region of interest may be observed.

In this exemplary embodiment, since the cumulative exposure dose is calculated for each of the divided regions each of which is the predetermined unit area in the irradiation field, the exposure dose with respect to the subject may be precisely restricted, as compared with the case where the cumulative exposure doses are collected and calculated over the entire region of the irradiation field.

In this exemplary embodiment, the control is performed following the region of interest changing with the passage of time. Therefore, convenience may be improved.

In particular, the position of the predetermined part of the medical apparatus (catheter 60 in this exemplary embodiment) that is inserted into the body of the subject is specified, and the specified position is controlled as the region of interest. Therefore, the region of interest does not need to be previously set and convenience may be improved.

The sensitivity of CsI which is used as the scintillator 304 changes as a temperature changes as shown in FIG. 26. For example, the sensitivity lowers about 0.3% if a temperature rises one degree. The sensitivity of GOS hardly changes as a temperature changes.

Circuits and elements such as the power supply unit 106, the gate line driver 88 and the signal processing unit 90 in the electronic cassette 20 generate heat by capturing images. Further, if a movie is captured by the IVR, a capturing time is long. Thus, in the electronic cassette 20 which uses CsI as the scintillator 304, there are cases in which the sensitivity of the scintillator 304 is lowered by heat from the circuits and elements when capturing a movie. The technician who performs IVR increases a radiation dose to be irradiated if the technician wishes to maintain an image quality necessary for diagnosis. However, if the radiation dose increases, an exposure dose to a patient will increase. In the present embodiment, the diaphragm unit is configured such that the transmission dose of the radiation decreases as the distance from the circumferential part of the opening region increases, and thus, an increase in exposure dose with respect to the patient can be suppressed.

The sensitivity of CsI lowers as the cumulative exposure dose increases when capturing images continuously, and when a condition in which a radiation is not irradiated is maintained, the sensitivity which has lowered recovers, as shown in FIG. 27. In a case in which a movie is captured by IVR or the like, an imaging time is long. In a case in which static images are captured frequently when capturing a movie, an irradiation amount of radiation for capturing a static image is about 10-100 times that per one frame in capturing a movie, and thus, the sensitivity of the scintillator 304 lowers as the cumulative exposure dose increases. In this case, if a technician wishes to maintain an image quality necessary for diagnosis, the technician increases the radiation dose to be irradiated. However, if the radiation dose increases, an exposure dose to a patient will increase. In the present embodiment, the diaphragm unit is configured such that the transmission dose of the radiation decreases as the distance from the circumferential part of the opening region increases, and thus, an increase in exposure dose with respect to the patient can be suppressed.

In the present embodiment, the diaphragm unit is configured such that the transmission dose of the radiation decreases as the distance from the circumferential part of the opening region increases, and thus, an increase in exposure dose with respect to the patient can be suppressed even if the radiation dose of the radiation X to be irradiated is increased accompanying a decrease in the sensitivity of the scintillator 304.

Since the region of interest is an operation portion, it is necessary to maintain an image quality of the region of interest. However, an influence is small even if a captured image of a region other than the region of interest is a little noisy. Therefore, in a case in which the exposure dose with respect to the irradiation field other than the region of interest is restricted if it is determined that the cumulative exposure dose R reaches the predetermined exposure dose, control may be performed to amplify the operational amplifier 92A of the sample hold circuit 92 which reads an image of the region to which the restriction is applied to an extent which is not usually used and reduce the maximum exposure dose.

Third Exemplary Embodiment

Figure 13:
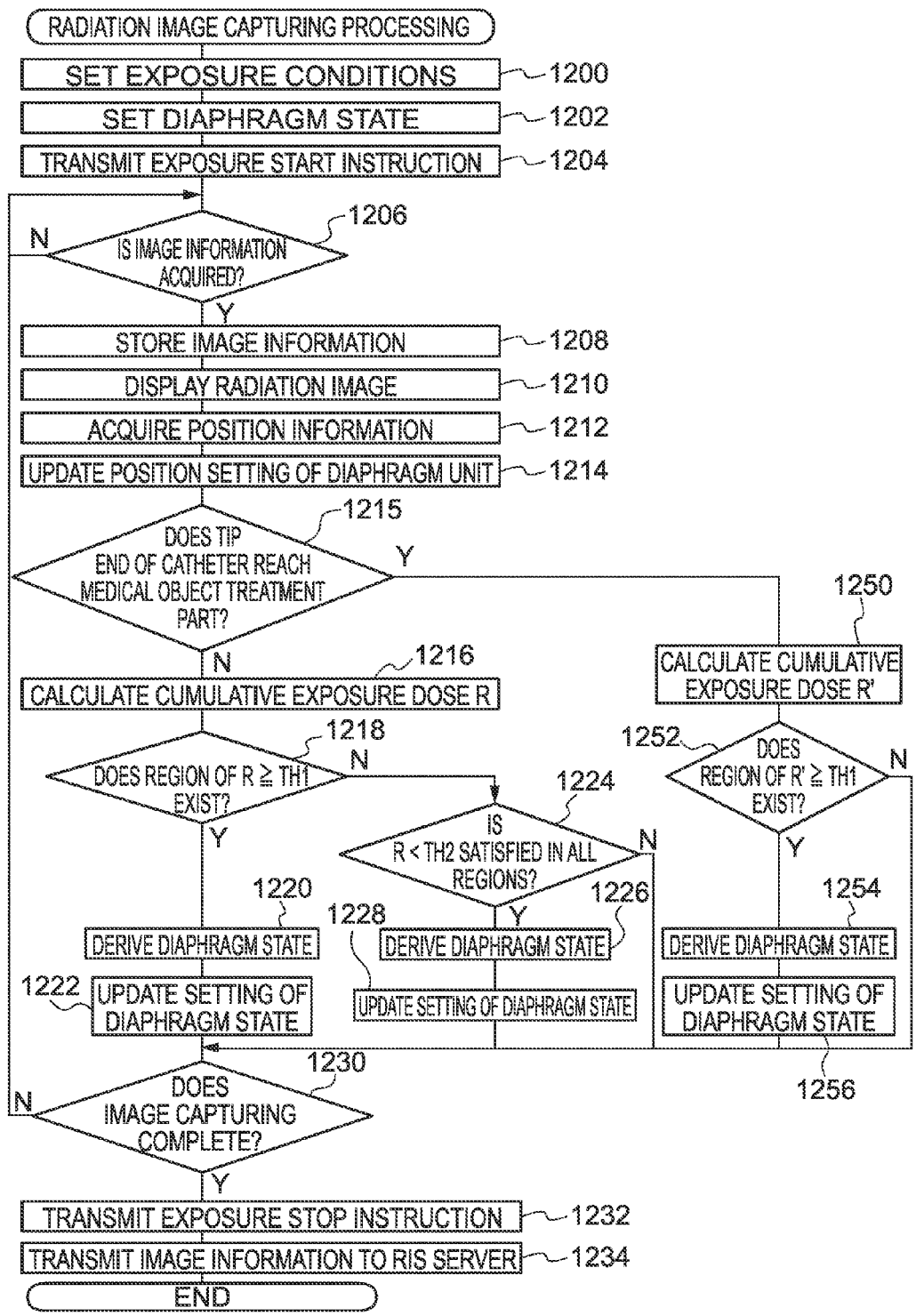
FIG. 13 is a flowchart illustrating a processing flow of a radiation image capturing processing program according to a third exemplary embodiment.

In the third exemplary embodiment, an example of the case where the cumulative exposure dose with respect to the irradiation field from a point in time when the medical treatment starts to a point in time when capturing of the movie ends is calculated and applied will be described. Since the configuration of the imaging system 10 according to the third exemplary embodiment is the same as that of the imaging system according to the first exemplary embodiment, the description will not be repeated. A function of the console 26 according to the third exemplary embodiment when the radiation image capturing processing is executed will be described with reference to FIG. 13. FIG. 13 is a flowchart illustrating a processing flow of the radiation image capturing processing program that is executed by the CPU 114 of the console 26 at this point in time. In FIG. 13, the steps that execute the same processing as those of FIG. 11 are denoted by the same step numbers and the description will not be repeated. The case where a lesion part to be a medical treatment object and a medical treatment time are previously set will be described.

In step 1215 of FIG. 13, it is determined whether the tip end of the catheter 60 reaches the lesion part reaches the medical treatment object. If the determination result is NO, the processing proceeds to step 1216. Meanwhile, if the determination result is YES, the processing proceeds to step 1250.

In step 1250, on the basis of the cumulative exposure dose R at this point in time, a cumulative exposure dose R' in the irradiation field of the radiation X from a point in time when the medical treatment starts to a point in time when the capturing of the movie ends is calculated as follows.

First, by the similar processing as step 1216, the cumulative exposure dose R until this point in time is calculated, and a time (hereinafter, referred to as "remaining medical treatment time") from this point in time to a point in time when the medical treatment ends is calculated. On the assumption that the exposure conditions at this point in time are maintained, the cumulative exposure dose for each of the rectangular regions 1064 while the remaining medical treatment time passes is calculated in the similar way as the cumulative exposure dose R, the cumulative exposure R is added for each of the rectangular regions 1064 and thereby the cumulative exposure dose R' is calculated.

In step 1252, it is determined whether the cumulative exposure dose R' reaching the exposure dose threshold value of the internal organ positioned at the corresponding position exists in the cumulative exposure doses R' for the rectangular regions 1064 that are included in the region (region of non-interest of irradiation field) other than the region of interest of the full irradiation field calculated by the processing of step 1250 described above. If the determination result is NO, the processing proceeds to step 1230. Meanwhile, if the determination result is YES, the processing proceeds to step 1254.

At this time, in step 1252, the names of the internal organs that are included in the coordinate range corresponding to the region of non-interest of irradiation field are specified on the basis of the internal organ coordinate information and the internal organ name information stored in the preparation step of the IVR, and the expose dose threshold value (see FIG. 10) that corresponds to the specified internal organ is read from the HDD 120.

In step 1252, it is determined whether the cumulative exposure dose R' reaching the exposure dose threshold value of the internal organ positioned at the corresponding position exists in the cumulative exposure doses R' of the rectangular regions 1064 included in the region of non-interest of irradiation field. At this time, if the internal organ positioned at the corresponding position does not exist, a threshold value that is previously set by the technician as the exposure dose threshold value in the region other than the internal organs is applied, similar to the processing of step 1218.

In step 1254, the shape and the area of the opening region 51 of the diaphragm unit 44 are derived to be a shape and an area where the direct rays are irradiated onto at least the region of interest and an added value of the exposure doses with respect to the rectangular regions 1064 whose cumulative exposure doses R' reach the corresponding exposure dose threshold value, among the rectangular regions 1064 included in the region of non-interest of irradiation field, is minimized in regards to the region of non-interest.

In step 1256, information that indicates the shape and the area of the opening region 51 derived by the processing of step 1254 and the change instruction information that instructs to change the opening state of the diaphragm unit 44 are transmitted to the radiation irradiating device 18. Then, the processing proceeds to step 1230.

When the change instruction information is received, in the radiation irradiating device 18, the irradiating device control unit 140 controls the positions of the slit plates 44A to 44D to be the shape and the area indicated by the information received together with the change instruction information.

As described in detail above, in this exemplary embodiment, in addition to the effect according to the second exemplary embodiment, the cumulative exposure dose with respect to the irradiation field from a point in time when the medical treatment starts to a point in time when the capturing of the movie ends is calculated as the cumulative exposure dose. Therefore, the cumulative exposure dose that is accumulated by a point in time that the capturing of the movie in the irradiation field other than the region of interest ends may be restricted to the predetermined exposure dose or less.

Fourth Exemplary Embodiment

Since the configuration of an imaging system 10 according to the fourth exemplary embodiment is the same as that of the first exemplary embodiment, the description will not be repeated.

In the imaging system 10 according to this exemplary embodiment, an exposure dose restriction function that restricts an exposure dose with respect to an irradiation field other than the region of interest of the radiation X, in a case in which a cumulative exposure dose per unit area (1 cm$^2$ in this exemplary embodiment) in the patient 14 reaches a predetermined exposure dose threshold value, is mounted. For this reason, in the imaging system 10 according to this exemplary embodiment, information (hereinafter, referred to as "exposure dose threshold value information") that indicates the exposure dose threshold value, information (hereinafter, referred to as "exposure dose history information") that indicates a history of the exposure dose, and information (hereinafter, referred to as "weight value management information") that indicates a weight value used when the cumulative exposure dose is calculated are previously stored in the HDD 120 of the console 42.

FIG. 10 schematically shows an example of the exposure dose threshold value information. As shown in FIG. 10, in the exposure dose threshold value information according to this exemplary embodiment, the exposure dose threshold value is stored for each kind of internal organs such as a heart, lungs, and a stomach. The exposure dose threshold value information may be set on the basis of Guideline for Medical Exposure suggested by Japan Association of Radiological Technicians.

Meanwhile, FIG. 14 schematically shows an example of the exposure dose history information. As shown in FIG. 14, in the exposure dose history information according to this exemplary embodiment, each information of an Identification (ID), an image capturing date and time, an exposure region, an exposure dose, an exposure period, and a frame rate is stored in each patient.

The ID is information that specifies the corresponding patient, and information that is previously given as different information is used for each patient. The image capturing date and time are information that indicate a date and time when the radiation image is captured with respect to the corresponding patient, and the exposure region is information that indicates a region of the corresponding patient irradiated with the radiation X.

In the imaging system 10 according to this exemplary embodiment, as schematically shown in FIG. 12 as an example, the irradiation field (hereinafter, referred to as "full open irradiation field") of the radiation when the opening state of the diaphragm unit 44 is set as a full open state is divided into plural rectangular regions 1064 each of which is a unit area (1 cm$^2$ in this exemplary embodiment) in a matrix, and the cumulative exposure dose that is applied in the exposure doe restriction function is calculated for each of the rectangular regions 1064.

The exposure region is coordinate information that indicates the position of the rectangular region 1064 corresponding to the position where the radiation X is irradiated, the exposure dose is information that indicates the exposure dose of the radiation X with respect to the corresponding exposure region, and the exposure period is information that indicates a period were the radiation X of the corresponding exposure dose is irradiated onto the corresponding exposure region. In the imaging system 10 according to this exemplary embodiment, coordinate information of an X-Y coordinate system that is based on the rectangular region 1064 positioned at an upper left corner point in the full open irradiation field shown in FIG. 12 is applied as the coordinate information. However, the invention is not limited thereto.

The frame rate is information that indicates a frame rate when the movie of the radiation image of the corresponding patient is captured at the corresponding date and time. In the imaging system 10 according to this exemplary embodiment, 15 (fps) or 30 (fps) is selectively applied.

In the imaging system according to this exemplary embodiment, each of the exposure region, the exposure dose, and the exposure period is stored for each frame (one image) in the capturing of the movie of the radiation image.

In the example shown in FIG. 14, a movie of the ration image is captured with respect to the patient given with an ID of "01-001" during a period from 14:20 to 14:30 in the same day of 2010-02-16. At this time, the exposure region, the exposure dose, and the exposure period are stored for each frame and the frame rate of 15 (fps) is stored, as shown in FIG. 14.

Meanwhile, FIG. 15 schematically shows an example of the weight value management information. As shown in FIG. 15, the weight value management information according to this exemplary embodiment is configured by previously storing information of each of a parameter, a condition, and a weight value.

The parameter is a parameter that is applied when a weight value with respect to the past cumulative exposure dose is determined, the condition is information that indicates a range of the parameter, and the weight value is information that indicates a weight value in a case in which the parameter is matched with the corresponding condition.

As the example shown in FIG. 15, a passage period t (min) until a current point in time after the radiation X is irradiated is applied as the parameter. If the passage period t is less than 1440 (min), "1" that is the maximum value as the weight value is applied. If the passage period t is less than 10080 (min), "0.9" is applied.

Next, a function of the imaging system 10 according to this exemplary embodiment will be described.

In a case in which the IVR is executed on the patient 14 using the imaging system 10 according to this exemplary embodiment, the technician that executes the IVR first inputs the coordinate information indicating an entry scheduled path of the catheter 60 as follows, as a preparing step of the IVR.

That is, first, the technician causes the patient 14 to lie on the object table 16A, such that a predetermined reference part (top part of a head in this exemplary embodiment) is positioned at the predetermined reference position for each patient in the object table 16A. Next, the technician causes the radiation irradiating device 18 to change states of the slit plates 44A to 44D of the diaphragm unit 44 to fully open states through the console 26, and controls the radiation source 42 to emit the radiation X with a predetermined exposure dose. Meanwhile, the technician controls the electronic cassette 20 to capture a radiation image. Thereby, in the electronic cassette 20, the radiation image is captured as be described below about a radiation image capturing processing (see FIG. 16), and image information that is obtained by capturing the image is transmitted to the console 26. Meanwhile, when the image information is received, the console 26 displays the radiation image, which is indicated by the image information, on the display of the UI panel 110.

Therefore, the technician traces the entry scheduled path of the catheter 60 in the body of the patient 14 on the radiation image displayed on the display of the UI panel 110 with the touch pen, and thereby inputs coordinate information (hereinafter, referred to as "path coordinate information") of the entry scheduled path. At this time, the technologies traces the contour of an internal organ (hereinafter, referred to as "determination object internal organ) that exists in the entry scheduled path and a region be an irradiation field of the radiation X in the vicinity of the entry scheduled path with the touch pen, inputs coordinate information (hereinafter, referred to as "internal organ coordinate information") indicating the region where the determination object internal organ exists, and inputs information (hereinafter, referred to as "internal organ name information") indicating each name of the determination object internal organ existing in the region indicated by the internal organ coordinate information through the operation panel 112. The path coordinate information and the internal organ coordinate information are coordinate information of the same X-Y coordinate system as the coordinate information indicating the exposure region described above.

The path coordinate information, the internal organ coordinate information, and the internal organ name information that are input from the technician in the above-described way are stored in the HDD 120 in a state where the internal organ coordinate information and the internal organ name information corresponding to each other are associated by the console 26.

If the above preparation step ends, the technician performs an exposure condition designating operation to designate exposure conditions such as a tube voltage and a tube current when the radiation X is irradiated through the operation panel 112 of the console 26, according to the imaging part or the imaging condition of the patient 14, and performs an instruction operation to instruct to start execution of the IVR.

When the instruction operation is performed, the console 26 executes the radiation image capturing processing.

Figure 16:
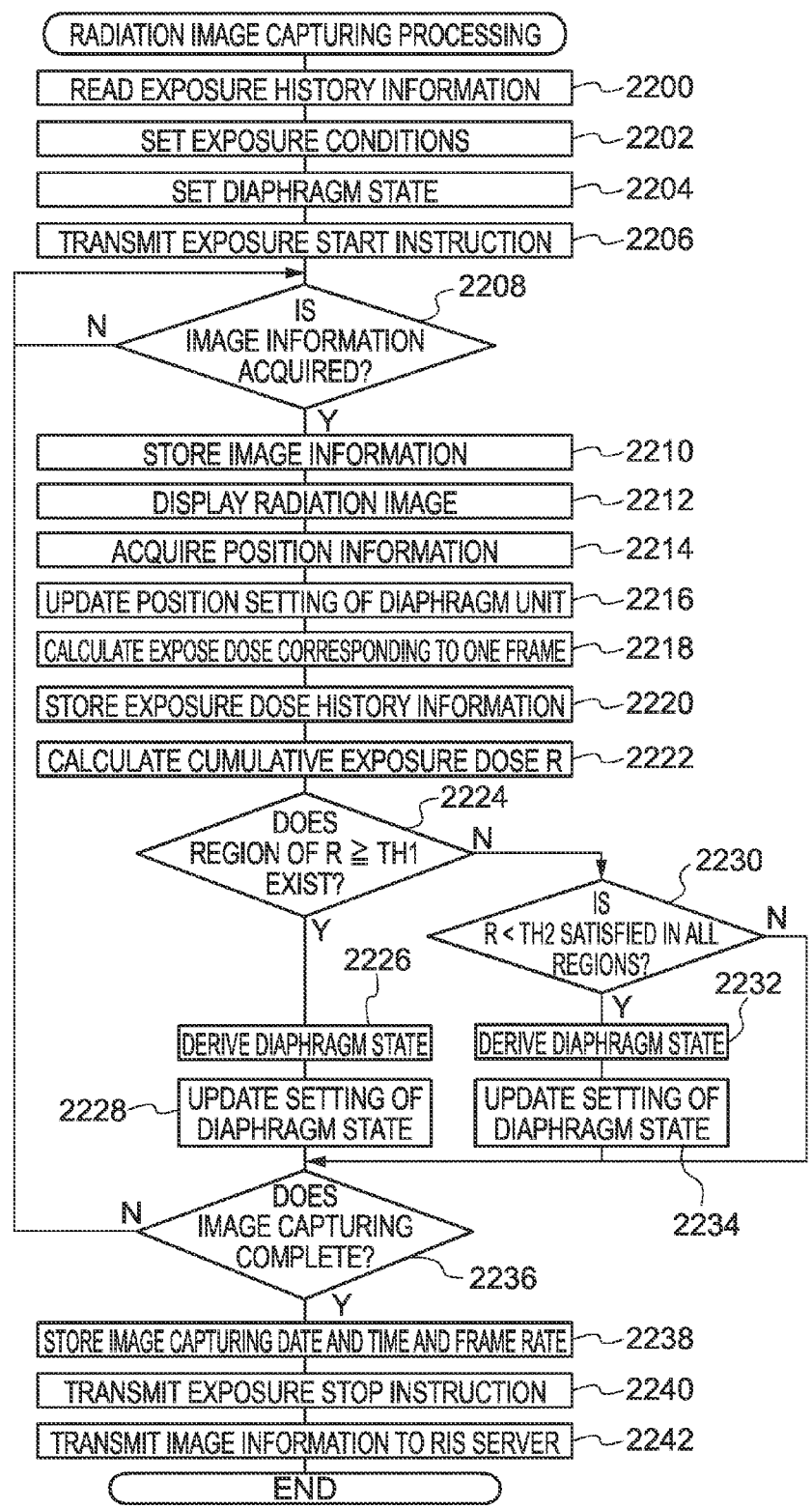
FIG. 16 is a flowchart illustrating a processing flow of a radiation image capturing processing program according to the fourth exemplary embodiment.

Next, a function of the console 26 when the radiation image capturing processing is executed will be described with reference to FIG. 16. FIG. 16 is a flowchart illustrating a processing flow of a radiation image capturing processing program that is executed by the CPU 114 of the console 26 at this point in time. The program is previously stored in a predetermined area of the ROM 116. Here, the case where an ID of the patient 14 to be a medical treatment object is previously set by the technician will be described.

In step 2200 of FIG. 16, each information of the image capturing date and time, the exposure region, the exposure dose, and the exposure period that correspond to the ID of the patient 14 to be previously set is read from the exposure dose history information of the HDD 120. In step 2202, the exposure conditions that are designated by the technician are transmitted to the radiation irradiating device 18 and the electronic cassette 20 and the exposure conditions are set. According to this, the irradiating device control unit 140 performs an exposure preparation under the received exposure conditions. The information that is related to the patient 14 to be the medical treatment object may not be stored in the exposure dose history information. However, in this case, individual information does not need to be read in step 2200.

In step 2204, the information that indicates the position of the insertion opening of the catheter 60 indicated by the path coordinate information stored in the preparation step of the IVR and the setting instruction information that instructs setting of the opening state of the diaphragm unit 44 are transmitted to the radiation irradiating device 18.

When the setting instruction information is received, in the radiation irradiating device 18, the irradiating device control unit 140 controls the positions of the slit plates 44A to 44D, such that the position corresponding to the position of the insertion opening of the catheter 60 indicated by the information received together with the setting instruction information is the center of the opening region 51, a shape of the opening region 51 is a predetermined shape, and an area of the opening region 51 is a predetermined area previously set as an area which is narrower than an area of the fully open state. In the imaging system 10 according to this exemplary embodiment, as the predetermined shape and the predetermined area, a shape and an area are applied, which are previously set by the technician as a shape and an area in which a region (hereinafter, referred to as "direct ray irradiation field") of the patient 14 where the direct rays of the radiation X are irradiated includes at least a region of interest.

Since the predetermined area is the area where the direct rays of the radiation X are irradiated, the predetermined area is preferably appropriately set according to the size of the treatment object part. For example, an area determined fixedly in advance may be used such as an area onto which the direct rays of the radiation X are irradiated to the predetermined ratio (for example, 10%) with respect to the area of the irradiation surface 36A of the radiation detector 36.

In step S2206, the instruction information that instructs to start exposure is transmitted to the radiation irradiating device 18 and the electronic cassette 20. According to this, the radiation source 42 generates the radiation with the tube voltage and the tube current and etc. according to the exposure conditions received by the radiation irradiating device 18 from the console 26 and emits the radiation.

The radiation X that is irradiated from the radiation source 42 transmits the patient 14 through the diaphragm unit 44 and reaches the electronic cassette 20. Thereby, the electric charge is accumulated in the storage capacitor 76 of each pixel portion 80 of the radiation detector 36 that is incorporated in the electronic cassette 20.

The cassette control unit 100 of the electronic cassette 20 controls the gate line driver 88 after a passage of a period previously determined as a period until the accumulation of the electric charge in the storage capacitor 76 of each pixel portion 80 of the radiation detector 36 ends after the instruction information instructing to start the exposure is received, outputs an ON signal from the gate line driver 88 to each gate line 84 line by line, and sequentially turns on the TFTs 78 connected to each gate line 84 line by line.

If the TFTs 78 connected to each gate line 84 are sequentially turned on line by line, the electric charge accumulated in each storage capacitor 76 as the electric signal sequentially flows to each data line 86 line by line. The electric signal that flows to each data line 86 is converted into digital image information by the signal processing unit 90 and is stored in the line memory 98.

The cassette control unit 100 executes the predetermined image correcting processing on the image information that is stored in the line memory 98 and transmits the image information to the console 26 through the optical communication control unit 102.

The cassette control unit 100 repetitively executes the above operation at the speed (15 (fps) or 30 (fps) in this exemplary embodiment) previously determined by the technician as the movie capturing speed (frame rate), and controls the display driver 104 such that a radiation image indicated by image information subjected to image correcting processing is displayed by the display 28.

In step 2208, a waiting state is maintained until image information corresponding to one frame is received from the electronic cassette 20. In step 2210, the received image information is stored in the HDD 120. In step 2212, the cassette control unit 100 controls the UI panel control unit 122 such that a radiation image that is indicated by the received image information is displayed by the display of the UI panel 110 to confirm the radiation image.

In step 2214, position information that indicates the position of a tip end of the catheter 60 is obtained.

In the console 26 according to this exemplary embodiment, a position specification processing program that time-divisionally specifies the position of the tip end of the catheter 60 in parallel with the radiation image capturing processing program is executed by the CPU 114.

In the position specification processing program, in a case in which the electric signals that are time-serially received in real time from the reflective photo sensor 62 indicate that regions progress in order of a wide white region, a narrow black region, and a narrow white region in the striped pattern provided in the catheter 60, it is determined that the catheter 60 moves in a direction where the catheter is inserted into the body of the patient 14, and the movement amount at this point in time is specified by multiplying number of appearance of the wide white region by the width of one group of the striped pattern. Likewise, in a case in which the electric signals indicate that regions progress in order of a wide black region, a narrow white region, and a narrow black region in the striped pattern, it is determined that the catheter 60 moves in a direction where the catheter is pulled out from the body of the patient 14, and the movement amount at this point in time is specified by multiplying number of appearance of the wide black region by the width of one group of the striped pattern.

In the position specification processing program, the movement amount when the catheter 60 moves in the direction where the catheter is inserted into the body of the patient 14, which is obtained by the above processing, is integrated, the movement amount when the catheter 60 moves in the direction where the catheter is pulled out from the body of the patient 14 is subtracted, and the insertion amount of the catheter 60 with respect to the body of the patient 14 is specified.

In the position specification processing program, the position of the tip end of the catheter 60 is specified on the basis of the specified insertion amount and the coordinate information indicating the entry scheduled path of the catheter 60 stored in the preparation step of the IVR, and coordinate information (hereinafter, referred to as "tip end coordinate information") indicating the position is stored in a predetermined area of the RAM 118 in real time.

Therefore, in step 2214, the position information that indicates the position of the tip end of the catheter 60 is acquired by reading the stored coordinate information from the RAM 118 by the position specification processing program.

In step 2216, the information that indicates the position of the tip end of the catheter 60 indicated by the acquired position information and the change instruction information that instructs to change the opening state of the diaphragm unit 44 are transmitted to the radiation irradiating device 18.

When the change instruction information is received, in the radiation irradiating device 18, the irradiating device control unit 140 controls the positions of the slit plates 44A to 44D, such that the position corresponding to the position of the tip end of the catheter 60 indicated by the information received together with the change instruction information is the center of the opening region 51. At this time, the irradiating device control unit 140 controls the slit plates 44A to 44D to maintain the shape and the area of the opening region 51 until now.

In the imaging system 10 according to this exemplary embodiment, the position of the tip end of the catheter 60 is the central position of the region of interest, and the radiation image that includes at least the region of interest is displayed on the display 28 of the electronic cassette 20 by the processing of step 2216.

In step 2218, the exposure dose with respect to the patient 14 when the image information corresponding to one frame received from the electronic cassette 20 is obtained in step 2208 is calculated as follows.

First, the exposure dose r per unit area of a capturing period of one frame in the irradiation field (hereinafter, referred to as "full irradiation field") of the radiation X in a case in which it is assumed that the opening state of the diaphragm unit 44 is the fully open state is calculated on the basis of factors such as the tube voltage and focus skin distance (FSD) on which the irradiation dose of the radiation X per unit time depends. At this time, in the imaging system 10 according to this exemplary embodiment, the exposure dose r is calculated for rectangular regions 1064. For example, the exposure dose r may be calculated using a Non Desimeter Dosimetry (NDD) method.

Among the exposure doses r calculated for each rectangular region 1064, the exposure doses r of the rectangular regions 64 that exist in the regions where the radiation X is shielded by the slit plates 44A to 44D of the diaphragm unit 44 are converted into the exposure doses attenuated with an attenuate rate according to the thickness of the corresponding slit plates 44A to 44D in a height direction.

In step 2220, the exposure dose r for each rectangular region 1064 that is calculated by the processing of step 2218 and the exposure period of the radiation X and the coordinate information (exposure region) that indicates the position of the corresponding rectangular region 1064 are associated with the ID of the patient 14 to be a medical treatment object, are added to the exposure dose history information, and are stored (registered). At this time, an exposure period corresponding to one frame according to a frame rate that is previously set (15 (fps) or 30 (fps) in this exemplary embodiment) by the technician is applied as the exposure period.

In step 2222, the cumulative exposure dose R in the irradiation field of the radiation X at this point in time is calculated as follows.

That is, first, all conditions and weight values are read from the weight value management information of the HDD 120. Meanwhile, the past exposure dose with respect to the patient 14 to be a medical treatment object that is indicated by the information read by the processing of step 2200 is added for each image capturing date and time and each rectangular region 1064.

Next, after the exposure dose obtained by the above processing is multiplied with the weight value corresponding to the progress period corresponding to each medical treatment, the exposure dose after the weight value for each medical treatment is multiplied is added for each of the rectangular regions 1064. The progress period may be calculated by deriving a progress period until a current point in time from a time (image capturing end time in this exemplary embodiment) indicated by the corresponding image capturing date and time.

The exposure dose obtained by the above processing and an added value of the exposure doses r stored in the exposure dose history information for each of the rectangular regions 1064 by the processing of step 2220 in this medical treatment are added for each of the rectangular regions 1064, and the cumulative exposure dose R for each of the rectangular regions 1064 is calculated.

In a case in which the information is not read in step 2200, the added value of the exposure doses r stored in the exposure dose history information for each of the rectangular regions 1064 by the processing of step 2200 in this medical treatment is calculated as the cumulative exposure dose R for each of the rectangular regions 1064, in step 2222.

In step 2224, it is determined whether the cumulative exposure dose R reaching the exposure dose threshold value of the internal organ positioned at the corresponding position exists in the cumulative exposure doses R for each of the rectangular regions 1064 included in a region (hereinafter, referred to as "region of non-interest of irradiation field") other than the region of interest of the full irradiation field calculated by the processing of step 2222. If the determination result is YES, the processing proceeds to step 2226.

At this time, in step 2224, the names of the internal organs that are included in the coordinate range corresponding to the region of non-interest of irradiation field are specified on the basis of the internal organ coordinate information and the internal organ name information stored in the preparation step of the IVR, and the exposure dose threshold value (see FIG. 10) that corresponds to the specified internal organ is read from the HDD 120.

In step 2224, it is determined whether the cumulative exposure dose R reaching the exposure dose threshold value of the internal organ positioned at the corresponding position exists in the cumulative exposure doses R of the rectangular regions 1064 included in the non-region of interest of irradiation field. At this time, in a case in which the internal organ positioned at the corresponding position does not exist, a threshold value that is previously set by the technician as the exposure dose threshold value in the region other than the internal organs is applied. In this case, the exposure dose threshold value in the region other than the internal organs may be previously set for each region having a wider range than the internal organs such as a chest, an abdomen, arms, and legs, and a common threshold value may be set to the entire region of the region other than the internal organs.

In step 2226, the shape and the area of the opening region 51 of the diaphragm unit 44 are derived to be a shape and an area where the direct rays are irradiated onto at least the region of interest and an added value of the exposure doses with respect to the rectangular regions 1064 whose cumulative exposure doses R reach the exposure dose threshold value, among the rectangular regions 1064 included in the region of non-interest of irradiation field, is minimized in regards to the region of non-interest.

In step 2228, information that indicates the shape and the area of the opening region 51 derived by the processing of step 2226 and the change instruction information that instructs to change the opening state of the diaphragm unit 44 are transmitted to the radiation irradiating device 18. Then, the process proceeds to step 2236.

When the change instruction information is received, in the radiation irradiating device 18, the irradiating device control unit 140 controls the positions of the slit plates 44A to 44D to be the shape and the area indicated by the information received together with the change instruction information.

Meanwhile, if the determination result is NO in step 2224, the process proceeds to step 2230, and it is determined whether the cumulative exposure doses R of all of the rectangular regions 1064 included in the region of non-interest of irradiation field are less than the exposure dose obtained by subtracting the predetermined margin exposure dose from the exposure dose threshold value of the internal organ positioned at the corresponding position. If the determination result is NO, the process proceeds to step 2236 to be described below. Meanwhile, if the determination result is YES, the process proceeds to step 2232.

At this time, in step 2230, the names of the internal organs that are included in the coordinate range corresponding to the region of non-interest of irradiation field are specified on the basis of the internal organ coordinate information and the internal organ name information stored in the preparation step of the IVR, and the exposure dose threshold value (see FIG. 10) that corresponds to the specified internal organ is read from the HDD 120.

In step 2230, it is determined whether the cumulative exposure doses R of all of the rectangular regions 1064 included in the region of non-interest of irradiation field are less than the exposure dose obtained by subtracting the predetermined margin exposure dose from the exposure dose threshold value of the internal organ positioned at the corresponding position. Even at this time, in a case in which the internal organ positioned at the corresponding position does not exist, similar to the process of step 2224 described above, a threshold value that is previously set by the technician as the exposure dose threshold value in the region other than the internal organs is applied.

In step 2232, the shape and the area of the opening region 51 of the diaphragm unit 44 are derived to be a shape and an area where the direct rays are irradiated onto at least the region of interest and an added value of the exposure doses with respect to the rectangular regions 1064 in a range in which the cumulative exposure doses R does not reach the corresponding exposure dose threshold value with respect to all of the rectangular regions 1064 included in the region of non-interest of irradiation field is maximized in regards to the region of non-interest.

In step 2234, information that indicates the shape and the area of the opening region 51 derived by the process of step 2232 and the change instruction information that instructs to change the opening state of the diaphragm unit 44 are transmitted to the radiation irradiating device 18. Then, the process proceeds to step 2236.

When the change instruction information is received, in the radiation irradiating device 18, the irradiating device control unit 140 controls the positions of the slit plates 44A to 44D to be the shape and the area indicated by the information received together with the change instruction information.

In step 2236, it is determined whether the timing at which capturing of the radiation image ends has come. If the determination result is NO, the process returns to step 2208. At a point in time when the determination result is YES, the process proceeds to step 2238. In the radiation image capturing processing program according to this exemplary embodiment, whether the current timing reaches timing at which capturing of the radiation image ends in step 2236 is determined by determining whether the technician inputs instruction information instructing to end capturing of the radiation image through the input unit such as the operation panel 112. However, the invention is not limited thereto and another form may be used. For example, it may be determined by determining whether a power supply switch (not shown in the drawings) of the electronic cassette 20 or the radiation irradiating device 18 is turned off.

In step 2238, the image capturing date and time and the frame rate that correspond to the information stored in the exposure dose history information by this medical treatment is stored in the exposure dose history information. In step 2240, instruction information that instructs to stop the exposure started by the process of step 2206 is transmitted to the radiation irradiating device 18 and the electronic cassette 20. In step 2242, after the image information stored by the process of step 2210 is transmitted to a radiology information system (RIS) server (not shown in the drawings) through an in-hospital network (not shown in the drawings), the radiation image capturing processing program ends. In the RIS server, a doctor may interpret or diagnose the radiation image that is captured using the image information received from the console 26.

FIG. 8 shows an example of a radiation image that is displayed on the display surface 28A of the display 28 by irradiating the radiation X onto an entire surface of an irradiation surface 36A of the radiation detector 36 according to this exemplary embodiment. FIG. 9 shows an example of a radiation image in a case in which the patient 14 lies in the same state as the state shown in FIG. 8, which is displayed on the display surface 28A of the display 28 by executing the radiation image capturing processing program according to this exemplary embodiment and irradiating radiation onto a partial region of the irradiation surface 36A of the radiation detector 36.

As shown in FIG. 9, in the imaging system 10 according to this exemplary embodiment, since the irradiation region of the direct rays of the radiation X may be restricted to the predetermined region (region including a region of interest in this exemplary embodiment), the exposure dose with respect to the patient 14 may be suppressed. In addition, the image according to the transmission dose of the position of the corresponding slit plate is displayed as an example in the state shown in FIG. 9 with respect to the region (gradation region in the display image of FIG. 9) of the peripheral part of the predetermined region. Therefore, a radiation image of the peripheral part may be observed.

As described in detail above, according to this exemplary embodiment, in a case in which the accumulative exposure dose (cumulative exposure dose R in this exemplary embodiment) from a point in time when the medical treatment using the radiation irradiated from the radiation source to the subject (patient 14 in this exemplary embodiment) to capture the movie of the radiation image reaches the predetermined exposure dose, the exposure dose with respect to the irradiation field of the radiation from the radiation source other than the a region of interest is controlled to be restricted. Therefore, the exposure dose with respect to the subject may be suppressed while the quality of the radiation image in the region of interest may be prevented from being deteriorated.

In this exemplary embodiment, since the cumulative exposure dose is calculated in a state where the cumulative exposure dose is weighted according to the predetermined conditions (progress period t in this exemplary embodiment), an actual cumulative exposure dose may be calculated. As a result, the exposure dose with respect to the patient may be accurately controlled.

In this exemplary embodiment, since the cumulative exposure dose is calculated for each of the divided regions each of which is the predetermined unit area in the irradiation field, the exposure dose with respect to the subject may be precisely restricted, as compared with the case where the cumulative exposure doses are collected and calculated over the entire region of the irradiation field.

In this exemplary embodiment, the imaging system includes the diaphragm unit (diaphragm unit 44 in this exemplary embodiment) that is provided between the radiation source and the subject and that has the opening region configured to transmit a part of the radiation emitted from the radiation source and an area the opening region can be changed, and the diaphragm unit is controlled to restrict the exposure dose by changing the area of the opening region of the diaphragm unit. Therefore, the region of the irradiation field other than the region of interest may be changed. As a result, convenience may be improved.

In particular, in this exemplary embodiment, the diaphragm unit is configured such that the transmission dose of the radiation decreases as the distance from the circumferential part of the opening region increases. Therefore, the radiation image in the irradiation field other than the region of interest may be observed.

In this exemplary embodiment, the control is performed following the region of interest that changes with time. Therefore, convenience may be improved.

In particular, in this exemplary embodiment, the position of the predetermined part of the medical apparatus (catheter 60 in this exemplary embodiment) that is inserted into the body of the subject is specified, and the specified position is controlled as the region of interest. Therefore, the region of interest does not need to be previously set and convenience may be improved.

In this exemplary embodiment, the exposure dose per unit time that is irradiated from the radiation source to the subject to capture the movie of the radiation image is calculated for each of the divided regions (rectangular region 1064 in this exemplary embodiment) each of which is the predetermined unit area, and the exposure dose information ("exposure dose" in the exposure dose history information in this exemplary embodiment) that indicates the calculated exposure dose is stored and associated with the divided region specification information ("exposure dose" in the exposure dose history information in this exemplary embodiment) to specify the corresponding divided region and the subject specification information ("ID" in the exposure dose history information in this exemplary embodiment) to specify the subject. Therefore, the cumulative exposure dose for each divided region may be derived using the stored exposure dose information, and the radiation may be effectively prevented from being excessively exposed to the subject.

In this exemplary embodiment, the time point information ("image capturing date and time" in the exposure dose history information in this exemplary embodiment) that indicates a point in time when the radiation is irradiated onto the subject, the medical treatment exposure dose information ("exposure dose" corresponding to the same "image capturing date and time" in the exposure dose history information in this exemplary embodiment) that indicates the exposure dose of the radiation per medical treatment, and the frame rate information ("frame rate" in the exposure dose history information in this exemplary embodiment) that indicates the frame rate of the capturing of the movie are acquired, and the acquired time point information, the medical treatment exposure dose information, and the frame rate information are stored and associated with the corresponding subject specification information. Therefore, the exposure dose that is indicated by the exposure dose information may be weighted on the basis of the time point information, the medical treatment exposure dose information, and the frame rate information, and the radiation may be effectively prevented from being excessively exposed to the subject.

In this exemplary embodiment, the exposure dose information indicates the exposure dose of the radiation that reaches the subject, in a state where the radiation is reduced by the diaphragm unit (diaphragm unit 44 in this exemplary embodiment) that is provided between the radiation source and the subject and that has the opening region configured to transmit a part of the radiation emitted from the radiation source and an area of the opening region can be changed. Therefore, even in the radiation image capturing system that uses the diaphragm unit, the cumulative exposure dose may be derived with high precision. As a result, the radiation may be effectively prevented from being excessively exposed to the subject.

The sensitivity of CsI which is used as the scintillator 304 changes as a temperature changes as shown in FIG. 26. For example, the sensitivity lowers about 0.3% if a temperature rises one degree. The sensitivity of GOS hardly changes as a temperature changes.

Circuits and elements such as the power supply unit 106, the gate line driver 88 and the signal processing unit 90 in the electronic cassette 20 generate heat by capturing images. Further, if a movie is captured by the IVR, a capturing time is long. Thus, in the electronic cassette 20 which uses CsI as the scintillator 304, there are cases in which the sensitivity of the scintillator 304 is lowered by heat from the circuits and elements when capturing a movie. The technician who performs IVR increases a radiation dose to be irradiated if the technician wishes to maintain an image quality necessary for diagnosis. However, if the radiation dose increases, an exposure dose to a patient will increase. In the present embodiment, the diaphragm unit is configured such that the transmission dose of the radiation decreases as the distance from the circumferential part of the opening region increases, and thus, an increase in exposure dose with respect to the patient can be suppressed.

The sensitivity of CsI lowers as the cumulative exposure dose increases when capturing images continuously, and when a condition in which radiation is not irradiated is maintained, the sensitivity which has lowered recovers, as shown in FIG. 27. In a case in which a movie is captured by IVR or the like, an imaging time is long. In a case in which static images are captured frequently when capturing a movie, an irradiation amount of radiation for capturing a static image is about 10-100 times that per one frame capturing a movie, and thus, the sensitivity of the scintillator 304 lowers as the cumulative exposure dose increases. In this case, if a technician wishes to maintain an image quality necessary for diagnosis, the technician increases the radiation dose to be irradiated. However, if the radiation dose increases, an exposure dose to a patient will increase. In the present embodiment, the diaphragm unit is configured such that the transmission dose of the radiation decreases as the distance from the circumferential part of the opening region increases, and thus, an increase in exposure dose with respect to the patient can be suppressed.

In the present embodiment, the diaphragm unit is configured such that the transmission dose of the radiation decreases as the distance from the circumferential part of the opening region increases, and thus, an increase in exposure dose with respect to the patient can be suppressed even if the radiation dose of the radiation X to be irradiated is increased accompanying a decreased in the sensitivity of the scintillator 304.

As mentioned above, the sensitivity of CsI lowers due to temperature change, the cumulative exposure dose and the like. Thus, the cumulative exposure dose may be obtained in consideration of lowering of the sensitivity of the scintillator 304.

Specifically, for example, a temperature change of the scintillator 304 may be estimated in advance from the radiation dose according to the capturing conditions, and then the cumulative exposure dose may be obtained in consideration of lowering of the sensitivity of the scintillator 304 due to the temperature change. As to the temperature change of the scintillator 304 during capturing of images, for example, a temperature sensor may be provided at the scintillator 304, and the temperature of the scintillator 304 during capturing of images may be monitored by the temperature sensor.

As to the cumulative exposure dose, the total exposure dose at a central portion in capturing up to the current time (the end of capturing of images) is measured as the region of interest is located at the central portion of the capturing region.

The lowering of the sensitivity of CsI due to the cumulative exposure dose depends on an operation temperature, and a stand by temperature of a panel. Thus, as to the change in the sensitivity of the scintillator 304, for example, in a case in which the imaging system 10 first irradiates a predetermined amount of radiation at the electronic cassette 20 each day of capturing and then performs calibration which corrects a condition of the device, a configuration may be provided in which the sensitivity of the scintillator 304 for each day of capturing is detected at the time of calibration of each capturing day, it is determined at which point on the curve shown in FIG. 27 the sensitivity is positioned, the temperature change of the scintillator 304 is estimated from the radiation amount according to the capturing conditions, and the cumulative exposure dose is obtained in consideration of the sensitivity of the scintillator 304 due to the temperature change.

Since the region of interest is an operation portion, it is necessary to maintain image quality of the region of interest. However, an influence is small even if a captured image of a region other than the region of interest is a little noisy. Therefore, in a case in which the exposure dose with respect to the irradiation field other than the region of interest is restricted if it is determined that the cumulative exposure dose R reaches the predetermined exposure dose, control may be performed to amplify the operational amplifier 92A of the sample hold circuit 92 which reads an image of the region to which the restriction is applied to an extent which is not usually used and reduce the maximum exposure dose.

Fifth Exemplary Embodiment

Figure 17:
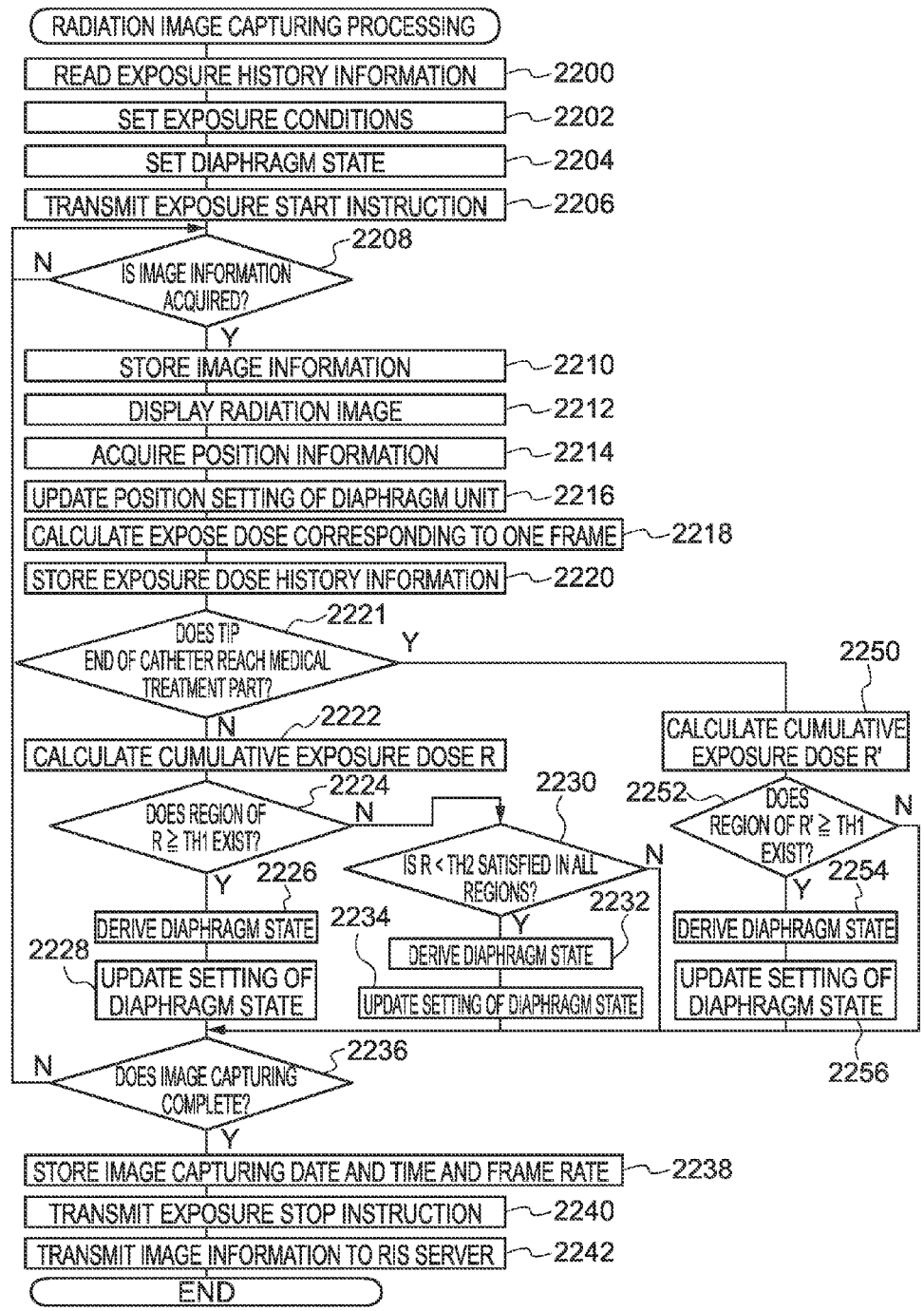
FIG. 17 is a flowchart illustrating a processing flow of a radiation image capturing processing program according to a fifth exemplary embodiment.

In the fifth exemplary embodiment, an example of the case where the cumulative exposure dose with respect to the irradiation field until capturing of the movie is completed is calculated and applied will be described. Since the configuration of the imaging system 10 according to the fifth exemplary embodiment is the same as that of the imaging system according to the first exemplary embodiment, the description will not be repeated. A function of the console 26 according to the fifth exemplary embodiment in a case in which the radiation image capturing processing is executed will be described with reference to FIG. 17. FIG. 17 is a flowchart illustrating a processing flow of the radiation image capturing processing program that is executed by the CPU 114 of the console 26 at this point in time. In FIG. 17, the steps that execute the same processes as those of FIG. 16 are denoted by the same step numbers as those of FIG. 16 and the description will not be repeated. Here, the case in which a lesion part which is to be a medical treatment object and a medical treatment time are previously set will be described.

In step 2221 of FIG. 17, it is determined whether the tip end of the catheter 60 reaches the lesion part which is the medical treatment object. If the determination result is NO, the process proceeds to step 2222. Meanwhile, if the determination result is YES, the process proceeds to step 2250.

In step 2250, on the basis of the cumulative exposure dose R at this point in time, a cumulative exposure dose R' in the irradiation field of the radiation X until the capturing of the movie is completed is calculated as follows.

First, by the same process as step 2222, the cumulative exposure dose R until this point in time is calculated, and a time (hereinafter, referred to as "remaining medical treatment time") from this point in time to a point in time when the medical treatment ends is calculated. On the assumption that the exposure conditions at this point in time are maintained, the cumulative exposure dose for each of the rectangular regions 1064 while the remaining medical treatment time passes is calculated, the cumulative exposure R is added for each of the rectangular regions 1064, and the cumulative exposure dose R' is calculated.

In step 2252, it is determined whether the cumulative exposure dose R' reaching the exposure dose threshold value of the internal organ positioned at the corresponding position exists in the cumulative exposure doses R' for the rectangular regions 1064 that are included in the region (region of non-interest of irradiation field) other than the region of interest of the full irradiation field calculated by the process of step 2250 described above. If the determination result is NO, the process proceeds to step 2236. Meanwhile, if the determination result is YES, the process proceeds to step 2254.

At this time, in step 2252, the names of the internal organs that are included in the coordinate range corresponding to the region of non-interest of irradiation field are specified on the basis of the internal organ coordinate information and the internal organ name information stored in the preparation step of the IVR, and the exposure dose threshold value (see also FIG. 10) that corresponds to the specified internal organ is read from the HDD 120.

In step 2252, it is determined whether the cumulative exposure dose R' reaching the exposure dose threshold value of the internal organ positioned at the corresponding position exists in the cumulative exposure doses R' of the rectangular regions 1064 included in the region of non-interest of irradiation field. At this time, in a case in which the internal organ positioned at the corresponding position does not exist, a threshold value that is previously set by the technician as the exposure dose threshold value in the region other than the internal organs is applied, similar to the process of step 2224.

In step 2254, the shape and the area of the opening region 51 of the diaphragm unit 44 are derived to be a shape and an area where the direct rays are irradiated onto at least the region of interest and an added value of the exposure doses with respect to the rectangular regions 1064 whose cumulative exposure doses R' reach the corresponding exposure dose threshold value, among the rectangular regions 1064 included in the region of non-interest of irradiation field, is minimized in regards to the region of non-interest.

In step 2256, information that indicates the shape and the area of the opening region 51 derived by the process of step 2254 and the change instruction information that instructs to change the opening state of the diaphragm unit 44 are transmitted to the radiation irradiating device 18. Then, the process proceeds to step 2236.

When the change instruction information is received, in the radiation irradiating device 18, the irradiating device control unit 140 controls the positions of the slit plates 44A to 44D to be the shape and the area indicated by the information received together with the change instruction information.

As described in detail above, in this exemplary embodiment, in addition to the effect according to the fourth exemplary embodiment, the cumulative exposure dose with respect to the irradiation field until a point in time when the capturing of the movie is completed is calculated as the cumulative exposure dose. Therefore, the cumulative exposure dose that is accumulated by a point in time when the capturing of the movie in the irradiation field excluding the region of interest is completed may be restricted to the predetermined exposure dose or less.

In this exemplary embodiment, in addition to the effect according to the fourth exemplary embodiment, the cumulative exposure dose with respect to the irradiation field until a point in time when the capturing of the movie is completed is calculated as the cumulative exposure dose. Therefore, the cumulative exposure dose that is accumulated by a point in time when the capturing of the movie in the irradiation field excluding the region of interest is completed may be restricted to the predetermined exposure dose or less. As a result, the radiation may be effectively prevented from being excessively exposed to the subject.

The invention is described using the exemplary embodiments. However, the technical scope of the invention is not limited to the scope described in the exemplary embodiments.

Various changes and improvements may be made without departing from the spirit of the invention, and the changed and improved exemplary embodiments are also included in the technical scope of the invention.

The exemplary embodiments described above do not restrict the invention that is described in claims, and all combinations of the characteristics that are described in the exemplary embodiments are not essential in implementing the invention. The configuration where some components are removed may be extracted as the invention, as long as the same effect is obtained even though some components are removed from all of the components described in the exemplary embodiments.

For example, in the exemplary embodiments, the example of the case where the position of the tip end of the catheter 60 in the body of the patient 14 is specified using the entry amount of the catheter 60 in the body of the patient 14 is described. However, the invention is not limited thereto. For example, the position may be specified using a technology for recognizing an image, the position may be specified using an IC tag or the position may be specified using a magnetic body.

Examples of the case where the position is specified using the technology for recognizing the image may include a case in which pattern matching is performed between an image indicated by image information obtained from the electronic cassette at the time of the specification and an image indicated by image information obtained by previously capturing an image with respect to the tip end of the catheter 60 based on the electronic cassette 20 and the position of the tip end of the catheter 60 in the image indicated by the image information obtained at the time of the specification is specified.

Examples of the case in which the position is specified using the IC tag may include a case where an IC tag to send a predetermined signal is attached to the tip end of the catheter 60, plural antennas are provided in an operating room, the position of the IC tag of a signal sending source is specified by a triangulation technology on the basis of the strength of the signal received by the antennas, and the position of the tip end of the catheter 60 is specified.

Examples of a case in which the position is specified using a magnetic body may include a case in which a magnet is attached to the tip end of the catheter 60, a measurer which measures the magnetic force of the magnet attached to the tip end of the catheter 60 is provided at the position (for example, position of the case 40) which is not overlapping the radiation detector 36 of the irradiation surface 32 of the electronic cassette 20, the distance from the measurer to the magnet attached to the tip end of the catheter 60 is estimated from the magnitude of the magnetic force measured by the measurer, and the position of the tip end of the catheter 60 in the touch panel of the UI panel 11 is estimated on the basis of the coordinate information of the entry scheduled path.

As a modification, the position of the tip end of the electronic cassette 60 may be estimated by measuring the magnitude of the magnetic force of the magnet that is attached to the tip end of the catheter 60 and acquiring a direction of a generation source force of the magnetic force. In this case, the coordinate information of the entry scheduled path is not needed. Instead of the magnet, a supersonic wave transmitter or a gamma-ray transmitter may be used. In this case, the distance from the measurer to the transmitter is estimated by estimating the physical amount from the transmitter, and the position of the tip end of the catheter 60 is estimated using the distance. As such, any method may be used as the method that estimates the position of the tip end of the catheter 60 inserted into the body of the patient 14 in the body of the patient 14.

In the exemplary embodiments, the example of the case in which the position of the tip end of the catheter 60 inserted into the body of the patient 14 in the body of the patient 14 is estimated is described. By the same method, the positions of the parts other than the tip end of the catheter 60 inserted into the body of the patient 14 in the body of the patient 14 may be estimated.

In the exemplary embodiments, the case in which the diaphragm unit 44 is configured to change all of the area, the shape, and the position of the opening region 51 is described. However, the invention is not limited thereto. For example, the diaphragm unit 44 may be configured to change one or two of the area, the shape, and the position of the opening region 51. Even in this case, substantially the same effect as the exemplary embodiments may be achieved.

In the exemplary embodiments, the case in which the movable direction of each slit plate in the diaphragm unit 44 is a direction orthogonal to the transmission direction of the radiation X is described. However, the invention is not limited thereto. For example, each slit plate may be configured to move in a direction crossing the transmission direction of the radiation X, instead of the direction orthogonal to the transmission direction. Even in this case, the similar effect as the exemplary embodiments may be achieved.

In the exemplary embodiments, the slit plates which have rectangular shapes in plan view, which are composed of the flat members and each of whose thickness in the height direction gradually increases linearly in sectional view from the tip end to the rear end, are applied as the slit plates provided in the diaphragm unit 44. However, the invention is not limited thereto. For example, the slit plates that have the different shapes shown in FIGS. 18 to 20 may be applied.

Figure 18:
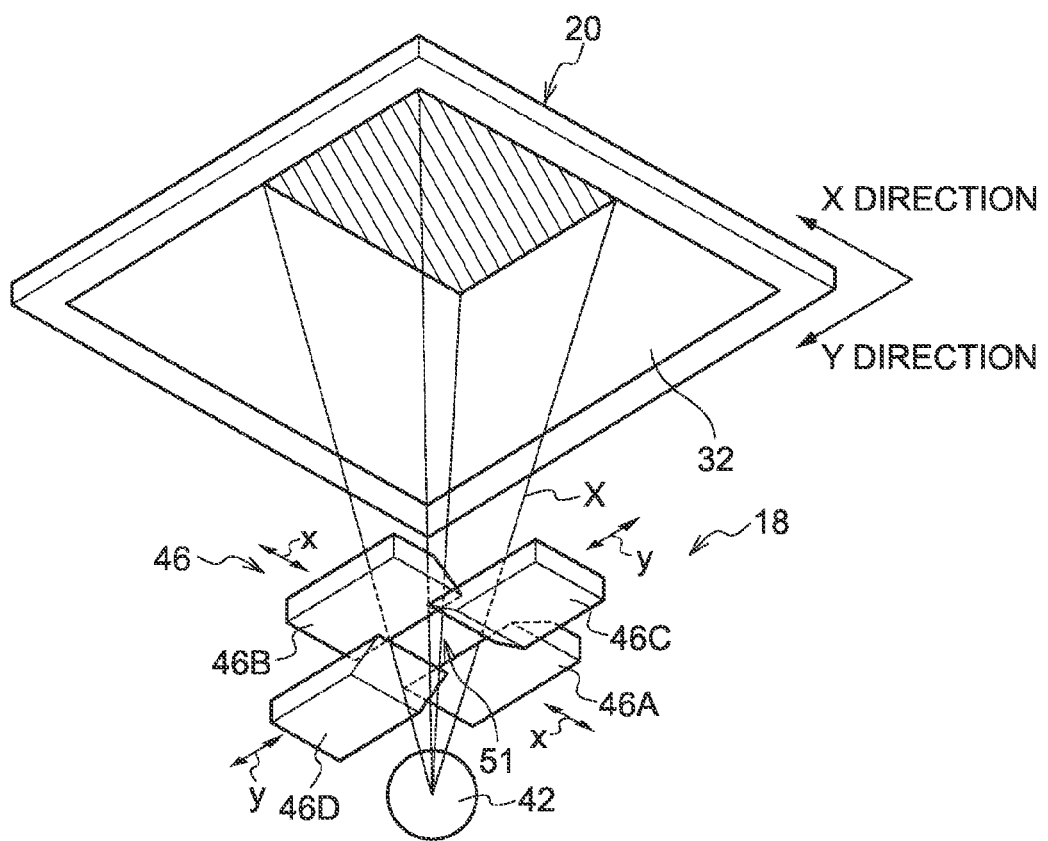
FIG. 18 is a perspective view illustrating the configuration of a main part of a radiation irradiating device according to another exemplary embodiment.

In the example shown in FIG. 18, the slit plates 46A to 46D which are provided in the diaphragm unit 46 are composed of the flat members which have rectangular shapes in plan view and each of whose thickness in the height direction gradually increases linearly in sectional view from the tip end to the intermediate part, and the slit plates 46A to 46D are disposed such that the tip ends of the slit plates 46A and 46B face each other, the tip ends of the slit plates 46C and 46D face each other, and the opening region 51 with the rectangular shape in plan view is formed by the tip ends of the slit plates 46A to 46D.

Figure 19:
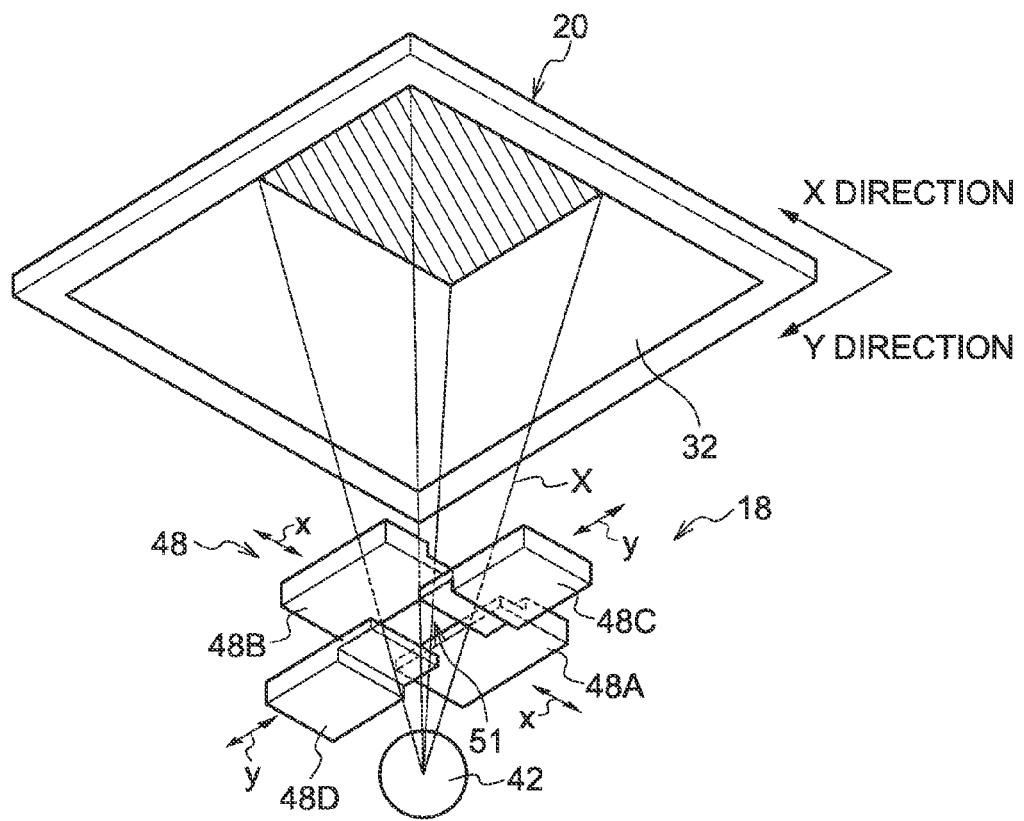
FIG. 19 is a perspective view illustrating the configuration of a main part of a radiation irradiating device according to another exemplary embodiment.

Meanwhile, in the example shown in FIG. 19, the slit plates 48A to 48D which are provided in the diaphragm unit 48 are composed of the flat members which have rectangular shapes in plan view and each of whose thickness increases stepwise (non-linearly) in section view as the distance from the circumferential part of the opening region 51 increases, and the slit plates 48A to 48D are disposed such that the tip ends of the slit plates 48A and 48B face each other, the tip ends of the slit plates 48C and 48D face each other, and the opening region 51 with the rectangular shape in plan view is formed by the tip ends of the slit plates 48A to 48D.

Figure 20:
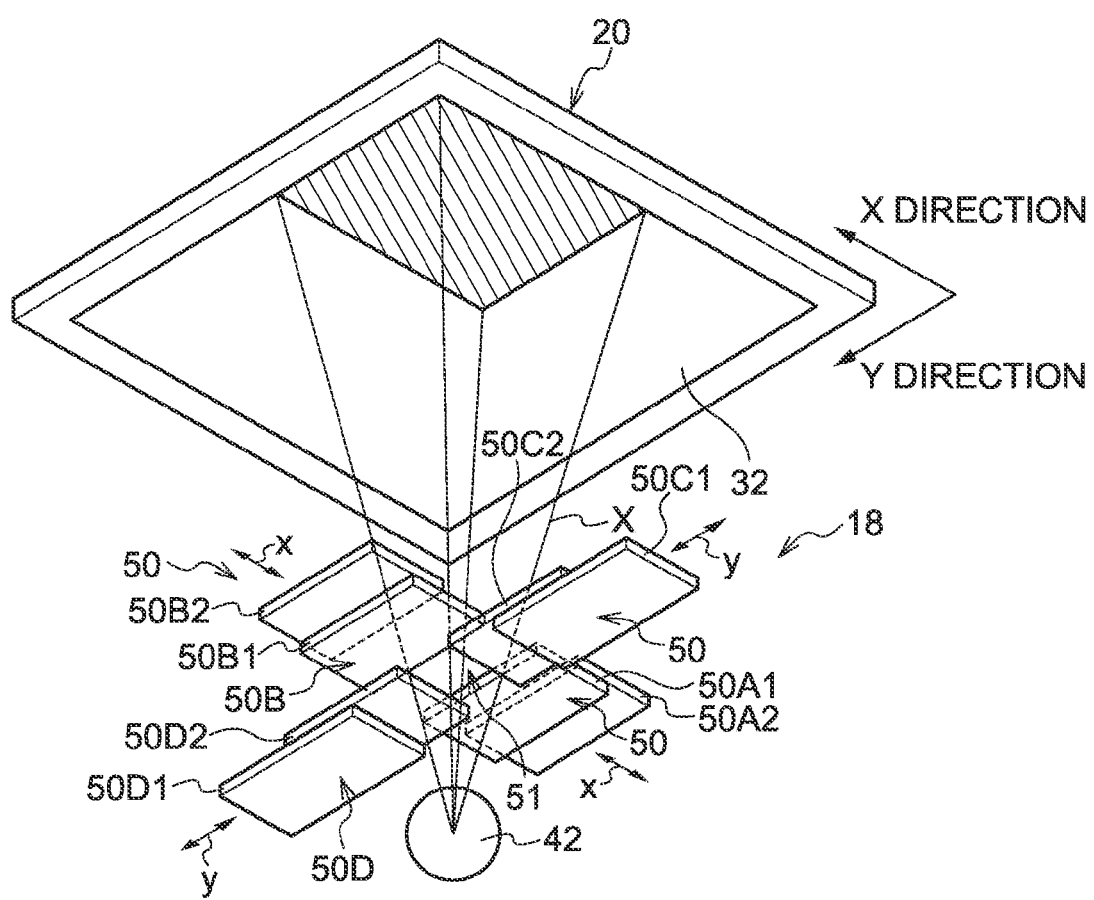
FIG. 20 is a perspective view illustrating the configuration of a main part of a radiation irradiating device according to another exemplary embodiment.

In the example shown in FIG. 20, the slit plates that constitute the slit plate group 50A (slit plates 50A1 and 50A2), the slit plate group 50B (slit plates 50B1 and 50B2), the slit plate group 50C (slit plates 50C1 and 50C2), and the slit plate group 50D (slit plates 50D1 and 50D2) provided in the diaphragm unit 50 are composed of the plate members, and the slit plate groups 50A to 50D are disposed such that the end faces of the slit plates of the slit plate group 50A and the slit plate group 50B face each other, the end faces of the slit plates of the slit plate group 50C and the slit plate group 50D face each other, and the opening region 51 with the rectangular shape in plan view is formed by the end faces of the slit plate groups 50A to 50D.

The diaphragm units shown in FIGS. 18 to 20 are the same as the diaphragm unit 44 according to the exemplary embodiments in that the slit plates are formed of a material shielding the radiation X such as lead or tungsten, one slit plate group having the facing ends is configured to be movable in the x direction and the other slit plate groups are configured to be movable in the y direction corresponding to the direction orthogonal to the x direction, the movable range of the slit plates is a range from a state where ends of the slit plates disposed to face each other contact each other, that is, a state where the opening region 51 is fully closed to a state where the opening region 51 has a rectangular shape in plan view and has a maximum area (full open state), and the slit plates are movable by the motors.

In the case of the diaphragm unit 46 shown in FIG. 18, substantially the same effect as the diaphragm unit 44 according to the exemplary embodiments may be achieved. Meanwhile, in the case of the diaphragm unit 48 shown in FIG. 19, the diaphragm unit may be easily configured as compared with the case in which the diaphragm unit is configured such that the thickness increases linearly in sectional view. In the case of the diaphragm unit 50 shown in FIG. 18, a degree of freedom of the shape or the area of the opening region 51 may be improved.

In each of the diaphragm units shown in FIGS. 3 and 18 to 20, all of the slit plates 50 do not need to be configured to be movable, and at least one slit plate may be configured to be movable. In this case, it is needless to say that the number of motors to move the slit plates may be reduced.

Figure 21:
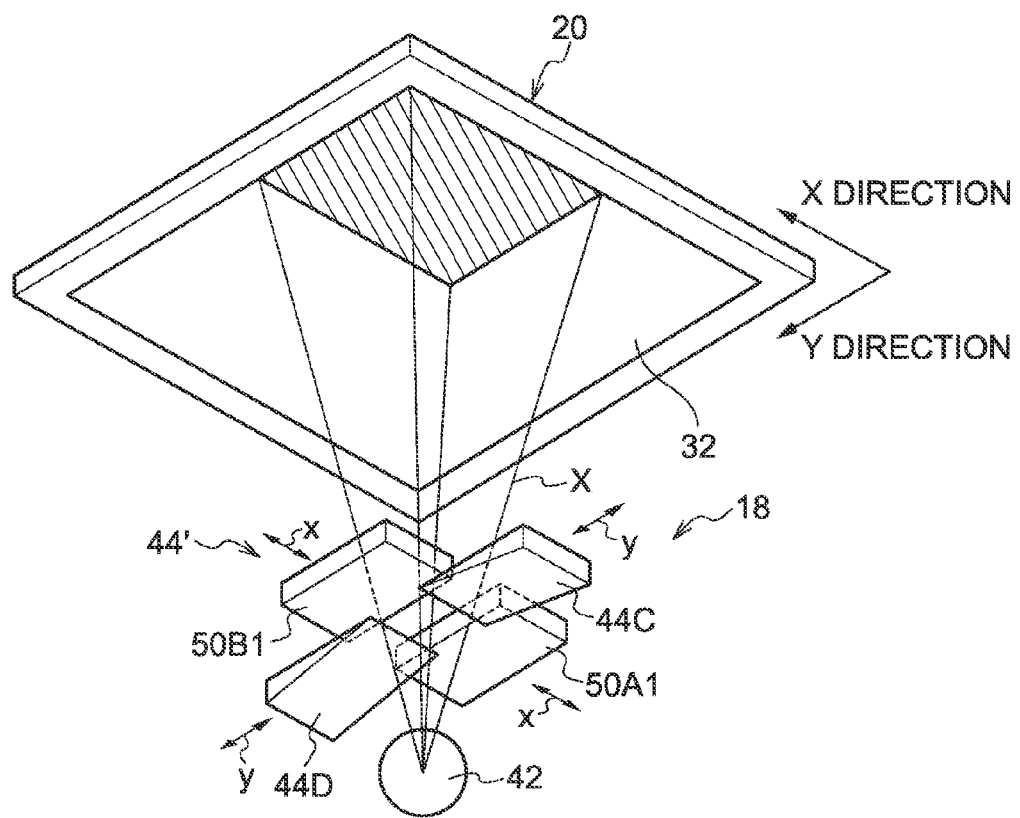
FIG. 21 is a perspective view illustrating the configuration of a main part of a radiation irradiating device according to another exemplary embodiment.

In each of the diaphragm units shown in FIGS. 3 and 18 to 20, the shapes of all of the slit plates that constitute the diaphragm unit are the same. However, the invention is not limited thereto and the slit plates that are used in the diaphragm unit may be combined and applied. FIG. 21 shows an example of the case in which wedge-type slit plates (slit plates 44C and 44D) used in a diaphragm unit 44 and flat slit plates (slit plates 50A1 and 50A2) used in the diaphragm unit 50 are applied. Even in this case, substantially the same effects as the above exemplary embodiments may be achieved.

Figure 22:
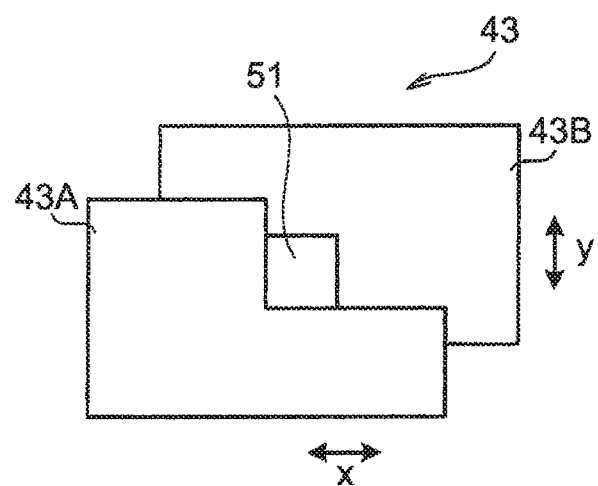
FIG. 22 is a perspective view illustrating the configuration of a main part of a diaphragm unit according to another exemplary embodiment.

In each of the diaphragm units shown in FIGS. 3 and 18 to 20, two pairs of slit plates or a slit plate group where ends face each other are applied. However, the invention is not limited thereto. For example, as shown in FIG. 22, a slit plate 43A and a slit plate 43B of a pair that has an L shape in plan view may be combined and applied. In this case, shapes of the slit plates 43A and 43B in a thickness direction (height direction) are wedge shapes and staircase shapes, as shown in FIGS. 3, 18, and 19.

In this case, the diaphragm is the same as the other diaphragm in that at least one of the slit plate 43A and the slit plate 43B is configured to be movable in at least one of the x direction and the y direction, a movable range of each slit plate is a range from a state where the opening region 51 is fully closed to a state (full open state) where the opening region 51 holds a rectangular shape in plan view and has a maximum area, and the movable slit plates are moved by the motors.

In this case, as compared with the other diaphragm units, the number of slit plates may be reduced and a manufacturing cost may be reduced.

In each of the diaphragm units shown in FIGS. 3 and 18 to 22, the individual slit plates are formed of a single material. However, the invention is not limited thereto. That is, the individual slit plates may be formed of a combination of different materials, and the transmission dose of the radiation X may be decreased as the distance from the circumferential part of the opening region 51 increases.

As an example of the above case, the diaphragm unit may be formed of a composition of elements, such as lead, tungsten, and molybdenum, having a radiation shielding ability, and elements not having the radiation shielding ability, and a combination ratio may be changed according to the distance from the circumferential part of the opening region 51. In this case, a single substance or a compound of the elements that have the radiation shielding ability may be kneaded into a resin material that does not have the radiation shielding ability. This is preferable because formability becomes high and the weight may be reduced.

In the diaphragm unit described above, the ends of each slit plate that face each other may have a linear shape in plan view. However, the invention is not limited thereto and the shape may be a curved shape.

In the exemplary embodiments, the case in which the area of the opening region 51 of the diaphragm unit 44 is constant without depending on the image capturing position is described. However, the invention is not limited thereto. For example, the diaphragm unit 44 may be controlled such that the area of the opening region 51 is increased in a case in which the area of the opening region 51 increases as the distance from the lesion part which is the medical treatment object decreases and at least one of the peripheral part of the insertion opening of the catheter 60 and the lesion part which is the medical treatment object is image captured as compared with the other cases, that is, the area of the opening region 51 is changed according to the position of the predetermined part of the specified medical apparatus. In this case, convenience may be improved.

In the exemplary embodiments, a case in which the irradiation region of the direct rays of the radiation X is restricted to the region of interest by the diaphragm 44 is described, but the present invention is not limited to this. For example, a gonad of a female, an embryo or the like is likely to be affected by a radiation and weak with respect to exposure. A medical device such as a pacemaker which is used integrally with a human body uses a semiconductor, and since a specific function thereof degrades by irradiation of a radiation, it is preferable to suppress exposure. Therefore, information of a region, to which exposure is to be suppressed which is a region which is likely to be affected by radiation such as a gonad of a female or an embryo or which is a region in which a medical device which is used integrally with a human body is implanted, is obtained, and the irradiating device control unit 140 may control the diaphragm 44 such that radiation transmitting through the diaphragm 44 irradiates the region at which exposure is to be suppressed. The information relating to the region to which the exposure is to be suppressed may be input through the operation panel 112, may be transferred from an external device via a network, or may be specified by various image processing such as a pattern matching from a captured radiation image.

In the exemplary embodiments, a case in which the irradiation region of the direct rays of the radiation X is restricted to the region of interest by the diaphragm 44 in a case in which the IVR is performed is described, but the present invention is not limited to this. An advance capturing may be performed for positioning before a main capturing such as the IVR is performed. In the advance capturing, the irradiation region of the direct rays of the radiation X may be restricted by the diaphragm 44. For example, an exposure dose for each region such as a breast, an abdomen, an arm and the like for each day for each patient may be stored in a database of an external server such as an RIS server. The total value of exposure dose in a predetermined period (for example, the last three months) for each region of a patient who is a capturing subject may be obtained from the information stored in the database. In the advance capturing for positioning, if a region at which an exposure dose is large and the exposure dose exceeds a predetermined allowable threshold exists near the region which is the capturing subject at this time, the diaphragm 44 may be controlled such that the direct rays of the radiation X are not irradiated and the radiation X transmitting through the slit plates 48A to 48D is irradiated with respect to the region which exceeds the threshold. Thus, the exposure at the portion at which the exposure dose has been already large in the advance capturing can be further suppressed. Note that similar control may be performed in the main capturing such as IVR.

For example, in the exemplary embodiments, the case in which the cumulative exposure dose for each of the rectangular regions 1064 and the predetermined exposure dose threshold value are compared with each other is described. However, the invention is not limited thereto. For example, the cumulative exposure dose for each region having a wider range than the internal organs such as the chest, the abdomen, the arm, and the leg and the exposure dose threshold value that is previously set according to each region may be compared with each other.

In the exemplary embodiments, the case in which the cumulative exposure dose of the irradiation field of the radiation other than the region of interest is compared with the exposure dose threshold value is described. However, the invention is not limited thereto. For example, the cumulative exposure dose and the exposure dose threshold value may be compared with each other, in a state where the region of interest is included.

In the exemplary embodiments, the case in which the diaphragm unit 44 is controlled to be reduced when the cumulative exposure dose reaches the exposure dose threshold value is described. However, the invention is not limited thereto. In this case, in addition to the control, the dose of the radiation X that is emitted from the radiation source 42 may be reduced.

In the exemplary embodiments, the case in which the conditions of the shape and the area of the opening region 51 are the shape and the area in which the direct rays are irradiated with respect to at least the region of interest and the added value of the exposure doses with respect to the rectangular regions 1064 whose cumulative exposure doses reach the exposure dose threshold value, among the rectangular regions 1064 included in the region of non-interest of irradiation field, is minimized with respect to the region of non-interest of irradiation field are applied as the conditions to reduce the diaphragm unit 44 is described. However, the invention is not limited thereto. For example, another condition of the direct rays being irradiated onto at least the region of interest, such as the condition in which the shape and the area are the shape and the area in which the direct rays are irradiated onto only the region of interest, may be applied.

In the exemplary embodiments, the case in which the position of each internal organ of the patient 14 who is the medical treatment object is specified by previously inputting the internal organ coordinate information is described. However, the invention is not limited thereto. For example, pattern matching may be performed between an image indicated by image information obtained by capturing an image with respect to the patient 14 which is to be the medical treatment object based on the electronic cassette 20 and an image indicated by the image information obtained by previously capturing an image with respect to the body of the patient using the electronic cassette 20, and the position of each internal organ of the patient 14 who is to be the medical treatment object may be specified.

In the exemplary embodiments, the case in which the progress period t is applied as the parameter to determine the weight value is described. However, the invention is not limited thereto. For example, in addition to the progress period t, at least one of the exposure dose per unit time, the exposure dose per medical treatment, and the frame rate at the time of capturing an image may be applied.

In a case in which the exposure dose per unit time is applied, the weight value is set to increase as the exposure dose per unit time increases. In a case in which the exposure dose per medical treatment is applied, the weight value is set to increase as the exposure dose per medical treatment increases. In a case in which the frame rate at the time of capturing an image is applied, the weight value is set to increase as the frame rate increases. At this time, even though any parameter is applied, the weight value is set such that a maximum value is "1" and the exposure dose obtained by multiplying the weight value is not more than the exposure dose before the multiplication.

In a case in which at least one of the exposure dose per unit time, the exposure dose per medical treatment, and the frame rate at the time of capturing an image is applied as the parameter to determine the weight value, the weight value may be determined at a point in time when a value of the applied parameter is determined. Therefore, the determined weight value may be stored in the exposure dose history information. In this case, the weight value management information is not needed.

In the exemplary embodiments, the case in which the exposure region, the exposure dose, and the exposure period are stored for each frame of the radiation image is described. However, the invention is not limited thereto. The above information may be stored for plural frames and may be stored for each medical treatment.

In the exemplary embodiments, the case in which adjusting with the position of the corresponding rectangular region 64 in past capturing of the image with respect to the patient 14 is performed by allowing the patient 14 to lie on the object table 16A to cause the predetermined reference part (top part of the head in the exemplary embodiments) to be positioned at the predetermined reference position in the object table 16A for each patient is described. However, the invention is not limited thereto. For example, as disclosed in Japanese Patent Application Laid-Open (JP-A) No. 2008-206962, the position may be automatically adjusted on the basis of the anatomical characteristic in the radiation image obtained by capturing the image. In this case, since the above configuration may correspond to the temporal change in the figure of the patient 14, the position may be adjusted with high precision, as compared with the exemplary embodiments.

Further, a marker that is formed of a material enabling the capturing of an image as a radiation image and that has a shape identified by the technology for recognizing an image to be conventionally known may be attached to the predetermined reference position as the position enabling the capturing of the radiation image in the patient 14 before medical treatment, the position of the marker may be specified by the technology for recognizing an image at the time of capturing the radiation image, the coordinate information indicating the specified position may be stored in the exposure dose history information for each frame, plural frames, and each medical treatment of the radiation image, the coordinate information may be used as information indicating the same reference position, and the position may be adjusted. In this case, instead of the marker, another member that may be applied as the reference position of the reflective photo sensor 62 may be applied.

In the exemplary embodiments, a case in which the present invention is applied to the medical treatment in which the catheter 60 is inserted into the body of the patient 14 from a neck portion is described, but the present invention is not limited to this. For example, the present invention may be applied to a medical treatment in which the catheter 60 is inserted into the body of the patient 14 from an inguinal of a thigh, an armpit and the like.

Although it is not mentioned in the exemplary embodiments, since the exposure dose history information is stored continuously in time series during the medical treatment in the exemplary embodiments, a portion to which an exposure dose is instantly larger than other portions in the past can be obtained, whereby it may be deemed that an impact of the exposure at the portion is larger than at the other portions, and the diaphragm 44 may be controlled such that the irradiation amount of radiation with respect to the portion is suppressed compared with the other portions. For example, the total value of exposure dose in a predetermined period (for example, last three months) for each region of a patient who is a capturing subject may be obtained from the exposure dose history information. If a region at which an exposure dose is large and the exposure dose exceeds a predetermined allowable threshold exists near the region which is the capturing subject at this time, the diaphragm 44 may be controlled such that the radiation X transmitting through the slit plates 48A to 48D is irradiated with respect to the region which exceeds the threshold. Thus, the exposure at the portion to which the exposure dose has been already large in the advance capturing can be further suppressed. The control may also be performed in the main capturing such as the IVR. Further, the control may be performed in the advance capturing such as IVR for positioning before the main capturing is performed.

In the exemplary embodiments, a case in which the time point information, the medical treatment exposure dose information, and the frame rate information are all stored, but the present invention is not limited to this. One or two of the above information may be stored.

In the exemplary embodiments, the example of the case in which the CPU 114 of the console 26 executes the radiation image capturing processing and the position specification processing is described. However, the invention is not limited thereto. For example, the irradiating device control unit 140 of the radiation irradiating device 18 or the cassette control unit 100 of the electronic cassette 20 may execute the radiation image capturing processing and the position specification processing.

The configuration (see FIGS. 1 to 6) of the imaging system 10 that is described in the exemplary embodiments is exemplary, and various changes may be made in a range that does not depart from the spirit and scope of the prevent invention.

The processing flows of the radiation image capturing processing program (see FIG. 7) and the position specification processing program that are described in the exemplary embodiments are exemplary, and the unnecessary steps may be removed, new steps may be added or the processing sequence may be changed in a scope that does not depart from the spirit and scope of the prevent invention.

The data configuration (see FIGS. 7 to 9) of the various information that is described in the exemplary embodiments is also exemplary, and the unnecessary data may be erased or new data may be added in a scope that does not depart from the spirit and scope of the prevent invention.

In the exemplary embodiments, the catheter 60 in the IVR is described as the example of the operative procedure and the medical apparatus inserted into the body of the patient 14. However, another operative procedure and another medical apparatus (guide wire in the IVR and screw, plate, or intramedullary nail in fracture treatment) may be applied.

According to a first aspect of the invention, a radiation image capturing device includes a radiation image capturing unit that captures a radiation image based on radiation which is emitted from a radiation source and which is transmitted through a subject, a diaphragm unit that is provided between the radiation source and the subject, wherein the diaphragm unit has an opening region which is configured to transmit a part of the radiation emitted from the radiation source and whose area is changeable, and the diaphragm unit is configured such that a transmission dose of the radiation decreases as a distance from a circumferential part of the opening region increases, and a control unit that controls the diaphragm unit such that direct rays of the radiation are irradiated onto a predetermined region of the subject.

In the first aspect of the invention, the exposure dose with respect to the subject may be suppressed by configuring the area of the opening region of the diaphragm unit to reduce the radiation irradiated onto the subject is changeable and controlling the diaphragm unit such that the direct rays of the radiation are irradiated onto the predetermined region of the subject. In addition, the diaphragm unit is configured such that the transmission dose of the radiation decreases as the distance from the circumferential part of the opening region increases, and thereby the radiation is transmitted through the peripheral part of the opening region and the image is captured. As a result, the radiation image of the peripheral part of the imaging object region may be observed.

As such, according to the radiation image capturing device of the first aspect, the area of the opening region of the diaphragm unit to reduce the radiation irradiated onto the subject is changeable and the diaphragm unit is controlled such that the direct rays of the radiation are irradiated onto the predetermined region of the subject. In addition, the diaphragm unit is configured such that the transmission dose of the radiation decreases as the distance from the circumferential part of the opening region increases. Therefore, the radiation image of the peripheral part of the imaging object region may be observed while the exposure dose with respect the subject is suppressed.

According to a second aspect, in the first aspect, the diaphragm unit may be configured such that at least one of a shape and a position of the opening region are changeable. Thereby, in a case in which the diaphragm unit is configured such that the shape of the opening region is changeable, the irradiation shape of the radiation may be changed. In a case in which the diaphragm unit is configured such that the position of the opening region is changeable, the irradiation position of the radiation may be changed.

According to a third aspect, in the first aspect, the diaphragm unit may be configured such that the thickness in a radiation transmission direction increases as the distance from the circumferential part of the opening region increases, whereby the transmission dose of the radiation decreases as the distance from the circumferential part of the opening region increases. Thereby, the diaphragm unit may be easily configured, as compared with the case where the transmission dose of the radiation in the diaphragm unit is reduced by the quality of the material constituting the diaphragm unit.

According to a fourth aspect, in the third aspect, the diaphragm unit may be configured such that the thickness increases linearly in sectional view as the distance from the circumferential part of the opening region increases. Thereby, a discomfort sense of the radiation image of the peripheral part of the imaging object region may be reduced as compared with the case of the configuration where the thickness increases stepwise in sectional view.

According to a fifth aspect, in the third aspect, the diaphragm unit may be configured such that the thickness increases stepwise in sectional view as the distance from the circumferential part of the opening region increases. Thereby, the diaphragm unit may be easily configured, as compared with the case of the configuration where the thickness increases linearly in sectional view.

According to a sixth aspect, in the first aspect, the diaphragm unit may be formed of a combination of different materials, whereby the diaphragm unit may be configured such that the transmission dose of the radiation decreases as the distance from the circumferential part of the opening region increases. Thereby, the shape of the diaphragm unit may be configured as a simple shape such as a rectangular parallelepiped or a cube.

According to a seventh aspect, in the first aspect, the diaphragm unit may be configured including plural flat members such that the plural flat members overlap in a radiation transmission direction and at least one flat member moves in a direction crossing the radiation transmission direction. Thereby, a degree of freedom of the shape or the area of the opening region in the diaphragm unit may be improved.

According to an eighth aspect, in the first aspect, the control unit may control the diaphragm unit such that the direct rays of the radiation are irradiated following a region of interest which changes with time. Thereby, convenience may be improved.

According to a ninth aspect, in the eighth aspect, the radiation image capturing device may further include a specifying unit that specifies a position of a predetermined part of a medical apparatus inserted into a body of the subject. The control unit may control the diaphragm unit such that the direct rays of the radiation are irradiated onto the position specified by the specifying unit. Thereby, the region where the direct rays of the radiation are irradiated does not need to be previously set, and convenience may be improved.

According to a tenth aspect, in the ninth aspect, the specifying unit may specify the position of the predetermined part using at least one of image recognition based on image information obtained by the radiation image capturing unit, an IC tag provided in the predetermined part, or a magnetic body provided in the predetermined part. Thereby, in a case in which the specifying unit specifies the position using the image recognition, since a member to specify the position does not need to be provided, the invention may be realized at a low cost. In a case in which the specifying unit specifies the position using at least one of the IC tag and the magnetic body, the position may be accurately specified, as compared with the case in which the specifying unit specifies the position using the image recognition.

The IC tag may be called an RFID tag, an ID tag or a wireless tag. However, the tag may be called the IC tag in this specification.

According to an eleventh aspect, in the ninth aspect, the control unit may control the diaphragm unit such that the area of the opening region is changed according to the position specified by the specifying unit. Thereby, convenience may be improved.

In the first aspect, a radiation detector of an indirect conversion type, which is configured such that a phosphor layer which emits light due to irradiation with radiation and a substrate at which a photoelectric conversion element which converts the light generated at the phosphor layer into a charge is formed are laminated, may be provided in the radiation image capturing unit.

It is preferable that the phosphor is CsI.

The radiation detector may be provided in the radiation image capturing unit such that a radiation ray is incident from a substrate side.

In the first aspect, the ninth or tenth aspect, the irradiation image capturing device may further include an obtaining unit which obtains information relating to a region at which exposure is to be suppressed, and the control unit controls the diaphragm unit such that the radiation transmitting through the diaphragm unit is irradiated at the region at which the exposure is to be suppressed.

According to a twelfth aspect, a radiation image capturing system includes the radiation image capturing device of any one of the first to eleventh aspects and a radiation source that emits the radiation irradiated onto the subject designated as a capturing object of a radiation image by the radiation image capturing device.

As such, according to the twelfth aspect, since the radiation image capturing system includes the radiation image capturing device of any one of the first to eleventh aspects, similar to the radiation image capturing device, the radiation image of the peripheral part of the imaging object region may be observed while the exposure dose with respect to the subject may be suppressed.

According to the radiation image capturing device and the radiation image capturing system of the invention, the area of the opening region of the diaphragm unit which reduces the radiation irradiated onto the subject is changeable and the diaphragm unit is controlled such that the direct rays of the radiation are irradiated onto the predetermined region of the subject. In addition, the diaphragm unit is configured such that the transmission dose of the radiation decreases as the distance from the circumferential part of the opening region increases. Therefore, the radiation image of the peripheral part of the imaging object region may be observed while the expose dose with respect the subject may be suppressed.

According to a thirteenth aspect, a radiation control device includes a calculating unit that calculates a cumulative exposure dose from a point in time when medical treatment starts using radiation irradiated from a radiation source to a subject to capture a movie of a radiation image, a restricting unit that restricts an exposure dose with respect to an irradiation field of the radiation irradiated from the radiation source excluding a region of interest, a determining unit that determines whether the cumulative exposure dose calculated by the calculating unit reaches a predetermined exposure dose, and a control unit that controls the restricting unit to restrict the exposure dose, in a case in which the determining unit determines that the cumulative exposure dose reaches the predetermined exposure dose.

As such, according to the radiation control device of the thirteenth aspect, in a case in which the cumulative exposure dose from a point in time when the medical treatment starts using the radiation irradiated from the radiation source to the subject to capture the movie of the radiation image reaches the predetermined exposure dose, the restricting unit is controlled to restrict the exposure dose with respect to the irradiation field of the radiation based on the radiation source other than the region of interest. Therefore, the exposure dose with respect to the subject may be suppressed while the quality of the radiation image in the region of interest may be prevented from being degraded.

According to a fourteenth aspect, in the thirteenth aspect, the calculating unit may calculate the cumulative exposure dose with respect to the irradiation field from a point in time when the medical treatment starts to a point in time when capturing of the movie is completed, as the cumulative exposure dose. Thereby, the cumulative exposure dose until a point in time when capturing of the movie in the irradiation field excluding the region of interest is completed may be restricted to the predetermined exposure dose or less.

According to a fifteenth aspect, in the thirteenth aspect, the restricting unit may include a diaphragm unit that is provided between the radiation source and the subject and the diaphragm unit has an opening region which is configured to transmit a part of the radiation emitted from the radiation source and whose area is changeable. The control unit may control the diaphragm unit to restrict the exposure dose by changing the area of the opening region of the diaphragm unit. Thereby, the region of the irradiation field other than the region of interest may be changed. As a result, convenience may be improved.

According to a sixteenth aspect, in the fifteenth aspect, the diaphragm unit may be configured such that a transmission dose of the radiation decreases as a distance from a circumferential part of the opening region increases. Thereby, the radiation image in the irradiation field other than the region of interest may be observed.

According to a seventeenth aspect, in the thirteenth aspect, the calculating unit may calculate the cumulative exposure dose for divided regions each of which is a predetermined unit area in the irradiation field. Thereby, the exposure dose with respect to the subject may be precisely restricted, as compared with the case in which the cumulative exposure doses are collected and calculated over the entire region of the irradiation field.

According to an eighteenth aspect, in the thirteenth aspect, the control unit may perform the control following a region of interest which changes with time. Thereby, convenience may be improved.

According to a nineteenth aspect, in the eighteenth aspect, the radiation control device may further include a specifying unit that specifies a position of a predetermined part of a medical apparatus inserted into a body of the subject. The control unit may set the position specified by the specifying unit as the region of interest and perform the control. Thereby, the region of interest does not need to be previously set, and convenience may be improved.

According to a twentieth aspect, in the nineteenth aspect, the specifying unit may specify the position of the predetermined part using at least one of image recognition based on image information obtained by capturing the movie, an IC tag provided in the predetermined part, or a magnetic body provided in the predetermined part. Thereby, in a case in which the specifying unit specifies the position using the image recognition, since a member for specifying the position does not need to be provided, the invention may be realized at a low cost. In a case in which the specifying unit specifies the position using at least one of the IC tag and the magnetic body, the position may be accurately specified, as compared with the case where the specifying unit specifies the position using the image recognition.

The IC tag may be called an RFID tag, an ID tag or a wireless tag. However, the tag may be called the IC tag in this specification.

In the thirteenth aspect, a radiation detector of an indirect conversion type, which is configured such that a phosphor layer which emits light due to irradiation with radiation and a substrate at which a photoelectric conversion element which converts the light generated at the phosphor layer into a charge is formed are laminated, may be provided in the radiation image capturing unit, and image capturing may be carried out by the radiation detector.

It is preferable that the phosphor is CsI.

The radiation detector may be provided in the radiation image capturing unit such that a radiation ray is incident from a substrate side.

According to a twenty-first aspect, a radiation image capturing system includes the radiation control device of any one of the thirteenth to twentieth aspects, and a radiation image capturing device that captures a movie of a radiation image based on the radiation which is controlled by the radiation control device, which is emitted from a radiation source emitting the radiation, and which is transmitted through a subject.

According to a twenty-second aspect, a radiation image capturing system includes the radiation control device of any one of the thirteenth to twentieth aspects, and a radiation source that emits the radiation controlled by the radiation control device.

According to a twenty-third aspect, a radiation image capturing system includes the radiation control device of any one of the thirteenth to twentieth aspects, a radiation image capturing device that captures a movie of a radiation image based on the radiation which is controlled by the radiation control device, which is emitted from a radiation source emitting the radiation, and which is transmitted through a subject, and the radiation source.

As such, since the radiation image capturing system according to the twenty-first to twenty-third aspects includes the radiation control device of any one of the thirteenth to twentieth aspects, similar to the radiation control device, the exposure dose with respect to the subject may be suppressed while the quality of the radiation image in the region of interest may be prevented from being degraded.

According to the radiation control device and the radiation image capturing system of the invention, in a case in which it is determined that the cumulative exposure dose from a point in time when the medical treatment starts using the radiation irradiated from the radiation source to the subject to capture the movie of the radiation image reaches the predetermined exposure dose, the restricting unit is controlled to restrict the exposure dose with respect to the irradiation field of the radiation based on the radiation source other than the region of interest. Therefore, the exposure dose with respect to the subject may be suppressed while the quality of the radiation image in the region of interest may be prevented from being degraded.

According to a twenty-fourth aspect, a radiation control device includes a calculating unit that calculates a cumulative exposure dose of radiation irradiated from a radiation source to a subject to capture a movie of a radiation image, a restricting unit that restricts an exposure dose with respect to an irradiation field of the radiation irradiated from the radiation source excluding a region of interest, a determining unit that determines whether the cumulative exposure dose calculated by the calculating unit reaches a predetermined exposure dose, and a control unit that controls the restricting unit to restrict the exposure dose, in a case in which the determining unit determines that the cumulative exposure dose reaches the predetermined exposure dose.

As such, according to the radiation control device of the twenty-fourth aspect, in a case in which it is determined that the cumulative exposure dose of the radiation irradiated from the radiation source to the subject to capture the movie of the radiation image reaches the predetermined exposure dose, the restricting unit is controlled to restrict the exposure dose with respect to the irradiation field of the radiation based on the radiation source excluding the region of interest. Therefore, the exposure dose with respect to the subject may be suppressed while the quality of the radiation image in the region of interest may be prevented from being degraded.

According to a twenty-fifth aspect, in the twenty-fourth aspect, the calculating unit may calculate the cumulative exposure dose with respect to the irradiation field until a point in time when capturing of the movie is completed, as the cumulative exposure dose. Thereby, the cumulative exposure dose until a point in time when capturing of the movie in the irradiation field excluding the region of interest is completed may be the predetermined exposure dose or less.

According to a twenty-sixth aspect, in the twenty-fourth aspect, the calculating unit may calculate the cumulative exposure dose in a state where the cumulative exposure dose is weighted under predetermined conditions. Thereby, an actual cumulative exposure dose may be calculated. As a result, the exposure dose with respect to the subject may be accurately suppressed.

According to a twenty-seventh aspect, in the twenty-fourth aspect, the calculating unit may calculate the cumulative exposure dose for divided regions each of which is a predetermined unit area in the irradiation field. Thereby, the exposure dose with respect to the subject may be precisely restricted, as compared with the case in which the cumulative exposure doses are collected and calculated over the entire region of the irradiation field.

According to a twenty-eighth aspect, in the twenty-fourth aspect, the restricting unit may include a diaphragm unit which is provided between the radiation source and the subject and which has an opening region which is configured to transmit a part of the radiation emitted from the radiation source and whose area is changeable. The control unit may control the diaphragm unit to restrict the exposure dose by changing the area of the opening region of the diaphragm unit. Thereby, the region of the irradiation field other than the region of interest may be changed. As a result, convenience may be improved.

According to a twenty-ninth aspect, in the twenty-eighth aspect, the diaphragm unit may be configured such that a transmission dose of the radiation decreases as a distance from a circumferential part of the opening region increases. Thereby, the radiation image in the irradiation field other than the region of interest may be observed.

According to a thirtieth aspect, in the twenty-fourth aspect, the control unit may perform the control following a region of interest which changes with time. Thereby, convenience may be improved.

According to a thirty-first aspect, in the thirtieth aspect, the radiation control device may further include a specifying unit that specifies a position of a predetermined part of a medical apparatus inserted into a body of the subject. The control unit may set the position specified by the specifying unit as the region of interest and performs the control. Thereby, the region of interest does not need to be previously set, and convenience may be improved.

According to a thirty-second aspect, in the thirty-first aspect, the specifying unit may specify the position of the predetermined part using at least one of image recognition based on image information obtained by capturing the movie, an IC tag provided in the predetermined part, or a magnetic body provided in the predetermined part. Thereby, in a case in which the specifying unit specifies the position using the image recognition, since a member for specifying the position does not need to be provided, the invention may be realized at a low cost. In a case in which the specifying unit specifies the position using at least one of the IC tag and the magnetic body, the position may be accurately specified, as compared with the case in which the specifying unit specifies the position using the image recognition.

The IC tag may be called an RFID tag, an ID tag or a wireless tag. However, the tag may be called the IC tag in this specification.

In the twenty-fourth aspect, a radiation detector of an indirect conversion type, which is configured such that a phosphor layer which emits light due to irradiation of radiation and a substrate at which a photoelectric conversion element which converts the light generated at the phosphor layer into a charge is formed are laminated, may be provided in the radiation image capturing unit, and image capturing may be carried out by the radiation detector.

It is preferable that the phosphor is CsI.

The radiation detector may be provided in the radiation image capturing unit such that a radiation ray is incident from a substrate side.

According to a thirty-third aspect, a radiation image capturing system includes the radiation control device of any one of the twenty-fourth to thirty-second aspects, and a radiation image capturing device that captures a movie of a radiation image based on the radiation which is controlled by the radiation control device, which is emitted from a radiation source emitting the radiation, and which is transmitted through a subject.

According to a thirty-fourth aspect, a radiation image capturing system includes the radiation control device of any one of the twenty-fourth to thirty-second aspects, and a radiation source that emits the radiation controlled by the radiation control device.

According to a thirty-fifth aspect, a radiation image capturing system includes the radiation control device of any one of the twenty-fourth to thirty-second aspects, a radiation image capturing device that captures a movie of a radiation image based on the radiation which is controlled by the radiation control device, which is emitted from a radiation source emitting the radiation, and which is transmitted through a subject, and the radiation source.

As such, since the radiation image capturing system according to the thirty-third to thirty-fifth aspects includes the radiation control device of the invention, similar to the radiation control device, the exposure dose with respect to the subject may be suppressed while the quality of the radiation image in the region of interest may be prevented from being degraded.

According to the radiation control device and the radiation image capturing system of the invention, in a case in which it is determined that the cumulative exposure dose of the radiation irradiated from the radiation source to the subject to capture the movie of the radiation image reaches the predetermined exposure dose, the restricting unit is controlled to restrict the exposure dose with respect to the irradiation field of the radiation based on the radiation source other than the region of interest. Therefore, the exposure dose with respect to the subject may be suppressed while the quality of the radiation image in the region of interest may be prevented from being degraded.

According to a thirty-sixth aspect, a radiographic imaging management device includes a calculating unit that calculates an exposure dose of radiation per unit time, which is irradiated from a radiation source to a subject to capture a movie of a radiation image, for divided regions each of which is a predetermined unit area, and a storage unit that stores exposure dose information indicating the exposure dose calculated by the calculating unit associated with divided region specification information specifying the corresponding divided region and subject specification information specifying the subject.

The storage unit includes a semiconductor storage element such as a Random Access Memory (RAM) and a Read Only Memory (ROM), a portable recording medium such as a flexible disk, a fixed recording medium such as a hard disk or an external storage device provided in a server computer connected to a network.

As such, according to the radiographic imaging management device of the thirty-sixth aspect, the exposure dose of radiation per unit time that is irradiated from the radiation source to the subject to capture the movie of the radiation image is calculated for each of the divided regions each of which is the predetermined unit area, and the exposure dose information indicating the calculated exposure dose is stored and associated with the divided region specification information specifying the corresponding divided region and the subject specification information specifying the subject. Therefore, excessive exposure of the radiation with respect to the subject may be effectively prevented by deriving the cumulative exposure dose for each of the divided regions using the stored exposure dose information.

According to a thirty-seventh aspect, in the thirty-sixth aspect, the radiographic imaging management device may further include an acquiring unit that acquires at least one of time point information indicating a point in time when the radiation is irradiated onto the subject, medical treatment exposure dose information indicating an exposure dose of the radiation for each medical treatment, or frame rate information indicating a frame rate of capturing of the movie. The storage unit may store at least one of the time point information, the medical treatment exposure dose information, and the frame rate information acquired by the acquiring unit associated with the corresponding subject specification information. Thereby, the exposure dose that is indicated by the exposure dose information may be weighted on the basis of at least one of the time point information, the medical treatment exposure dose information, and the frame rate information acquired by the acquiring unit. Therefore, excessive exposure of the radiation with respect to the subject may be effectively prevented by deriving the cumulative exposure dose for each of the divided regions using the stored exposure dose information.

According to a thirty-eighth aspect, in the thirty-sixth aspect, the exposure dose information may indicate an exposure dose of the radiation which reaches the subject, in a state where the radiation is reduced by a diaphragm unit that is provided between the radiation source and the subject and that has an opening region which is configured to transmit a part of the radiation emitted from the radiation source and whose area is changeable. Thereby, even in the radiation image capturing system using the diaphragm unit, the cumulative exposure dose may be derived with high precision. As a result, excessive exposure of the radiation with respect to the subject may be effectively prevented.

In the thirty-sixth aspect, a radiation detector of an indirect conversion type, which is configured such that a phosphor layer which emits light due to irradiation of radiation and a substrate at which a photoelectric conversion element which converts the light generated at the phosphor layer into a charge is formed are laminated, may be provided in the radiation image capturing unit, and image capturing may be carried out by the radiation detector.

It is preferable that the phosphor is CsI.

The radiation detector may be provided in the radiation image capturing unit such that a radiation ray is incident from a substrate side.

According to a thirty-ninth aspect, a radiation image capturing system includes the radiographic imaging management device of any one of the thirty-sixth to thirty-eighth aspects, and a radiation image capturing device that captures a movie of a radiation image based on the radiation which is managed by the radiographic imaging management device, which is emitted from a radiation source emitting the radiation, and which is transmitted through the subject.

According to a fortieth aspect, a radiation image capturing system includes the radiographic imaging management device of any one of the thirty-sixth to thirty-eighth aspects, and a radiation source that emits the radiation managed by the radiographic imaging management device.

According to a forty-first aspect, a radiation image capturing system includes the radiographic imaging management device of any one of the thirty-sixth to thirty-eighth aspects, a radiation image capturing device that captures a movie of a radiation image based on the radiation which is managed by the radiographic imaging management device, which is emitted from a radiation source emitting the radiation, and which is transmitted through the subject, and the radiation source.

As such, since the radiation image capturing system according to the thirty-ninth to forty-first aspects includes the radiographic imaging management device of the invention, similar to the radiographic imaging management device, excessive exposure of the radiation with respect to the subject may be effectively prevented.

According to the radiographic imaging management device and the radiation image capturing system of the invention, the exposure dose of radiation per unit time that is irradiated from the radiation source to the subject to capture the movie of the radiation image is calculated for each of the divided regions each of which is the predetermined unit area, and the exposure dose information indicating the calculated exposure dose is stored and associated with the divided region specification information which specifies the corresponding divided region and the subject specification information which specifies the subject. Therefore, excessive exposure of the radiation with respect to the subject may be effectively prevented by deriving the cumulative exposure dose for each of the divided regions using the stored exposure dose information.

What is claimed is:

1. A radiation control device comprising:
   a calculating unit that calculates a cumulative exposure dose from a point in time when medical treatment starts, using radiation irradiated from a radiation source to a subject to capture a movie of a radiation image, to a point in time when capturing of the movie is completed or a cumulative exposure dose received by the subject until a point in time when capturing of the movie is completed;
   a restricting unit that restricts an exposure dose with respect to an irradiation field of the radiation irradiated from the radiation source excluding a region of interest;
   a determining unit that determines whether the cumulative exposure dose calculated by the calculating unit reaches a predetermined exposure dose; and
   a control unit that controls the restricting unit to restrict the exposure dose, in a case in which the determining unit determines that the cumulative exposure dose reaches the predetermined exposure dose.

2. The radiation control device of claim 1,
wherein the calculating unit calculates the cumulative exposure dose in a state where the cumulative exposure dose is weighted under predetermined conditions.

3. The radiation control device of claim 1,
wherein the calculating unit calculates the cumulative exposure dose for divided regions each of which is a predetermined unit area in the irradiation field.

4. The radiation control device of claim 1,
wherein the restricting unit includes a diaphragm unit which is provided between the radiation source and the subject and which has an opening region which is configured to transmit a part of the radiation emitted from the radiation source and whose area is changeable, and
wherein the control unit controls the diaphragm unit to restrict the exposure dose by changing the area of the opening region of the diaphragm unit.

5. The radiation control device of claim 4,
wherein the diaphragm unit is configured such that a transmission dose of the radiation decreases as a distance from a circumferential part of the opening region increases.

6. The radiation control device of claim 1,
wherein the control unit performs the control following a region of interest which changes with time.

7. The radiation control device of claim 6, further comprising:
a specifying unit that specifies a position of a predetermined part of a medical apparatus inserted into a body of the subject,
wherein the control unit sets the position specified by the specifying unit as the region of interest and performs the control.

8. The radiation control device of claim 7,
wherein the specifying unit specifies the position of the predetermined part using at least one of image recognition based on image information obtained by capturing the movie, an IC tag provided in the predetermined part, or a magnetic body provided in the predetermined part.

9. A radiation image capturing system comprising:
the radiation control device of claim 1; and
a radiation image capturing device that captures a movie of a radiation image based on the radiation which is controlled by the radiation control device, which is emitted from a radiation source emitting the radiation, and which is transmitted through a subject.

10. A radiation image capturing system comprising:
the radiation control device of claim 1; and
a radiation source that emits the radiation controlled by the radiation control device.

11. A radiation image capturing system comprising:
the radiation control device of claim 1;
a radiation image capturing device that captures a movie of a radiation image based on the radiation which is controlled by the radiation control device, which is emitted from a radiation source emitting the radiation, and which is transmitted through a subject; and
the radiation source.

12. A radiographic imaging management device comprising:
a calculating unit that calculates an exposure dose of radiation per unit time, which is irradiated from a radiation source to a subject to capture a movie of a radiation image, for divided regions each of which is a predetermined unit area;
a storage unit that stores exposure dose information indicating the exposure dose calculated by the calculating unit associated with divided region specification information specifying the corresponding divided region and subject specification information specifying the subject; and
an acquiring unit that acquires at least one of time point information indicating a point in time when the radiation is irradiated onto the subject, medical treatment exposure dose information indicating an exposure dose of the radiation for each medical treatment, or frame rate information indicating a frame rate of capturing of the movie,
wherein the storage unit stores the at least one of the time point information, the medical treatment exposure dose information, or the frame rate information acquired by the acquiring unit associated with the corresponding subject specification information.

13. The radiographic imaging management device of claim 12,
wherein the exposure dose information indicates an exposure dose of the radiation which reaches the subject in a state where the radiation is reduced by a diaphragm unit that is provided between the radiation source and the subject and that has an opening region which is configured to transmit a part of the radiation emitted from the radiation source and whose area is changeable.

14. A radiation image capturing system comprising:
the radiographic imaging management device of claim 12; and
a radiation image capturing device that captures a movie of a radiation image based on the radiation which is managed by the radiographic imaging management device, which is emitted from a radiation source emitting the radiation, and which is transmitted through the subject.

15. A radiation image capturing system comprising:
the radiographic imaging management device of claim 12; and
a radiation source that emits the radiation managed by the radiographic imaging management device.

16. A radiation image capturing system comprising:
the radiographic imaging management device of claim 12;
a radiation image capturing device that captures a movie of a radiation image based on the radiation which is managed by the radiographic imaging management device, which is emitted from a radiation source emitting the radiation, and which is transmitted through the subject; and
the radiation source.

* * * * *